United States Patent
Eguchi et al.

(10) Patent No.: US 11,629,194 B2
(45) Date of Patent: Apr. 18, 2023

(54) ANTI-IGF-I RECEPTOR ANTIBODIES, ENCODING NUCLEIC ACID MOLECULES AND METHODS OF USING SAID ANTIBODIES

(71) Applicant: TEIJIN PHARMA LIMITED, Tokyo (JP)

(72) Inventors: Hiroshi Eguchi, Tokyo (JP); Akira Tanokura, Tokyo (JP); Kenichiro Takagi, Tokyo (JP); Hirotsugu Kato, Tokyo (JP); Satoshi Yamamura, Tokyo (JP); Naoko Namiki, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 16/610,396

(22) PCT Filed: May 29, 2018

(86) PCT No.: PCT/JP2018/020581
§ 371 (c)(1),
(2) Date: Nov. 1, 2019

(87) PCT Pub. No.: WO2018/221521
PCT Pub. Date: Dec. 6, 2018

(65) Prior Publication Data
US 2020/0115460 A1  Apr. 16, 2020

(30) Foreign Application Priority Data
May 30, 2017 (JP) .............................. JP2017-106529

(51) Int. Cl.
| | | |
|---|---|---|
| *C07K 16/28* | (2006.01) | |
| *A61K 39/00* | (2006.01) | |
| *A61P 21/00* | (2006.01) | |
| *A61P 3/10* | (2006.01) | |
| *A01K 67/027* | (2006.01) | |
| *A61K 9/00* | (2006.01) | |
| *A61K 39/395* | (2006.01) | |

(Continued)

(52) U.S. Cl.
CPC ...... *C07K 16/2863* (2013.01); *A01K 67/0278* (2013.01); *A61K 9/0029* (2013.01); *A61K 39/3955* (2013.01); *A61K 45/06* (2013.01); *A61P 3/10* (2018.01); *A61P 21/00* (2018.01); *C12N 5/0658* (2013.01); *C12N 15/8509* (2013.01); *A01K 2207/15* (2013.01); *A01K 2217/052* (2013.01); *A01K 2267/01* (2013.01); *A61K 2039/545* (2013.01); *A61K 2039/55* (2013.01); *C07K 2317/14* (2013.01); *C07K 2317/20* (2013.01); *C07K 2317/31* (2013.01); *C07K 2317/34* (2013.01); *C07K 2317/55* (2013.01); *C07K 2317/565* (2013.01); *C07K 2317/567* (2013.01); *C07K 2317/622* (2013.01); *C07K 2317/626* (2013.01); *C07K 2317/73* (2013.01); *C07K 2317/74* (2013.01); *C07K 2317/92* (2013.01); *C12N 2015/8518* (2013.01); *C12N 2501/998* (2013.01); *C12N 2506/1323* (2013.01)

(58) Field of Classification Search
CPC ............ C07K 16/2863; C07K 2317/14; C07K 2317/20; C07K 2317/31; C07K 2317/34; C07K 2317/55; C07K 2317/565; C07K 2317/567; C07K 2317/622; C07K 2317/626; C07K 2317/73; C07K 2317/74; C07K 2317/92; C07K 16/28; A61P 21/00; A61P 3/10; A61P 1/04; A61P 1/12; A61P 1/16; A61P 1/18; A61P 3/00; A61P 3/04; A61P 9/00; A61P 9/10; A61P 9/14; A61P 11/00; A61P 13/08; A61P 13/10; A61P 13/12; A61P 15/00; A61P 17/02; A61P 17/06; A61P 19/08; A61P 19/10; A61P 21/02; A61P 21/04; A61P 25/00; A61P 27/02; A61P 27/16; A61P 35/00; A61P 35/02; A61P 37/06; A01K 67/0278; A01K 2207/15; A01K 2217/052; A01K 2267/01; A01K 67/027; A61K 9/0029; A61K 39/3955; A61K 45/00; A61K 45/06; A61K 2039/545; A61K 2039/55; A61K 35/12; A61K 35/34; A61K 35/76; A61K 39/395; A61K 48/00; C12N 5/0658; C12N 15/8509; C12N 2015/8518; C12N 2501/998; C12N 2506/1323; C12N 5/10; C12N 15/63
See application file for complete search history.

(56) References Cited

U.S. PATENT DOCUMENTS

| | | | |
|---|---|---|---|
| 2004/0025197 A1 | 2/2004 | Young et al. | |
| 2009/0130105 A1 | 5/2009 | Glaser et al. | |
| 2010/0267927 A1* | 10/2010 | Garrett | ................. G01N 33/574 530/325 |

FOREIGN PATENT DOCUMENTS

| | | |
|---|---|---|
| JP | 2004-500843 A | 1/2004 |
| JP | 2004-357612 A | 12/2004 |

(Continued)

OTHER PUBLICATIONS

Salisbury TB and Tomblin JK (Feb. 2, 2015) Frontiers in Endocrinology. 6(12):1-5. (doi: 10.3389/fendo.2015.00012).*

(Continued)

*Primary Examiner* — Robert S Landsman
(74) *Attorney, Agent, or Firm* — Sughrue Mion, PLLC

(57) ABSTRACT

The present invention provides an anti-IGF-I receptor antibody that binds specifically to an IGF-I receptor of a vertebrate and has the proliferation-inducing activity of a vertebrate-derived cell, or a fragment thereof, or derivatives of these.

44 Claims, 6 Drawing Sheets

Specification includes a Sequence Listing.

(51) Int. Cl.
  A61K 45/06   (2006.01)
  C12N 5/077   (2010.01)
  C12N 15/85   (2006.01)

(56) References Cited

FOREIGN PATENT DOCUMENTS

| | | |
|---|---|---|
| JP | 2010538012 A | 12/2010 |
| WO | 2009032782 A2 | 3/2009 |
| WO | 2009121759 A2 | 10/2009 |

OTHER PUBLICATIONS

Mahajan K and Mahajan MP (Sep. 2012) J Cell Physiol. 227(9):3178-3184. (doi: 10.1002/jcp.24065).*

Langer CJ, et al. (Jul. 1, 2014) J Clin Oncol. 32(19):2059-2066. (doi: 10.1200/JCO.2013.54.4932).*

Yip CC, et al. (Nov. 30, 1988) Biochemistry Biophys.*

Yip CC, et al. (Jan. 22, 1991) Biochemistry. 30(3):695-701. (doi: 10.1021/bi00217a016).*

Yip C.C, et al. (Nov. 30, 1988).157(1):321-329. (doi: 10.1016/s0006-291x(88)80050-0).* https://www.abcam.com/primary-antibodies/kd-value-a-quantitive-measurement-of-antibody-affinity (retrieved from the internet Jul. 16, 2022).*

Ohlsson, C., et al., "The role of liver-derived insulin-like growth factor-I", Endocrine Reviews, 2009, vol. 30, No. 5, pp. 494-535 (62 pages).

Kavran, J., et al., "How IGF-1 activates its receptor", eLife, 2014, vol. 3, pp. 1-28 (28 pages).

Bailyes, E.et al., "Insulin receptor/IGF-I receptor hybrids are widely distributed in mammalian tissues quantification of individual receptor species by selective immunoprecipitation and immunoblotting", Biochem Journal, vol. 327, 1997 (Pt. 1), pp. 209-215 (7 pages).

Pandini, G. et al., "Insulin/Insulin-like Growth Factor I Hybrid Receptors Have Different Biological Characteristics Depending on the Insulin Receptor Isoform Involved*", The Journal of Biological Chemistry, vol. 277, No. 42, Issue of Oct. 18, 2002, pp. 39684-39695 (13 pages).

Orphan Pacific, IF 2015, 84 pages in total.

Fukushima, T., et al., "Phosphatidylinositol 3-Kinase (Pl3K) Activity Bound to Insulin-like Growth Factor-1 (IGF-1) Receptor, which Is Continuously Sustained by IGF-1 Stimulation, Is Required for IGF-1-induced Cell Proliferation", The Journal of Biological Chemistry, vol. 287, No. 35, 2012, pp. 29713-29721 (10 pages).

Schiaffino, S., et al., "Regulation of skeletal muscle growth by the IGF1-Akt/PKB pathway: insights from genetic models", Skeletal Muscle, 2011, vol. 1, No. 4, pp. 1-14.

Boonen, S., et al., "Musculoskeletal Effects of the Recombinant Human IGF-I/IGF Binding Protein-3 Complex in Osteoporotic Patients with Proximal Femoral Fracture: A Double-Blind, Placebo-Controlled Pilot Study", The Journal of Clinical Endocrinology & Metabolism, vol. 87, No. 4, 2002, pp. 1593-1599 (7 pages).

Barton-Davis, E., et al., "Viral mediated expression of insulin-like growth factor I blocks the aging-related loss of skeletal muscle function", Proc. Natl. Acad. Sci. USA, vol. 95, 1998, pp. 15603-15607 (5 pages).

Lamberts, S., et al., "The Endocrinology of Aging", Science, 1997, vol. 278, pp. 419-424 (7 pages).

Musarò, A., et al., "Localized Igf-1 transgene expression sustains hypertrophy and regeneration in senescent skeletal muscle", Nature Genetics, vol. 27, 2001, pp. 195-200 (6 pages).

Temel, J.S., et al., "Anamorelin in patients with non-small-cell lung cancer and cachexia (ROMANA 1 and ROMANA 2): results from two randomised, double-blind, phase 3 trials", Lancet Oncology, vol. 17, 2016, pp. 519-531 (13 pages), www.thelancet.com/oncology.

Glass, D., "Signaling pathways perturbing muscle mass", Current Opinion in Clinical Nutrition and Metabolic Care, 2010, vol. 13, No. 3, pp. 225-229 (5 pages).

Lee, S.J., et al., "Regulation of myostatin activity and muscle growth", P.N.A.S., 2001, vol. 98, No. 16, pp. 9306-9311 (6 pages).

Amirouche, A., et al., "Down-Regulation of Akt/Mammalian Target of Rapamycin Signaling Pathway in Response to Myostatin Overexpression in Skeletal Muscle", Endocrinology, 2009, vol. 150, No. 1, pp. 286-294 (9pages).

Woodhouse, L., et al., "A Phase 2 Randomized Study Investigating the Efficacy and Safety of Myostatin Antibody LY2495655 Versus Placebo in Patients Undergoing Elective Total Hip Arthroplasty", The Journal of Frailty & Aging, vol. 5, No. 1, 2016, pp. 62-70 (9 pages).

Becker, C., et al., "Myostatin antibody (LY2495655) in older weak fallers: a proof-of-concept, randomised, phase 2 trial", Lancet Diabetes Endocrinology, vol. 3, 2015, pp. 948-957 (10 pages).

Amato, A., et al., "Treatment of sporadic inclusion body myositis with bimagrumab", Neurology, 2014, vol. 83, No. 24, pp. 2239-2246 (8 pages).

Cutfield, W., et al., "Non-Compliance with Growth Hormone Treatment in Children is Common and Impairs Linear Growth", PLoS ONE, vol. 6, Issue 1, 2011, pp. 1-3.

Bang, P., et al., "Identification and management of poor response to growth-promoting therapy in children with short stature", Clinical Endocrinology, vol. 77, 2012, pp. 169-181.

Puche, J., et al., "Human conditions of insulin-like growth factor-I (IGF-I) deficiency", Journal of Translational Medicine, 2012, vol. 10, pp. 1-29.

Kohn, A., et al., "Expression of a Constitutively Active Akt Ser/Thr Kinase in 3T3-L1 Adipocytes Stimulates Glucose Uptake and Glucose Transporter 4 Translocation", The Journal of Biological Chemistry, vol. 271, No. 49, 1996, pp. 31372-31378 (8 pages).

Cho, H., et al., "Insulin Resistance and a Diabetes Mellitus-Like Syndrome in Mice Lacking the Protein Kinase Akt2 (PKBβ)", Science, vol. 292, 2001, pp. 1728-1731 (5 pages).

Green, C., et al., "Use of Akt Inhibitor and a Drug-resistant Mutant Validates a Critical Role for Protein Kinase B/Akt in the Insulin-dependent Regulation of Glucose and System A Amino Acid Uptake", The Journal of Biological Chemistry, vol. 283, No. 41, 2008, pp. 27653-27667 (16 pages).

Insmed Inc., iPlex, "Submission for Marketing Application to FDA", Application No. 21-884, Review Date: Nov. 15, 2005, (108 pages total).

García-Fernández, M., et al., "Low Doses of Insulin-Like Growth Factor I Improve Insulin Resistance, Lipid Metabolism, and Oxidative Damage in Aging Rats", Endocrinology, vol. 149, No. 5, 2007, pp. 2433-2442 (10 pages).

Puche, J., et al., "Low Doses of Insulin-Like Growth Factor-I Induce Mitochondrial Protection in Aging Rats", Endocrinology, vol. 149, No. 5, 2007, pp. 2620-2627 (8 pages).

D'Ercole, A., et al., "Minireview: Expanding the Mind: Insulin-Like Growth Factor I and Brain Development", Endocrinology, vol. 149, No. 12, 2008, pp. 5958-5962 (5 pages).

Abuzzahab, M., et al., "IGF-I Receptor Mutations Resulting in Intrauterine and Postnatal Growth Retardation", The New England Journal of Medicine, vol. 349, No. 23, 2003, pp. 2211-2222 (12 pages).

Xiong, L., et al., "Growth-stimulatory monoclonal antibodies against human insulin-like growth factor I receptor", Proc. Natl. Acad. Sci. USA, vol. 89, 1992, pp. 5356-5360.

Runnels, H., et al., "Human Monoclonal Antibodies to the Insulin-like Growth Factor 1 Receptor Inhibit Receptor Activation and Tumor Growth in Preclinical Studies", Adv. Ther., vol. 27, No. 7, 2010, pp. 458-475.

Soos, M., et al., "A Panel of Monoclonal Antibodies for the Type I Insulin-like Growth Factor Receptor", The Journal of Biological Chemistry, vol. 267, No. 18, 1992, pp. 12955-12963.

(56) References Cited

OTHER PUBLICATIONS

Kato, H., et al., "Role of Tyrosine Kinase Activity in Signal Transduction by the Insulin-like Growth Factor-I (IGF-I) Receptor", The Journal of Biological Chemistry, vol. 268, No. 4, 1993, pp. 2655-2661 (7 pages).

Atzori, F., et al., "A Phase I Pharmacokinetic and Pharmacodynamic Study of Dalotuzumab (MK-0646), an Anti-Insulin-like Growth Factor-1 Receptor Monoclonal Antibody, in Patients with Advanced Solid Tumors", Clinical Cancer Research, vol. 17, No. 19, 2011, pp. 6304-6312 (10 pages).

De Bono, J., et al., "Phase II Randomized STUDY of Figitumumab plus Docetaxel and Docetaxel Alone with Crossover for Metastatic Castration-Resistant Prostate Cancer", Clinical Cancer Research, vol. 20, No. 7, 2014, pp. 1925-1934 (11 pages).

Woods, K., et al., "Intrauterine Growth Retardation and Postnatal Growth Failure Associated with Deletion of the Insulin-Like Growth Factor I Gene", The New England Journal of Medicine, vol. 335, No. 18, pp. 1363-1367, (Oct. 31, 1996).

Perez, R., et al., "Mitochondrial protection by low doses of insulin-like growth factor-1 in experimental cirrhosis", World Journal of Gastroenterology, vol. 14, No. 17, 2008, pp. 2731-2739.

Kang, B., et al.,"IGF-1 inhibits the mitochondrial apoptosis program in mesangial cells exposed to high glucose", American Journal of Physiol. Renal Physiol., vol. 285, 2003, pages F1013-F1024 (13 pages).

Bhaskar, V., et al., "A Fully Human, Allosteric Monoclonal Antibody that Activates the Insulin Receptor and Improves Glycemic Control", Diabetes, vol. 61, 2012, pp. 1263-1271 (9 pages).

International Search Report dated Aug. 28, 2018 from the International Bureau in application No. PCT/JP2018/020581.

Calzone et al., "Epitope-Specific Mechanisms of IGF1R Inhibition by Ganitumab", PLOS ONE, Feb. 2013, vol. 8, Issue 2, e55135, pp. 1-15 (total 15 pages).

Jones et al., "Transgenic overexpression of IGF-IR disrupts mammary ductal morphogenesis and induces tumor formation", Oncogene, 2007, vol. 26, pp. 1636-1644 (total 9 pages).

Communication, dated Apr. 21, 2020, issued by the Japanese Patent Office in JP Application No. 2019-521238.

* cited by examiner

FIG. 1

```
IGF1R_MOUSE   EMTNLKDIGLYNLRNITRGAIRIEKNADLCYLSTIDWSLILDAVSNNYIVGNKPPKECGD 180
IGF1R_RAT     EMTNLKDIGLYNLRNITRGAIRIEKNADLCYLSTIDWSLILDAVSNNYIVGNKPPKECGD 180
IGF1R_HUMAN   EMTNLKDIGLYNLRNITRGAIRIEKNADLCYLSTVDWSLILDAVSNNYIVGNKPPKECGD 180
IGF1R_CAVY    EMTNLKDIGLYNLRNITRGAIRIEKNADLCYLSTVDWSLILDAVSNNYIVGNKSPKECGD 180
IGF1R_RABIT   EMTNLKDIGLYNLRNITRGAIRIEKNADLCYLSTVDWSLILDAVSNNYIVGNKSPKECGD 180
              ****************************:********************.******

IGF1R_MOUSE   LCPGTLEEKPMCEKTTINNEYNYRCWTTNRCQKMCPSVCGKRACTENNECCHPECLGSCH 240
IGF1R_RAT     LCPGTLEEKPMCEKTTINNEYNYRCWTTNRCQKMCPSVCGKRACTENNECCHPECLGSCH 240
IGF1R_HUMAN   LCPGTMEEKPMCEKTTINNEYNYRCWTTNRCQKMCPSTCGKRACTENNECCHPECLGSCS 240
IGF1R_CAVY    LCPGTMEEKPLCEKTTINNEYNYRCWTTNRCQKMCPSACGKRACTEYQECCHPECLGSCH 240
IGF1R_RABIT   MCPGTLEEKPLCEKTAINNEYNYRCWTTNRCQKMCPSACGKRACTENNECCHPECLGSCH 240
              :****:****:****:*******************.******** :***********

IGF1R_MOUSE   TPDDNTTCVACRHYYYKGVCVPACPPGTYRFEGWRCVDRDFCANIPNAESSDSDGFVIHD 300
IGF1R_RAT     TPDDNTTCVACRHYYYKGVCVPACPPGTYRFEGWRCVDRDFCANIPNAESSDSDGFVIHD 300
IGF1R_HUMAN   APDNDTACVACRHYYYAGVCVPACPPNTYRFEGWRCVDRDFCANILSAESSDSEGFVIHD 300
IGF1R_CAVY    APDDDTACVACRHFYYAGICVPACPPGTYRFEGWRCVHRDFCANIPNAESSDSEGFVIHD 300
IGF1R_RABIT   APDDDTACVACRHYYFSGVCVPACPPNTYRFEGWRCVDRDFCANIPNADGGDSEGFVIHD 300
              :**:.:*:******:*: *.*******.*********.*******  .*:...**:******

IGF1R_MOUSE   DECMQECPSGFIRNSTQSMYCIPCEGPCPKVCGDEEKKTKTIDSVTSAQMLQGCTILKGN 360
IGF1R_RAT     GECMQECPSGFIRNSTQSMYCIPCEGPCPKVCGDEEKKTKTIDSVTSAQMLQGCTILKGN 360
IGF1R_HUMAN   GECMQECPSGFIRNGSQSMYCIPCEGPCPKVCE-EEKKTKTIDSVTSAQMLQGCTIFKGN 359
IGF1R_CAVY    GECMQECPSGFIRNGSQSMYCIPCEGPCPKVCE-EEKKTKTIDSVTSAQMLQGCTIFKGN 359
IGF1R_RABIT   GECMQECPSGFIRNGSQSMFCIPCEGPCPKVCE-EDKKTKTIDSVNSAQMLQGCTIFKGN 359
              .************.:***.*********** *:*********.*********:***
```

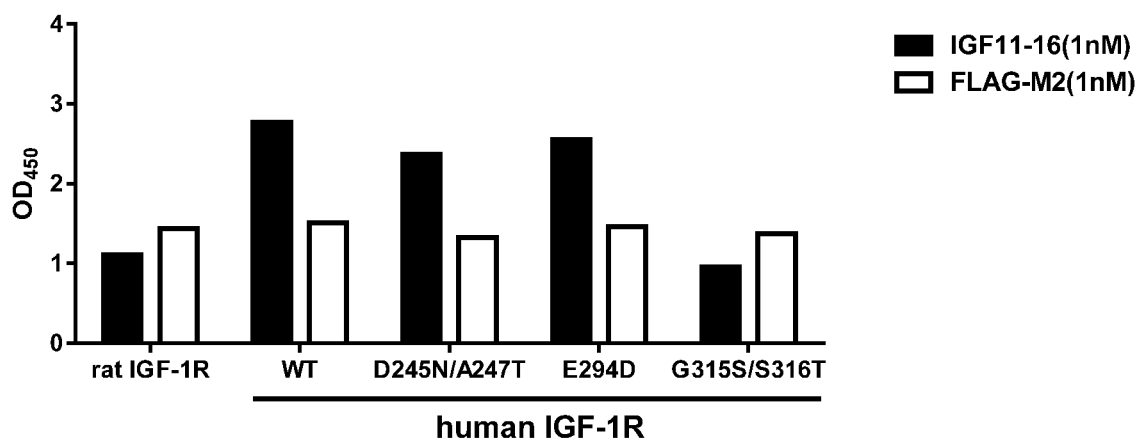

FIG. 2

Results are means and SEM from three independent experiments
(n=10-16, n=2-8 in each experiment)
*: $p<0.05$, Williams test, v.s. control
NS: $p>0.05$, Steel test, v.s. control Mean, SEM, n=6-8
: p<0.01, Dunnett's test, v.s. control
*: p<0.05, Shirley-Williams test, v.s. control Mean, SEM, n=2-3
: p<0.05, Two-Way ANOVA, v.s. control

SEQUENCE LISTING

<160> NUMBER OF SEQ ID NOS: 35

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe

```
1               5                   10                  15
Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
                35                  40                  45

Phe Arg Ser Cys Asp Leu Arg Leu Glu Met Tyr Cys Ala Pro Leu
50                  55                  60

Lys Pro Ala Lys Ser Ala
65                  70

<210> SEQ ID NO 2
<211> LENGTH: 1367
<212> TYPE: PRT
<213> ORGANISM: Homo sapiens

<400> SEQUENCE: 2

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
                35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Thr Cys Gly Lys Arg Ala Cys
                210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
                290                 295                 300
```

-continued

```
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
```

-continued

```
            725                 730                 735
Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                    805                 810                 815

Ala Ser Asn Phe Val Phe Ala Arg Thr Met Pro Ala Glu Gly Ala Asp
                    820                 825                 830

Asp Ile Pro Gly Pro Val Thr Trp Glu Pro Arg Pro Glu Asn Ser Ile
                    835                 840                 845

Phe Leu Lys Trp Pro Glu Pro Glu Asn Pro Asn Gly Leu Ile Leu Met
                    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                    885                 890                 895

Asn Pro Gly Asn Tyr Thr Ala Arg Ile Gln Ala Thr Ser Leu Ser Gly
                    900                 905                 910

Asn Gly Ser Trp Thr Asp Pro Val Phe Phe Tyr Val Gln Ala Lys Thr
                    915                 920                 925

Gly Tyr Glu Asn Phe Ile His Leu Ile Ile Ala Leu Pro Val Ala Val
                    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                    965                 970                 975

Asn Pro Glu Tyr Phe Ser Ala Ala Asp Val Tyr Val Pro Asp Glu Trp
                    980                 985                 990

Glu Val Ala Arg Glu Lys Ile Thr Met Ser Arg Glu Leu Gly Gln Gly
                    995                 1000                1005

Ser Phe Gly Met Val Tyr Glu Gly Val Ala Lys Gly Val Val Lys
            1010                1015                1020

Asp Glu Pro Glu Thr Arg Val Ala Ile Lys Thr Val Asn Glu Ala
            1025                1030                1035

Ala Ser Met Arg Glu Arg Ile Glu Phe Leu Asn Glu Ala Ser Val
            1040                1045                1050

Met Lys Glu Phe Asn Cys His His Val Val Arg Leu Leu Gly Val
            1055                1060                1065

Val Ser Gln Gly Gln Pro Thr Leu Val Ile Met Glu Leu Met Thr
            1070                1075                1080

Arg Gly Asp Leu Lys Ser Tyr Leu Arg Ser Leu Arg Pro Glu Met
            1085                1090                1095

Glu Asn Asn Pro Val Leu Ala Pro Pro Ser Leu Ser Lys Met Ile
            1100                1105                1110

Gln Met Ala Gly Glu Ile Ala Asp Gly Met Ala Tyr Leu Asn Ala
            1115                1120                1125

Asn Lys Phe Val His Arg Asp Leu Ala Ala Arg Asn Cys Met Val
            1130                1135                1140
```

Ala Glu Asp Phe Thr Val Lys Ile Gly Asp Phe Gly Met Thr Arg
1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
1355                1360                1365

<210> SEQ ID NO 3
<211> LENGTH: 5
<212> TYPE: PRT
<213> ORGANISM: Mus musculus

<400> SEQUENCE: 3

Ser Tyr Trp Met His
1               5

<210> SEQ ID NO 4
<211> LENGTH: 17
<212> TYPE: PRT
<213> ORGANISM: Mus musculus

<400> SEQUENCE: 4

Glu Thr Asn Pro Ser Asn Ser Val Thr Asn Tyr Asn Glu Lys Phe Lys
1               5                   10                  15

Ser

<210> SEQ ID NO 5
<211> LENGTH: 8
<212> TYPE: PRT
<213> ORGANISM: Mus musculus

<400> SEQUENCE: 5

Gly Arg Gly Arg Gly Phe Ala Tyr

```
<210> SEQ ID NO 6
<211> LENGTH: 11
<212> TYPE: PRT
<213> ORGANISM: Mus musculus

<400> SEQUENCE: 6

Arg Ala Ser Gln Asn Ile Asn Phe Trp Leu Ser
1               5                   10

<210> SEQ ID NO 7
<211> LENGTH: 7
<212> TYPE: PRT
<213> ORGANISM: Mus musculus

<400> SEQUENCE: 7

Lys Ala Ser Asn Leu His Thr
1               5

<210> SEQ ID NO 8
<211> LENGTH: 9
<212> TYPE: PRT
<213> ORGANISM: Mus musculus

<400> SEQUENCE: 8

Leu Gln Gly Gln Ser Tyr Pro Tyr Thr
1               5

<210> SEQ ID NO 9
<211> LENGTH: 117
<212> TYPE: PRT
<213> ORGANISM: Mus musculus

<400> SEQUENCE: 9

Gln Ile Gln Leu Gln Gln Pro Gly Ala Glu Leu Val Lys Pro Gly Ala
1               5                   10                  15

Ser Val Lys Leu Ser Cys Lys Ala Pro Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Thr Asn Pro Ser Asn Ser Val Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Gly Arg Gly Arg Gly Phe Ala Tyr Trp Gly Gln Gly Thr Leu
            100                 105                 110

Val Thr Val Ser Ala
        115

<210> SEQ ID NO 10
<211> LENGTH: 107
<212> TYPE: PRT
<213> ORGANISM: Mus musculus

<400> SEQUENCE: 10

Asp Ile Gln Met Asn Gln Ser Pro Ser Ser Leu Ser Ala Ser Leu Gly
1               5                   10                  15

Asp Thr Ile Thr Ile Thr Cys Arg Ala Ser Gln Asn Ile Asn Phe Trp
```

```
            20                  25                  30
Leu Ser Trp Cys Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95

Thr Phe Gly Gly Gly Thr Lys Leu Glu Ile Lys
            100                 105

<210> SEQ ID NO 11
<211> LENGTH: 1367
<212> TYPE: PRT
<213> ORGANISM: Cavia porcellus

<400> SEQUENCE: 11

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Ser Pro Lys
                165                 170                 175

Glu Cys Gly Asp Leu Cys Pro Gly Thr Met Glu Glu Lys Pro Leu Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Ala Cys Gly Lys Arg Ala Cys
    210                 215                 220

Thr Glu Tyr Gln Glu Cys Cys His Pro Glu Cys Leu Gly Ser Cys His
225                 230                 235                 240

Ala Pro Asp Asp Asp Thr Ala Cys Val Ala Cys Arg His Phe Tyr Tyr
                245                 250                 255

Ala Gly Ile Cys Val Pro Ala Cys Pro Pro Gly Thr Tyr Arg Phe Glu
            260                 265                 270

Gly Trp Arg Cys Val His Arg Asp Phe Cys Ala Asn Ile Pro Asn Ala
        275                 280                 285
```

-continued

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ser Gly Lys Met Tyr Phe
        435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu Arg Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Ala Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Ser Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Val Glu Glu Val Thr Glu Asn Pro Lys
        675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys

-continued

```
              705                 710                 715                 720
Val Phe Glu Asn Phe Leu His Asn Ser Ile Phe Val Pro Arg Pro Glu
                  725                 730                 735
Arg Arg Arg Arg Asp Val Ala Gln Met Ala Asn Thr Thr Met Ser Ser
                  740                 745                 750
Arg Ser Arg Asn Thr Thr Val Ala Asp Thr Tyr Asn Ala Thr Asp Pro
                  755                 760                 765
Glu Glu Leu Glu Thr Glu Tyr Pro Phe Phe Gly Ser Arg Val Asp Asn
                  770                 775                 780
Lys Glu Arg Thr Val Ile Ser Asn Leu Arg Pro Phe Thr Leu Tyr Arg
  785                 790                 795                 800
Ile Asp Ile His Ser Cys Asn His Glu Ala Glu Lys Leu Gly Cys Ser
                  805                 810                 815
Ala Ser Asn Phe Val Phe Ala Arg Thr Met Pro Ala Glu Gly Ala Asp
                  820                 825                 830
Asp Ile Pro Gly Pro Val Thr Trp Glu Ala Arg Pro Glu Asn Ser Ile
                  835                 840                 845
Phe Leu Lys Trp Pro Glu Pro Glu Asn Pro Asn Gly Leu Ile Leu Met
  850                 855                 860
Tyr Glu Ile Lys Tyr Gly Ser Gln Val Glu Asp Gln Arg Glu Cys Val
  865                 870                 875                 880
Ser Arg Gln Glu Tyr Arg Lys Tyr Gly Gly Ala Lys Leu Ser Arg Leu
                  885                 890                 895
Asn Pro Gly Asn Tyr Thr Ala Arg Ile Gln Ala Thr Ser Leu Ser Gly
                  900                 905                 910
Asn Gly Ser Trp Thr Asp Pro Val Phe Phe Tyr Val Pro Ala Lys Thr
                  915                 920                 925
Thr Tyr Glu Asn Phe Ile His Leu Ile Ile Ala Leu Pro Val Ala Ile
                  930                 935                 940
Leu Leu Ile Val Ala Gly Leu Ala Ile Met Leu Tyr Val Phe His Arg
  945                 950                 955                 960
Lys Arg Asn Ser Ser Arg Leu Gly Asn Gly Val Leu Tyr Ala Ser Val
                  965                 970                 975
Asn Pro Glu Tyr Phe Ser Ala Ala Asp Val Tyr Val Pro Asp Glu Trp
                  980                 985                 990
Glu Val Ala Arg Glu Lys Ile Thr  Met Ser Arg Glu Leu  Gly Gln Gly
                  995                 1000                1005
Ser Phe Gly Met Val Tyr Glu  Gly Val Ala Lys Gly  Val Val Lys
  1010                1015                1020
Asp Glu Pro Glu Thr Arg Val  Ala Ile Lys Thr Val  Asn Glu Ala
  1025                1030                1035
Ala Ser Met Arg Glu Arg Ile  Glu Phe Leu Asn Glu  Ala Ser Val
  1040                1045                1050
Met Lys Glu Phe Asn Cys His  His Val Val Arg Leu  Leu Gly Val
  1055                1060                1065
Val Ser Gln Gly Gln Pro Thr  Leu Val Ile Met Glu  Leu Met Thr
  1070                1075                1080
Arg Gly Asp Leu Lys Ser Tyr  Leu Arg Ser Leu Arg  Pro Glu Val
  1085                1090                1095
Glu Asn Ser Pro Ile Leu Ala  Pro Pro Ser Leu Ser  Lys Met Ile
  1100                1105                1110
Gln Met Ala Gly Glu Ile Ala  Asp Gly Met Ala Tyr  Leu Asn Ala
  1115                1120                1125
```

-continued

Asn Lys Phe Val His Arg Asp Leu Ala Ala Arg Asn Cys Met Val
1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr His Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Val Lys Asp Glu Leu Glu Ala Gly Phe Arg Glu Val Ser
    1265                1270                1275

Phe Tyr Tyr Ser Glu Glu Asn Lys Pro Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Pro Pro Asp Arg His Ser Gly His
    1310                1315                1320

Lys Gly Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Thr Asn Glu Arg Ala Leu Pro Leu Pro Gln Ser Ser Thr Cys
    1355                1360                1365

<210> SEQ ID NO 12
<211> LENGTH: 1367
<212> TYPE: PRT
<213> ORGANISM: Macaca fascicularis

<400> SEQUENCE: 12

Met Lys Ser Gly Ser Gly Glu Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile

```
            115                 120                 125
Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                    165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Ala Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                    245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                    325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
                355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                    405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
                435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                    485                 490                 495

Ser Thr Thr Thr Trp Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
                515                 520                 525

Glu Ala Pro Phe Lys Asn Val Thr Glu Tyr Asp Gly Gln Asp Ala Cys
    530                 535                 540
```

```
Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
        580                 585                 590

His Ile Arg Gly Ala Lys Ser Glu Ile Leu Tyr Ile Arg Thr Asn Ala
    595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Val Ala Asp Thr Tyr Asn Ile Thr Asp Leu
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960
```

```
Lys Arg Asn Asn Ser Arg Leu Gly Asn Gly Val Leu Tyr Ala Ser Val
            965                 970                 975

Asn Pro Glu Tyr Phe Ser Ala Ala Asp Val Tyr Val Pro Asp Glu Trp
        980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Asp Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
```

<210> SEQ ID NO 13
<211> LENGTH: 1426
<212> TYPE: PRT
<213> ORGANISM: Oryctolagus cuniculus

<400> SEQUENCE: 13

```
Met Lys Ser Gly Ser Gly Gly Ser Arg Thr Ser Ala Trp Gly Leu
1               5                   10                  15

Leu Phe Leu Ser Ala Ala Leu Ser Val Trp Pro Thr Ser Gly Glu Ile
            20                  25                  30

Cys Gly Pro Gly Ile Asp Ile Arg Asn Asp Phe Gln Gln Leu Lys Arg
            35                  40                  45

Leu Glu Asn Cys Thr Val Ile Glu Gly Phe Leu His Ile Leu Leu Ile
50                  55                  60

Ser Lys Ala Glu Asp Tyr Arg Asn Tyr Arg Phe Pro Lys Leu Thr Val
65                  70                  75                  80

Ile Thr Glu Tyr Leu Leu Phe Arg Val Ala Gly Leu Glu Ser Leu
            85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Ser Pro Lys
                165                 170                 175

Glu Cys Gly Asp Met Cys Pro Gly Thr Leu Glu Glu Lys Pro Leu Cys
                180                 185                 190

Glu Lys Thr Ala Ile Asn Asn Glu Tyr Asn Tyr Arg Cys Trp Thr Thr
            195                 200                 205

Asn Arg Cys Gln Lys Met Cys Pro Ser Ala Cys Gly Lys Arg Ala Cys
210                 215                 220

Thr Glu Asn Asn Glu Cys Cys His Pro Glu Cys Leu Gly Ser Cys His
225                 230                 235                 240

Ala Pro Asp Asp Asp Thr Ala Cys Val Ala Cys Arg His Tyr Tyr Phe
                245                 250                 255

Ser Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Pro Asn Ala
            275                 280                 285

Asp Gly Gly Asp Ser Glu Gly Phe Val Ile His Asp Gly Glu Cys Met
290                 295                 300

Gln Glu Cys Pro Ser Gly Phe Ile Arg Asn Gly Ser Gln Ser Met Phe
305                 310                 315                 320

Cys Ile Pro Cys Glu Gly Pro Cys Pro Lys Val Cys Glu Glu Asp Lys
                325                 330                 335

Lys Thr Lys Thr Ile Asp Ser Val Asn Ser Ala Gln Met Leu Gln Gly
            340                 345                 350

Cys Thr Ile Phe Lys Gly Asn Leu Leu Ile Asn Ile Arg Arg Gly Asn
            355                 360                 365
```

```
Asn Ile Ala Ser Glu Leu Glu Asn Phe Met Gly Leu Ile Glu Val Val
370                 375                 380

Thr Gly Tyr Val Lys Ile Ser His Ser His Ala Leu Val Ser Leu Ser
385                 390                 395                 400

Phe Leu Lys Asn Leu Arg Gln Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Asp
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Ile Leu His Phe Thr
                485                 490                 495

Ser Thr Asn Thr Trp Lys Asn Arg Ile Ile Leu Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Leu Glu Pro Gly Ile Leu Leu Gln Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Ile Leu Ser Ala Ser Asn Ser Ser
610                 615                 620

Ser Gln Leu Ile Val Lys Trp Ser Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Glu Asp Lys Ile Pro Ile Arg
            660                 665                 670

Lys Tyr Ala Asp Gly Thr Ile Asp Val Glu Glu Val Thr Glu Asn Pro
            675                 680                 685

Lys Thr Glu Val Cys Gly Gly Glu Lys Gly Pro Cys Cys Ala Cys Pro
690                 695                 700

Lys Thr Glu Ala Glu Lys Gln Ala Glu Lys Glu Glu Ala Glu Tyr Arg
705                 710                 715                 720

Lys Val Phe Glu Asn Phe Leu His Asn Ser Ile Phe Val Pro Arg Pro
                725                 730                 735

Glu Arg Lys Arg Arg Asp Val Ala Gln Val Ala Asn Thr Thr Leu Ser
            740                 745                 750

Gly Arg Gly Arg Asn Gly Thr Ala Val Asp Met Tyr Asn Ser Thr Asp
            755                 760                 765

Leu Glu Glu Leu Glu Thr Glu Tyr Pro Phe Phe Glu Thr Arg Val Asp
770                 775                 780

Lys Glu Ile Thr Val Ile Ser Asn Leu Arg Pro Phe Thr Ser Tyr Arg
```

```
              785                 790                 795                 800
        Ile Asp Ile His Ser Cys Asn His Glu Ala Glu Lys Leu Gly Cys Ser
                        805                 810                 815
        Ala Ser Asn Phe Val Phe Ala Arg Thr Lys Pro Ala Glu Gly Ala Asp
                        820                 825                 830
        Asp Ile Pro Gly Pro Val Thr Trp Glu Ala Arg Pro Glu Asn Ser Ile
                        835                 840                 845
        Phe Leu Lys Trp Pro Glu Pro Asn Pro Asn Gly Leu Ile Leu Met
            850                 855                 860
        Tyr Glu Ile Lys Tyr Gly Ser Gln Ile Glu Asp Gln Arg Glu Cys Val
        865                 870                 875                 880
        Ser Arg Gln Gln Tyr Arg Lys Tyr Gly Gly Ala Lys Leu Asn Arg Leu
                        885                 890                 895
        Asn Pro Gly Asn Tyr Thr Ala Arg Ile Gln Ala Thr Ser Leu Ser Gly
                        900                 905                 910
        Asn Gly Ser Trp Thr Glu Pro Val Phe Phe Tyr Val Pro Ala Lys Ala
                        915                 920                 925
        Thr Tyr Glu Ser Phe Met His Leu Ile Ile Ala Leu Pro Val Ala Ile
                        930                 935                 940
        Leu Leu Ile Val Gly Gly Leu Leu Ile Val Leu Tyr Val Phe His Arg
        945                 950                 955                 960
        Lys Arg Ser Asn Ser Arg Leu Gly Asn Gly Val Leu Tyr Ala Ser Val
                        965                 970                 975
        Asn Pro Glu Tyr Phe Ser Ala Ala Asp Val Tyr Val Pro Asp Glu Trp
                        980                 985                 990
        Glu Val Ala Arg Glu Lys Ile Thr Met Ser Arg Glu Leu Gly Gln Gly
                    995                 1000                1005
        Ser Phe Gly Met Val Tyr Glu Gly Val Ala Lys Gly Val Val Lys
            1010                1015                1020
        Asp Glu Pro Glu Thr Arg Val Ala Ile Lys Thr Val Asn Glu Ala
            1025                1030                1035
        Ala Ser Met Arg Glu Arg Ile Glu Phe Leu Asn Glu Ala Ser Val
            1040                1045                1050
        Met Lys Glu Phe Asn Cys His His Val Val Arg Leu Leu Gly Val
            1055                1060                1065
        Val Ser Gln Gly Gln Pro Thr Leu Val Ile Met Glu Leu Met Thr
            1070                1075                1080
        Arg Gly Asp Leu Lys Ser Tyr Leu Arg Ser Leu Arg Pro Glu Val
            1085                1090                1095
        Glu Ala Glu Leu Gln Arg Glu Arg Gln Arg Gln Arg Gln Asn Phe
            1100                1105                1110
        Ile Arg Arg Phe Ala Pro Arg Met Ala Ala Thr Ala Arg Ala Gly
            1115                1120                1125
        Pro Gly Arg Ser Gln Gln Pro Gly Ala Ser Ser Gly Ser Pro Thr
            1130                1135                1140
        Arg Val Gln Gly Pro Lys Asp Leu Gly His Leu Pro Leu Pro Ser
            1145                1150                1155
        Gln Asn Arg Ala Pro Ala Pro Pro Ser Leu Ser Lys Met Ile Gln
            1160                1165                1170
        Met Ala Gly Glu Ile Ala Asp Gly Met Ala Tyr Leu Asn Ala Asn
            1175                1180                1185
        Lys Phe Val His Arg Asp Leu Ala Ala Arg Asn Cys Met Val Ala
            1190                1195                1200
```

```
Glu Asp Phe Thr Val Lys Ile Gly Asp Phe Gly Met Thr Arg Asp
    1205                1210                1215

Ile Tyr Glu Thr Asp Tyr Tyr Arg Lys Gly Gly Lys Gly Leu Leu
    1220                1225                1230

Pro Val Arg Trp Met Ser Pro Glu Ser Leu Lys Asp Gly Val Phe
    1235                1240                1245

Thr Thr His Ser Asp Val Trp Ser Phe Gly Val Val Leu Trp Glu
    1250                1255                1260

Ile Ala Thr Leu Ala Glu Gln Pro Tyr Gln Gly Phe Ser Asn Glu
    1265                1270                1275

Gln Val Leu Arg Phe Val Met Glu Gly Gly Leu Leu Asp Lys Pro
    1280                1285                1290

Asp Asn Cys Pro Asp Met Leu Phe Glu Leu Met Arg Met Cys Trp
    1295                1300                1305

Gln Tyr Asn Pro Lys Met Arg Pro Ser Phe Leu Glu Ile Ile Gly
    1310                1315                1320

Ser Val Arg Asp Glu Met Glu Pro Gly Phe Arg Glu Val Ser Phe
    1325                1330                1335

Tyr Tyr Ser Glu Glu Asn Lys Pro Pro Glu Ala Glu Glu Leu Asp
    1340                1345                1350

Leu Glu Pro Glu Asn Met Glu Ser Val Pro Leu Asp Pro Ser Ala
    1355                1360                1365

Asn Ala Ala Ala Val Ala Ala Leu Gln Pro Asp Arg His Lys
    1370                1375                1380

Ala Glu Asn Gly Pro Ser Ala Gly Ala Met Val Leu Arg Ala Ser
    1385                1390                1395

Phe Asp Glu Arg Arg Pro Tyr Ala His Met Asn Gly Gly Arg Thr
    1400                1405                1410

Asp Glu Arg Ala Leu Pro Leu Pro Gln Ser Ser Thr Cys
    1415                1420                1425

<210> SEQ ID NO 14
<211> LENGTH: 1370
<212> TYPE: PRT
<213> ORGANISM: Rattus norvegicus

<400> SEQUENCE: 14

Met Lys Ser Gly Ser Gly Gly Gly Ser Pro Thr Ser Leu Trp Gly Leu
1               5                   10                  15

Val Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Phe Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
```

```
            130                 135                 140
Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Val Cys Gly Lys Arg Ala Cys
    210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
        275                 280                 285

Glu Ser Ser Asp Ser Asp Gly Phe Val Ile His Asp Gly Glu Cys Met
    290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
        355                 360                 365

Asn Asn Ile Ala Ser Glu Leu Glu Asn Phe Met Gly Leu Ile Glu Val
    370                 375                 380

Val Thr Gly Tyr Val Lys Ile Arg His Ser His Ala Leu Val Ser Leu
385                 390                 395                 400

Ser Phe Leu Lys Asn Leu Arg Leu Ile Leu Gly Glu Glu Gln Leu Glu
                405                 410                 415

Gly Asn Tyr Ser Phe Tyr Val Leu Asp Asn Gln Asn Leu Gln Gln Leu
            420                 425                 430

Trp Asp Trp Asn His Arg Asn Leu Thr Val Arg Ser Gly Lys Met Tyr
        435                 440                 445

Phe Ala Phe Asn Pro Lys Leu Cys Val Ser Glu Ile Tyr Arg Met Glu
    450                 455                 460

Glu Val Thr Gly Thr Lys Gly Arg Gln Ser Lys Gly Asp Ile Asn Thr
465                 470                 475                 480

Arg Asn Asn Gly Glu Arg Ala Ser Cys Glu Ser Asp Val Leu Arg Phe
                485                 490                 495

Thr Ser Thr Thr Thr Trp Lys Asn Arg Ile Ile Ile Thr Trp His Arg
            500                 505                 510

Tyr Arg Pro Pro Asp Tyr Arg Asp Leu Ile Ser Phe Thr Val Tyr Tyr
        515                 520                 525

Lys Glu Ala Pro Phe Lys Asn Val Thr Glu Tyr Asp Gly Gln Asp Ala
    530                 535                 540

Cys Gly Ser Asn Ser Trp Asn Met Val Asp Val Asp Leu Pro Pro Asn
545                 550                 555                 560
```

```
Lys Glu Gly Glu Pro Gly Ile Leu Leu His Gly Leu Lys Pro Trp Thr
                565             570              575

Gln Tyr Ala Val Tyr Val Lys Ala Val Thr Leu Thr Met Val Glu Asn
            580             585              590

Asp His Ile Arg Gly Ala Lys Ser Glu Ile Leu Tyr Ile Arg Thr Asn
            595             600              605

Ala Ser Val Pro Ser Ile Pro Leu Asp Val Leu Ser Ala Ser Asn Ser
        610             615              620

Ser Ser Gln Leu Ile Val Lys Trp Asn Pro Thr Leu Pro Asn Gly
625             630             635              640

Asn Leu Ser Tyr Tyr Ile Val Arg Trp Gln Arg Gln Pro Gln Asp Gly
                645             650              655

Tyr Leu Phe Arg His Asn Tyr Cys Ser Lys Asp Lys Ile Pro Ile Arg
            660             665              670

Lys Tyr Ala Asp Gly Thr Ile Asp Val Glu Glu Val Thr Glu Asn Pro
            675             680              685

Lys Thr Glu Val Cys Gly Gly Asp Lys Gly Pro Cys Cys Ala Cys Pro
690             695             700

Lys Thr Glu Ala Glu Lys Gln Ala Glu Lys Glu Ala Glu Tyr Arg
705             710             715              720

Lys Val Phe Glu Asn Phe Leu His Asn Ser Ile Phe Val Pro Arg Pro
                725             730              735

Glu Arg Arg Arg Arg Asp Val Leu Gln Val Ala Asn Thr Thr Met Ser
            740             745              750

Ser Arg Ser Arg Asn Thr Thr Val Ala Asp Thr Tyr Asn Ile Thr Asp
            755             760              765

Pro Glu Glu Phe Glu Thr Glu Tyr Pro Phe Phe Glu Ser Arg Val Asp
770             775             780

Asn Lys Glu Arg Thr Val Ile Ser Asn Leu Arg Pro Phe Thr Leu Tyr
785             790             795              800

Arg Ile Asp Ile His Ser Cys Asn His Glu Ala Glu Lys Leu Gly Cys
            805             810              815

Ser Ala Ser Asn Phe Val Phe Ala Arg Thr Met Pro Ala Glu Gly Ala
            820             825              830

Asp Asp Ile Pro Gly Pro Val Thr Trp Glu Pro Arg Pro Glu Asn Ser
        835             840              845

Ile Phe Leu Lys Trp Pro Glu Pro Glu Asn Pro Asn Gly Leu Ile Leu
        850             855             860

Met Tyr Glu Ile Lys Tyr Gly Ser Gln Val Glu Asp Gln Arg Glu Cys
865             870             875              880

Val Ser Arg Gln Glu Tyr Arg Lys Tyr Gly Gly Ala Lys Leu Asn Arg
            885             890              895

Leu Asn Pro Gly Asn Tyr Thr Ala Arg Ile Gln Ala Thr Ser Leu Ser
        900             905              910

Gly Asn Gly Ser Trp Thr Asp Pro Val Phe Phe Tyr Val Pro Ala Lys
            915             920              925

Thr Thr Tyr Glu Asn Phe Met His Leu Ile Ile Ala Leu Pro Val Ala
        930             935              940

Ile Leu Leu Ile Val Gly Gly Leu Val Ile Met Leu Tyr Val Phe His
945             950             955              960

Arg Lys Arg Asn Asn Ser Arg Leu Gly Asn Gly Val Leu Tyr Ala Ser
            965             970              975
```

```
Val Asn Pro Glu Tyr Phe Ser Ala Ala Asp Val Tyr Val Pro Asp Glu
            980                 985                 990

Trp Glu Val Ala Arg Glu Lys Ile Thr Met Asn Arg Glu Leu Gly Gln
        995                1000                1005

Gly Ser Phe Gly Met Val Tyr Glu Gly Val Ala Lys Gly Val Val
       1010                1015                1020

Lys Asp Glu Pro Glu Thr Arg Val Ala Ile Lys Thr Val Asn Glu
       1025                1030                1035

Ala Ala Ser Met Arg Glu Arg Ile Glu Phe Leu Asn Glu Ala Ser
       1040                1045                1050

Val Met Lys Glu Phe Asn Cys His His Val Val Arg Leu Leu Gly
       1055                1060                1065

Val Val Ser Gln Gly Gln Pro Thr Leu Val Ile Met Glu Leu Met
       1070                1075                1080

Thr Arg Gly Asp Leu Lys Ser Tyr Leu Arg Ser Leu Arg Pro Glu
       1085                1090                1095

Val Glu Asn Asn Leu Val Leu Ile Pro Pro Ser Leu Ser Lys Met
       1100                1105                1110

Ile Gln Met Ala Gly Glu Ile Ala Asp Gly Met Ala Tyr Leu Asn
       1115                1120                1125

Ala Asn Lys Phe Val His Arg Asp Leu Ala Ala Arg Asn Cys Met
       1130                1135                1140

Val Ala Glu Asp Phe Thr Val Lys Ile Gly Asp Phe Gly Met Thr
       1145                1150                1155

Arg Asp Ile Tyr Glu Thr Asp Tyr Tyr Arg Lys Gly Gly Lys Gly
       1160                1165                1170

Leu Leu Pro Val Arg Trp Met Ser Pro Glu Ser Leu Lys Asp Gly
       1175                1180                1185

Val Phe Thr Thr His Ser Asp Val Trp Ser Phe Gly Val Val Leu
       1190                1195                1200

Trp Glu Ile Ala Thr Leu Ala Glu Gln Pro Tyr Gln Gly Leu Ser
       1205                1210                1215

Asn Glu Gln Val Leu Arg Phe Val Met Glu Gly Gly Leu Leu Asp
       1220                1225                1230

Lys Pro Asp Asn Cys Pro Asp Met Leu Phe Glu Leu Met Arg Met
       1235                1240                1245

Cys Trp Gln Tyr Asn Pro Lys Met Arg Pro Ser Phe Leu Glu Ile
       1250                1255                1260

Ile Gly Ser Ile Lys Asp Glu Met Glu Pro Ser Phe Gln Glu Val
       1265                1270                1275

Ser Phe Tyr Tyr Ser Glu Glu Asn Lys Pro Pro Glu Pro Glu Glu
       1280                1285                1290

Leu Glu Met Glu Leu Glu Leu Glu Pro Glu Asn Met Glu Ser Val
       1295                1300                1305

Pro Leu Asp Pro Ser Ala Ser Ser Ala Ser Leu Pro Leu Pro Glu
       1310                1315                1320

Arg His Ser Gly His Lys Ala Glu Asn Gly Pro Gly Val Leu Val
       1325                1330                1335

Leu Arg Ala Ser Phe Asp Glu Arg Gln Pro Tyr Ala His Met Asn
       1340                1345                1350

Gly Gly Arg Ala Asn Glu Arg Ala Leu Pro Leu Pro Gln Ser Ser
       1355                1360                1365

Thr Cys
```

1370

<210> SEQ ID NO 15
<211> LENGTH: 1369
<212> TYPE: PRT
<213> ORGANISM: Mus musculus

<400> SEQUENCE: 15

```
Met Lys Ser Gly Ser Gly Gly Ser Pro Thr Ser Leu Trp Gly Leu
1               5                   10                  15

Val Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Phe Leu His Ile Leu Leu Ile
            50                  55                  60

Ser Lys Ala Glu Asp Tyr Arg Ser Tyr Arg Phe Pro Lys Leu Thr Val
65                  70                  75                  80

Ile Thr Glu Tyr Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Val Cys Gly Lys Arg Ala Cys
            210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
            275                 280                 285

Glu Ser Ser Asp Ser Asp Gly Phe Val Ile His Asp Asp Glu Cys Met
            290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
            355                 360                 365
```

```
Asn Asn Ile Ala Ser Glu Leu Glu Asn Phe Met Gly Leu Ile Glu Val
        370                 375                 380
Val Thr Gly Tyr Val Lys Ile Arg His Ser His Ala Leu Val Ser Leu
385                 390                 395                 400
Ser Phe Leu Lys Asn Leu Arg Leu Ile Leu Gly Glu Glu Gln Leu Glu
                405                 410                 415
Gly Asn Tyr Ser Phe Tyr Val Leu Asp Asn Gln Asn Leu Gln Gln Leu
            420                 425                 430
Trp Asp Trp Asn His Arg Asn Leu Thr Val Arg Ser Gly Lys Met Tyr
        435                 440                 445
Phe Ala Phe Asn Pro Lys Leu Cys Val Ser Glu Ile Tyr Arg Met Glu
450                 455                 460
Glu Val Thr Gly Thr Lys Gly Arg Gln Ser Lys Gly Asp Ile Asn Thr
465                 470                 475                 480
Arg Asn Asn Gly Glu Arg Ala Ser Cys Glu Ser Asp Val Leu Arg Phe
                485                 490                 495
Thr Ser Thr Thr Thr Trp Lys Asn Arg Ile Ile Thr Trp His Arg
            500                 505                 510
Tyr Arg Pro Pro Asp Tyr Arg Asp Leu Ile Ser Phe Thr Val Tyr Tyr
        515                 520                 525
Lys Glu Ala Pro Phe Lys Asn Val Thr Glu Tyr Asp Gly Gln Asp Ala
530                 535                 540
Cys Gly Ser Asn Ser Trp Asn Met Val Asp Val Asp Leu Pro Pro Asn
545                 550                 555                 560
Lys Glu Gly Glu Pro Gly Ile Leu Leu His Gly Leu Lys Pro Trp Thr
                565                 570                 575
Gln Tyr Ala Val Tyr Val Lys Ala Val Thr Leu Thr Met Val Glu Asn
        580                 585                 590
Asp His Ile Arg Gly Ala Lys Ser Glu Ile Leu Tyr Ile Arg Thr Asn
    595                 600                 605
Ala Ser Val Pro Ser Ile Pro Leu Asp Val Leu Ser Ala Ser Asn Ser
        610                 615                 620
Ser Ser Gln Leu Ile Val Lys Trp Asn Pro Pro Thr Leu Pro Asn Gly
625                 630                 635                 640
Asn Leu Ser Tyr Tyr Ile Val Arg Trp Gln Arg Gln Pro Gln Asp Gly
                645                 650                 655
Tyr Leu Tyr Arg His Asn Tyr Cys Ser Lys Asp Lys Ile Pro Ile Arg
        660                 665                 670
Lys Tyr Ala Asp Gly Thr Ile Asp Val Glu Glu Val Thr Glu Asn Pro
            675                 680                 685
Lys Thr Glu Val Cys Gly Gly Asp Lys Gly Pro Cys Cys Ala Cys Pro
690                 695                 700
Lys Thr Glu Ala Glu Lys Gln Ala Glu Lys Glu Glu Ala Glu Tyr Arg
705                 710                 715                 720
Lys Val Phe Glu Asn Phe Leu His Asn Ser Ile Phe Val Pro Arg Pro
                725                 730                 735
Glu Arg Arg Arg Arg Asp Val Met Gln Val Ala Asn Thr Thr Met Ser
        740                 745                 750
Ser Arg Ser Arg Asn Thr Thr Val Ala Asp Thr Tyr Asn Ile Thr Asp
            755                 760                 765
Pro Glu Glu Phe Glu Thr Glu Tyr Pro Phe Phe Glu Ser Arg Val Asp
770                 775                 780
Asn Lys Glu Arg Thr Val Ile Ser Asn Leu Arg Pro Phe Thr Leu Tyr
```

```
                785                 790                 795                 800
Arg Ile Asp Ile His Ser Cys Asn His Glu Ala Glu Lys Leu Gly Cys
                        805                 810                 815

Ser Ala Ser Asn Phe Val Phe Ala Arg Thr Met Pro Ala Glu Gly Ala
                820                 825                 830

Asp Asp Ile Pro Gly Pro Val Thr Trp Glu Pro Arg Pro Glu Asn Ser
                835                 840                 845

Ile Phe Leu Lys Trp Pro Glu Pro Glu Asn Pro Asn Gly Leu Ile Leu
        850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Ala Lys Leu Asn Arg
                    885                 890                 895

Leu Asn Pro Gly Asn Tyr Thr Ala Arg Ile Gln Ala Thr Ser Leu Ser
                900                 905                 910

Gly Asn Gly Ser Trp Thr Asp Pro Val Phe Phe Tyr Val Pro Ala Lys
            915                 920                 925

Thr Thr Tyr Glu Asn Phe Met His Leu Ile Ala Leu Pro Val Ala
        930                 935                 940

Ile Leu Leu Ile Val Gly Gly Leu Val Ile Met Leu Tyr Val Phe His
945                 950                 955                 960

Arg Lys Arg Asn Asn Ser Arg Leu Gly Asn Gly Val Leu Tyr Ala Ser
                    965                 970                 975

Val Asn Pro Glu Tyr Phe Ser Ala Ala Asp Val Tyr Val Pro Asp Glu
                980                 985                 990

Trp Glu Val Ala Arg Glu Lys Ile Thr Met Asn Arg Glu Leu Gly Gln
            995                 1000                1005

Gly Ser Phe Gly Met Val Tyr Glu Gly Val Ala Lys Gly Val Val
        1010                1015                1020

Lys Asp Glu Pro Glu Thr Arg Val Ala Ile Lys Thr Val Asn Glu
        1025                1030                1035

Ala Ala Ser Met Arg Glu Arg Ile Glu Phe Leu Asn Glu Ala Ser
        1040                1045                1050

Val Met Lys Glu Phe Asn Cys His His Val Val Arg Leu Leu Gly
        1055                1060                1065

Val Val Ser Gln Gly Gln Pro Thr Leu Val Ile Met Glu Leu Met
        1070                1075                1080

Thr Arg Gly Asp Leu Lys Ser Tyr Leu Arg Ser Leu Arg Pro Glu
        1085                1090                1095

Val Glu Gln Asn Asn Leu Val Leu Ile Pro Pro Ser Leu Ser Lys
        1100                1105                1110

Met Ile Gln Met Ala Gly Glu Ile Ala Asp Gly Met Ala Tyr Leu
        1115                1120                1125

Asn Ala Asn Lys Phe Val His Arg Asp Leu Ala Ala Arg Asn Cys
        1130                1135                1140

Met Val Ala Glu Asp Phe Thr Val Lys Ile Gly Asp Phe Gly Met
        1145                1150                1155

Thr Arg Asp Ile Tyr Glu Thr Asp Tyr Tyr Arg Lys Gly Gly Lys
        1160                1165                1170

Gly Leu Leu Pro Val Arg Trp Met Ser Pro Glu Ser Leu Lys Asp
        1175                1180                1185

Gly Val Phe Thr Thr His Ser Asp Val Trp Ser Phe Gly Val Val
        1190                1195                1200
```

| | | | | | | | | | | |
|---|---|---|---|---|---|---|---|---|---|---|
| Leu | Trp | Glu | Ile | Ala | Thr | Leu | Ala | Glu | Gln | Pro | Tyr | Gln | Gly | Leu |
| | 1205 | | | | 1210 | | | | 1215 | |

Ser Asn Glu Gln Val Leu Arg Phe Val Met Glu Gly Gly Leu Leu
    1220                1225                1230

Asp Lys Pro Asp Asn Cys Pro Asp Met Leu Phe Glu Leu Met Arg
    1235                1240                1245

Met Cys Trp Gln Tyr Asn Pro Lys Met Arg Pro Ser Phe Leu Glu
    1250                1255                1260

Ile Ile Gly Ser Ile Lys Asp Glu Met Glu Pro Ser Phe Gln Glu
    1265                1270                1275

Val Ser Phe Tyr Tyr Ser Glu Glu Asn Lys Pro Pro Glu Pro Glu
    1280                1285                1290

Glu Leu Glu Met Glu Pro Glu Asn Met Glu Ser Val Pro Leu Asp
    1295                1300                1305

Pro Ser Ala Ser Ser Ala Ser Leu Pro Leu Pro Glu Arg His Ser
    1310                1315                1320

Gly His Lys Ala Glu Asn Gly Pro Gly Pro Gly Val Leu Val Leu
    1325                1330                1335

Arg Ala Ser Phe Asp Glu Arg Gln Pro Tyr Ala His Met Asn Gly
    1340                1345                1350

Gly Arg Ala Asn Glu Arg Ala Leu Pro Leu Pro Gln Ser Ser Thr
    1355                1360                1365

Cys

```
<210> SEQ ID NO 16
<211> LENGTH: 4128
<212> TYPE: DNA
<213> ORGANISM: Homo sapiens

<400> SEQUENCE: 16
```

| | |
|---|---|
| atgaagtctg gctccggagg agggtccccg acctcgctgt gggggctcct gtttctctcc | 60 |
| gccgcgctct cgctctggcc gacgagtgga gaaatctgcg gccaggcat cgacatccgc | 120 |
| aacgactatc agcagctgaa agcgcctggag aactgcacgg tgatcgaggg ctacctccac | 180 |
| atcctgctca tctccaaggc cgaggactac cgcagctacc gcttccccaa gctcacggtc | 240 |
| attaccgagt acttgctgct gttccgagtg gctggcctcg agagcctcgg agacctcttc | 300 |
| cccaacctca cggtcatccg cggctggaaa ctcttctaca actacgccct ggtcatcttc | 360 |
| gagatgacca atctcaagga tattgggctt tacaacctga ggaacattac tcgggggggcc | 420 |
| atcaggattg agaaaaatgc tgacctctgt tacctctcca ctgtggactg gtccctgatc | 480 |
| ctggatgcgg tgtccaataa ctacattgtg gggaataagc ccccaaagga atgtggggac | 540 |
| ctgtgtccag ggaccatgga ggagaagccg atgtgtgaga agaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccaccccg agtgcctggg cagctgcagc | 720 |
| gcgcctgaca acgacacggc ctgtgtagct tgccgccact actactatgc cggtgtctgt | 780 |
| gtgcctgcct gcccgcccaa cacctacagg tttgagggct ggcgctgtgt ggaccgtgac | 840 |
| ttctgcgcca acatcctcag cgccgagagc agcgactccg aggggtttgt gatccacgac | 900 |
| ggcgagtgca tgcaggagtg cccctcgggc ttcatccgca acggcagcca gagcatgtac | 960 |
| tgcatcccctt gtgaaggtcc ttgcccgaag gtctgtgagg aagaaaagaa aacaaagacc | 1020 |
| attgattctg ttacttctgc tcagatgctc caaggatgca ccatcttcaa gggcaatttg | 1080 |

```
ctcattaaca tccgacgggg gaataacatt gcttcagagc tggagaactt catgggctc       1140
atcgaggtgg tgacgggcta cgtgaagatc cgccattctc atgccttggt ctccttgtcc     1200
ttcctaaaaa accttcgcct catcctagga gaggagcagc tagaaggaa ttactccttc      1260
tacgtcctcg acaaccagaa cttgcagcaa ctgtgggact gggaccaccg caacctgacc     1320
atcaaagcag ggaaaatgta ctttgctttc aatcccaaat tatgtgtttc gaaatttac      1380
cgcatggagg aagtgacggg gactaaaggg cgccaaagca aggggacat aaacaccagg      1440
aacaacgggg agagagcctc ctgtgaaagt gacgtcctgc atttcacctc caccaccacg    1500
tcgaagaatc gcatcatcat aacctggcac cggtaccggc cccctgacta cagggatctc    1560
atcagcttca ccgtttacta caaggaagca ccctttaaga atgtcacaga gtatgatggg    1620
caggatgcct gcggctccaa cagctggaac atggtggacg tggacctccc gcccaacaag    1680
gacgtggagc ccggcatctt actacatggg ctgaagccct ggactcagta cgccgtttac    1740
gtcaaggctg tgaccctcac catggtggag aacgaccata tccgtggggc caagagtgag   1800
atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc   2100
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catcttttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga agatcacc     3000
atgagccggg aacttgggca ggggtcgttt gggatggtct atgaaggagt tgccaagggt    3060
gtggtgaaag atgaacctga accagagtg gccattaaaa cagtgaacga ggccgcaagc    3120
atgcgtgaaa ggattgagtt tctcaacgaa gcttctgtga tgaaggagtt caattgtcac    3180
catgtggtgc gattgctggg tgtggtgtcc caaggccagc aacactggt catcatggaa    3240
ctgatgacac ggggcgatct caaaagttat ctccggtctc tgaggccaga aatggagaat    3300
aatccagtcc tagcacctcc aagcctgagc aagatgattc agatggccgg agagattgca    3360
gacggcatgg catacctcaa cgccaataag ttcgtccaca gagaccttgc tgcccggaat    3420
```

| | |
|---|---|
| tgcatggtag ccgaagattt cacagtcaaa atcggagatt ttggtatgac gcgagatatc | 3480 |
| tatgagacag actattaccg gaaaggaggg aaagggctgc tgcccgtgcg ctggatgtct | 3540 |
| cctgagtccc tcaaggatgg agtcttcacc acttactcgg acgtctggtc cttcggggtc | 3600 |
| gtcctctggg agatcgccac actggccgag cagccctacc agggcttgtc caacgagcaa | 3660 |
| gtccttcgct tcgtcatgga gggcggcctt ctggacaagc cagacaactg tcctgacatg | 3720 |
| ctgtttgaac tgatgcgcat gtgctggcag tataacccca agatgaggcc ttccttcctg | 3780 |
| gagatcatca gcagcatcaa agaggagatg gagcctggct ccgggaggt ctccttctac | 3840 |
| tacagcgagg agaacaagct gcccgagccg gaggagctgg acctggagcc agagaacatg | 3900 |
| gagagcgtcc ccctggaccc ctcggcctcc tcgtcctccc tgccactgcc cgacagacac | 3960 |
| tcaggacaca aggccgagaa cggccccggc cctggggtgc tggtcctccg cgccagcttc | 4020 |
| gacgagagac agccttacgc ccacatgaac gggggccgca agaacgagcg ggccttgccg | 4080 |
| ctgccccagt cttcgacctg cgattataag gatgacgatg acaagtag | 4128 |

<210> SEQ ID NO 17
<211> LENGTH: 4128
<212> TYPE: DNA
<213> ORGANISM: Cavia porcellus

<400> SEQUENCE: 17

| | |
|---|---|
| atgaagtctg gctccggagg agggtccccg acctcgctgt gggggctcct gtttctctct | 60 |
| gctgcgctct cgctctggcc gacgagtgga gaaatctgtg gccgggcat cgacatccgc | 120 |
| aatgactatc agcagctaaa acgcctggag aactgcacgg tgatcgaggg ctacctccac | 180 |
| atcctgctca tctccaaggc cgaggactac cgcagctacc gcttccccaa gctcaccgtc | 240 |
| atcaccgagt acttgctgct gttccgggtc gctggcctcg agagcctcgg agacctcttc | 300 |
| ccgaacctca ccgtcatccg cggctggaaa ctcttctata actacgccct ggtcatcttc | 360 |
| gagatgacca acctgaagga tattgggctt tacaacctga ggaacattac tcggggggcc | 420 |
| atcaggattg agaagaatgc tgacctgtgc tacctctcca cagtggactg gtcgctgatc | 480 |
| ctggatgcgg tgtccaataa ctacattgtg gggaacaagt ccccaaagga atgtggagac | 540 |
| ctgtgtccag ggaccatgga ggagaaacca ttgtgcgaga agaccaccat caacaatgag | 600 |
| tacaactacc gctgctggac cacaaatcgc tgccagaaaa tgtgcccaag tgcctgcggg | 660 |
| aagcgtgcgt gcaccgagta ccaggagtgc tgccatcctg agtgcctggg cagctgccat | 720 |
| gcacccgacg acgacacggc ctgtgtggcc tgcagacact tctactatgc tggcatctgc | 780 |
| gtgcccgcct gtccacccgg cacctaccgc ttcgagggct ggcgctgtgt gcaccgagac | 840 |
| ttctgcgcca catcccccaa tgctgagagc agtgactccg agggcttcgt catccatgac | 900 |
| ggggagtgca tgcaggagtg tccctcgggc ttcatccgca cggcagcca gagcatgtac | 960 |
| tgcatccctt gtgaaggtcc ttgccccaag gtctgcgagg aagaaaagaa gacgaaaacc | 1020 |
| attgactctg tgacttctgc tcagatgctc aagggtgca ccatcttcaa gggcaacctg | 1080 |
| ctcattaata tccgacgggg caataacatt gcgtcggaac tggagaactt catggggctc | 1140 |
| attgaggtgg tgactggcta cgtgaagatc cgccattccc atgccttggt ctccttgtcc | 1200 |
| ttcctgaaaa accttcgcct gatcctgggg gaggagcagc tggaagggaa ctactccttc | 1260 |
| tacgtcctgg acaaccagaa cctgcagcag ctgtgggatt gggaccaccg caacctcacc | 1320 |
| atcaaatctg gaagatgta ctttgctttc aatcccaaac tgtgtgtctc tgaaatttac | 1380 |
| cgcatggaag aagtgacggg gacgaaaggg cgccagagca aggggacat aaacaccagg | 1440 |

-continued

```
aacaacgggg aacgagcctc ctgtgaaagt gacgtattgc gtttcacctc caccaccaca    1500
tcgaagaacc gcattatcat cacctggcac cggtaccggc ccccagacta cagggatctc    1560
atcagcttca ctgtttacta caaggaggca ccgtttaaaa atgtcaccga gtatgatggg    1620
caggatgctt gtggctccaa cagttggaac atggtggacg tggacctgcc tcctaacaag    1680
gacgcggagc ctggcatcct actgcatggg ctgaagccct ggacacagta cgcggtctat    1740
gtcaaggccg tgaccctcac catggtagag aacgaccaca tccgtggggc caagagtgaa    1800
atcttgtaca ttcgcaccaa tgcttcagtt ccttccattc ccctggatgt cctttcggca    1860
tccaactcct cttctcagct catcgtcaag tggaaccccc catctctgcc caacggaaac    1920
ctgagttatt atatcgtgcg gtggcagcgg cagcctcagg acagctacct ataccggcac    1980
aattactgct ccaaagacaa aatccccatc agaaagtatg cggatggcac catcgatgtc    2040
gaagaggtca ccgagaaccc caagactgaa gtatgtggtg gcgagaaagg gccttgctgc    2100
gcttgcccca aaaccgaagc cgagaagcag gccgagaagg aggaggccga gtaccggaaa    2160
gtgtttgaga atttcctgca caactccatc ttcgtgccga ggcctgaaag gaggcggcga    2220
gatgttgcgc agatggccaa caccaccatg tccagccgca gcaggaacac cacggtggct    2280
gatacctaca atgccacaga tccagaggag ctagagaccg aataccctt ctttgagagc    2340
agagtggata caaggaaag aactgtaatt caaacctcc ggccttttac cttgtaccgc    2400
attgacatcc acagctgtaa ccatgaggct gagaagctgg gctgcagcgc ttctaacttt    2460
gtttttgcaa gaaccatgcc cgcagaagga gcagatgaca ttcctggccc ggtgacgtgg    2520
gaagcaaggc ctgaaaactc catctttta aagtggccag agcctgagaa tcctaatgga    2580
ttgattctaa tgtacgaaat aaaatacgga tcacaagttg aggatcagcg agaatgtgtg    2640
tccagacagg aatacaggaa atacggaggg gccaagctta gccggctaaa cccagggaac    2700
tatacagccc ggattcaagc tacctcgctc tctgggaatg ggtcgtggac agatcctgtg    2760
tttttctatg tcccagccaa aacaacgtat gaaaacttca tccatctgat catcgctctg    2820
ccagtcgcca tcctgttgat tgtggcaggc ttggcgataa tgctgtacgt cttccatagg    2880
aagagaaaca gcagcaggct ggggaatgga gtgttgtacg cctctgtgaa cccggagtac    2940
ttcagtgctg cggatgtgta cgttcctgat gagtgggagg tagcgcgaga aagatcacc    3000
atgagccggg agctggggca aggctccttt gggatggtct acgaaggagt ggctaaaggt    3060
gtggtgaaag acgagcctga acccgggta gccatcaaga cagtgaacga ggccgcaagc    3120
atgcgtgaaa ggatcgagtt tctcaatgag gcctctgtga tgaaggagtt caactgtcat    3180
catgtggtgc gactgctagg cgtggtgtcc cagggccagc ccacactggt catcatggag    3240
ctgatgacgc gggggatct caagagctat ctcaggtctt tgaggccgga agtagagaat    3300
agccccatcc tggcacctcc aagcctcagc aagatgatcc agatggccgg agagattgca    3360
gatggcatgg cataccctcaa cgccaacaag tttgtccaca gagaccttgc tgcccgcaat    3420
tgcatggtag ctgaagattt cacagtcaaa attggagatt ttgggatgac gcgagatatt    3480
tacgagacag actactaccg gaaaggaggg aaagggctgc tgcctgtgcg ctggatgtct    3540
cctgagtccc tcaaggatgg agtcttcacc actcattcgg acgtctggtc cttcggggtc    3600
gtcctctggg agatcgccac gctggctgag cagccatacc agggcttgtc caacgagcaa    3660
gtccttcgct tcgtcatgga gggtggcctc ctggacaaaa ccgacaactg cccagacatg    3720
ctgtttgagc tgatgcgcat gtgctggcag tacaacccca agatgaggcc ttccttcctg    3780
```

| | |
|---|---|
| gagatcatca gcagcgtcaa agacgagctg gaggccggct tccggaggt ctccttctac | 3840 |
| tacagcgagg agaacaagcc gcccgagccg gaggagctgg acctggagcc cgagaacatg | 3900 |
| gagagcgtcc cgctggaccc atcagcctcc tcgtcctccc tgccgccgcc cgacagacac | 3960 |
| tcaggacaca agggcgagaa cggcccgggc ccggcgtgc tggtgctccg cgccagcttc | 4020 |
| gacgagagac agccttacgc gcacatgaac ggaggccgca cgaacgagag ggccttgccg | 4080 |
| ctgccccagt cgtcaacctg cgattataag gatgacgatg acaagtga | 4128 |

```
<210> SEQ ID NO 18
<211> LENGTH: 4128
<212> TYPE: DNA
<213> ORGANISM: Macaca fascicularis

<400> SEQUENCE: 18
```

| | |
|---|---|
| atgaagtctg gctctggaga agggtccccg acctcgctgt gggggctcct gtttctctcc | 60 |
| gccgcgctct cgctctggcc gacgagtgga gaaatctgtg gccgggcat cgacatccgc | 120 |
| aacgactatc agcagctgaa gcgcctggag aactgcacgg tgatcgaggg ctacctccac | 180 |
| atcctgctca tctccaaggc cgaggactac cgcagctacc gcttccccaa gctcacggtc | 240 |
| atcaccgagt acttgctgtt gttccgagtg gctggcctag agagcctcgg agacctgttc | 300 |
| cccaacctca cggtaatccg cggctggaaa ctcttctaca actacgccct ggtcatcttt | 360 |
| gagatgacca atctcaagga tattgggctt acaacctga ggaacattac tcgggggcc | 420 |
| atcaggattg agaaaaatgc tgacctctgt tacctctcca ctgtggactg gtccctgatc | 480 |
| ctggatgcag tgtccaataa ctacattgtg gggaataagc ccccaaagga atgcggggac | 540 |
| ctgtgtccgg ggaccatgga ggagaagccg atgtgcgaga agaccaccat caacaatgag | 600 |
| tacaactacc gctgctggac cacaaaccgc tgccagaaaa tgtgcccgag tgcctgtggg | 660 |
| aagagggcat gcaccgagaa caacgagtgc tgccaccccg agtgcctggg cagctgcagc | 720 |
| gcgcctgaca cgacacggc ctgtgtagcc tgccgccact actactacgc cggtgtctgc | 780 |
| gtgcctgcct gcccgcccaa cacctacagg tttgagggct ggcgctgtgt ggaccgtgac | 840 |
| ttctgcgcca catcctcag tgccgagagc agcgactccg agggtttcgt gatccacgac | 900 |
| ggcgagtgca tgcaggagtg cccctcaggc ttcatccgca acggcagcca gagcatgtac | 960 |
| tgcatccctt gtgaaggtcc ttgccccaag gtctgtgagg aagaaaagaa aacaaagacc | 1020 |
| attgattctg ttacttctgc tcagatgctt caaggatgca ccatcttcaa gggcaatttg | 1080 |
| ctcattaaca tccgacgggg gaataacatt gcttcagaac tggagaactt catgggcctc | 1140 |
| atcgaggtgg tgacgggcta cgtgaagatc cgccattccc atgccttggt ctccttgtcc | 1200 |
| ttcctaaaaa accttcgcct catcttagga gaggagcagc tagaagggaa ttactccttc | 1260 |
| tacgtcctcg acaaccagaa cttgcagcaa ctatgggact gggaccaccg caacctgacc | 1320 |
| atcaaagcag ggaaaatgta ctttgctttc aatcccaaat tgtgtgtttc ggaaatttac | 1380 |
| cgcatggagg aagtgacggg gactaaaggg cgccaaagca aggggacat aaacaccagg | 1440 |
| aacaacgggg aaagagcctc ctgtgaaagt gacgtcctgc atttcacctc caccaccacg | 1500 |
| tggaagaatc gcatcatcat aacctggcac cggtaccggc ccctgactac agggatctc | 1560 |
| atcagcttca ccgtttacta caaggaagca ccttttaaga atgtcacgga gtatgatggg | 1620 |
| caggatgcct gcggctccaa cagctggaac atggtggacg tggacctccc gccaacaag | 1680 |
| gacgtggagc ccggcatctt actgcatggg ctgaagccct ggactcagta cgccgtttac | 1740 |
| gtcaaggctg tgaccctcac catggtggag aacgaccata tccgtggggc caagagtgag | 1800 |

| | |
|---|---|
| atcttgtaca ttcgcaccaa tgcttcagtt ccttccattc ccttggacgt tctttcagca | 1860 |
| tcgaactcct cttctcagtt aatcgtgaag tggaaccctc cctctctgcc caacggcaac | 1920 |
| ctgagttact acattgtgcg ctggcagcgg cagcctcagg acggctacct ttaccggcac | 1980 |
| aattactgct ccaaagacaa aatccccatc aggaagtatg ccgacggcac cattgacatt | 2040 |
| gaggaggtca cagagaaccc gaagactgag gtgtgtggtg gagagaaagg gccttgctgc | 2100 |
| gcctgcccca aaactgaagc tgagaagcag gccgagaagg aggaggctga gtaccgcaaa | 2160 |
| gtctttgaga atttcctgca caactccatc tttgtgccca gacctgaaag gaagcgggaga | 2220 |
| gatgtcatgc aagtggccaa caccaccatg tccagccgaa gcaggaacac cacggtggca | 2280 |
| gacacctaca acatcacaga tctggaagag ctagagacag agtaccettt ctttgagagc | 2340 |
| agagtggata taaggagag aactgtcatt tctaaccttc ggcctttcac attgtaccgc | 2400 |
| attgatatcc acagctgcaa ccacgaggct gagaaactgg gctgcagcgc ctccaacttt | 2460 |
| gtctttgcaa ggactatgcc tgcagaagga gcagatgaca ttcctgggcc agtgacctgg | 2520 |
| gagccaaggc ctgaaaactc catcttttta aagtggccag aacctgagaa tcccaatgga | 2580 |
| ttgattctaa tgtatgaaat aaaatacgga tcacaagttg aggatcagcg agaatgtgtg | 2640 |
| tccagacagg aatacaggaa gtatggaggg gccaagctaa accggctaaa cccggggaac | 2700 |
| tacacagccc ggattcaggc tacatctctc tctgggaatg ggtcgtggac agatcctgtg | 2760 |
| ttcttctatg tccaggccaa aacaggatac gaaaacttca tccatctgat catcgctctg | 2820 |
| cccgtcgctg tcctgttgat cgtgggaggg ttggtgatca tgctgtacgt cttccataga | 2880 |
| aagagaaata acagcaggct ggggaatgga gtgctgtacg cgtctgtgaa cccggagtac | 2940 |
| ttcagcgctg cggatgtgta cgttcctgat gagtgggagg tggctcggga gaagatcacc | 3000 |
| atgagccggg aacttgggca ggggtcgttt gggatggtct atgaaggagt tgccaagggt | 3060 |
| gtggtgaaag acgaacctga aaccagagtg gccattaaaa cagtgaacga ggccgcgagc | 3120 |
| atgcgtgaaa ggatcgagtt tctcaacgag gcttctgtga tgaaggagtt caattgtcac | 3180 |
| catgtggtgc ggttgctggg tgtggtgtcc cagggccagc caacgctggt catcatggaa | 3240 |
| ctgatgacgc ggggcgatct caaaagttat ctccggtctc tgaggccaga aatggagaat | 3300 |
| aatccagtcc tagcacctcc aagcctaagc aagatgattc agatggctgg agagattgca | 3360 |
| gacggcatgg catacctcaa cgccaacaag ttcgtccaca gagaccttgc tgcccggaat | 3420 |
| tgcatggtag ccgaggattt cacagtcaaa attggagatt ttgggatgac gcgagatatc | 3480 |
| tatgagacag actattaccg gaaaggaggg aaagggctgt tgcccgtgcg ctggatgtct | 3540 |
| cccgagtccc tcaaggatgg agtcttcacc acttactcgg acgtctggtc cttcggggtt | 3600 |
| gtcctctggg agatcgccac actggccgag cagccctacc agggcttgtc caacgagcaa | 3660 |
| gtccttcgct tcgtcatgga gggcggcctt ctggacaagc cagacaactg ccccgacatg | 3720 |
| ctgtttgaat tgatgcgcat gtgctggcag tacaacccca agatgaggcc ttccttcctg | 3780 |
| gagatcatca gcagcatcaa agacgagatg gagcctggct ccgggaggt ctccttctac | 3840 |
| tacagtgagg agaacaagct gcccgagccg gaggagctgg acctggagcc agagaacatg | 3900 |
| gagagcgtcc cctggaccc ctcggcctcc tcgtcctccc tgccactgcc cgacagacac | 3960 |
| tcaggacaca aggccgagaa cggccccggc cctggagtgc tggtgctccg cgccagcttc | 4020 |
| gatgagagac agccttacgc acacatgaac ggtggccgca agaacgagcg ggccttgccg | 4080 |
| ctgccccagt cttcgacctg cgattataag gatgacgatg acaagtga | 4128 |

<210> SEQ ID NO 19
<211> LENGTH: 4302
<212> TYPE: DNA
<213> ORGANISM: Oryctolagus cuniculus

<400> SEQUENCE: 19

| | | | | | | |
|---|---|---|---|---|---|---|
| atgaagtctg | gctccggagg | agggtcccgg | acctcggcgt | gggggctcct | gtttctctcc | 60 |
| gccgcgctct | cggtctggcc | gacgagtgga | gaaatctgcg | ggccgggcat | cgacatccgc | 120 |
| aatgacttcc | agcagctgaa | gcgcctggag | aactgcacgg | tgatcgaggg | cttcctccac | 180 |
| atcctgctca | tctccaaggc | cgaggactac | cgcaactacc | gcttccccaa | gctcaccgtc | 240 |
| atcaccgagt | acctgctgct | gttccgcgtg | gccggcctgg | agagcctcgg | ggacctgttc | 300 |
| cccaacctca | cggtcatccg | cggctggaag | ctcttctaca | actatgccct | ggtcattttc | 360 |
| gagatgacta | acctcaaaga | catagggctc | tataacctga | ggaacatcac | ccgggggggcc | 420 |
| atcaggatcg | agaagaacgc | cgacctctgc | tacctctcca | cggtggactg | gtctctcatc | 480 |
| ctggacgccg | tgtccaacaa | ctacattgtg | ggaacaagt | ccccaaagga | gtgcggggac | 540 |
| atgtgtccag | gaccttgga | ggagaagccg | ttgtgcgaga | gaccgccat | caacaacgag | 600 |
| tacaactacc | gctgctggac | caccaaccgc | tgccagaaaa | tgtgccccag | cgcgtgcggg | 660 |
| aagcgggcat | gcaccgagaa | caacgaatgc | tgccaccccg | agtgcctggg | cagctgccac | 720 |
| gcgcctgacg | acgacacggc | ctgcgtcgcc | tgccgccact | actatttctc | cggcgtctgc | 780 |
| gtgcccgcct | gccgcccaa | cacctaccga | ttcgagggct | ggcgctgcgt | ggaccgcgac | 840 |
| ttctgcgcca | acatccctaa | cgccgatggc | ggcgactccg | agggctttgt | catccacgac | 900 |
| ggcgagtgca | tgcaggagtg | cccgtcgggc | ttcatccgca | acggcagcca | gagcatgttc | 960 |
| tgcattccct | gtgaaggtcc | gtgccccaag | gtctgtgagg | aagacaagaa | acaaagacc | 1020 |
| attgattctg | ttaattctgc | tcaaatgctc | caaggctgca | ccatcttcaa | ggggaatctg | 1080 |
| ctcattaaca | tccgacgagg | caataacatt | gcctcggagc | tggagaactt | catggggctc | 1140 |
| atcgaggtgg | tgacgggcta | cgtgaagatc | agccactcgc | acgccttggt | ctccttgtcc | 1200 |
| ttcctgaaga | acctccgcca | gatcctaggg | gaggagcagc | tggaagggaa | ctactccttc | 1260 |
| tacgtcctgg | acaaccagaa | cttgcagcag | ctctgggact | gggaccaccg | caacctgacc | 1320 |
| atcaaagctg | ggagatgta | cttcgccttc | aaccccaaac | tgtgcgtgtc | ggaaatttac | 1380 |
| cgcatggagg | acgtgacggg | gacgaaagga | cgccagagca | agggcgacat | aaacaccagg | 1440 |
| aacaacgggg | agagagcctc | ctgtgagagc | gacatcctgc | atttcacctc | caccaacacg | 1500 |
| tggaagaacc | gcatcatcct | aacctggcac | cgctaccgcc | ccctgactac | agggatctc | 1560 |
| atcagcttca | ccgtctacta | caaggaggca | ccctttaaaa | atgtgacgga | gtatgatggg | 1620 |
| caggacgcct | gcggctccaa | cagctggaac | atggtggacg | tggacctccc | tcccaacaag | 1680 |
| gacctagagc | ctggtattct | actgcaaggg | ctgaagccct | ggactcagta | cgccgtctac | 1740 |
| gtcaaggccg | tgaccctcac | catggtggag | aatgaccaca | tccgagggc | caagagtgaa | 1800 |
| atcttgtaca | ttcgcaccaa | cgcctcagtt | ccttccatcc | ccttggacat | cctctcggca | 1860 |
| tccaactcct | cgtctcagct | gatcgtgaag | tggagccccc | gtcccctgcc | aacgggaac | 1920 |
| ctgagctact | acatcgtgag | gtggcagcgg | cagccccagg | acggctacct | gtaccggcac | 1980 |
| aactactgct | ccaaagacaa | aattcccatc | aggaagtatg | cggacggcac | catcgacgtg | 2040 |
| gaggaggtga | cggagaaccc | caagacggag | gtctgtggcg | agagaaggg | gccttgctgc | 2100 |
| gcgtgcccca | agaccgaagc | cgagaagcag | gctgagaagg | aggaggcgga | gtaccgcaag | 2160 |

```
gtgttcgaga acttcctgca caactccatc ttcgtgccca gacccgagag gaagcggaga    2220
gatgtcgccc aggtggccaa caccacgctg tccggccgag gcaggaacgg cacggcggtg    2280
gacatgtaca acagcacgga cctggaggag ctggagacag aatacccttt ctttgagacc    2340
agagtggaca aggagataac ggtcatatct aacctgcggc cgtttacttc ctaccgcatc    2400
gatatccaca gctgcaacca cgaggcggag aagctggggt gcagtgcctc caactttgtc    2460
tttgcgagaa ccaagcctgc agaaggagcg gatgacattc cgggccctgt gacctgggaa    2520
gcaaggcctg aaaactccat ctttctgaag tggccggaac ctgagaaccc caacggattg    2580
atcctaatgt atgagataaa atacgggtct cagatcgagg accagaggga atgtgtgtcc    2640
agacagcagt accgaaagta tggaggagcc aagctcaacc ggctaaaccc ggggaactat    2700
acagcccgga ttcaggctac gtcgctctcc gggaacgggt cgtggacgga gcctgtgttc    2760
ttctatgtcc cagccaaagc cacctacgag agcttcatgc acctgatcat cgcgctgccg    2820
gtcgccatcc tgctcatcgt gggagggctg ctgatcgtgc tgtacgtctt ccacaggaag    2880
agaagtaaca gcagactggg gaacggagtg ctgtacgcct ctgtgaaccc ggagtacttc    2940
agtgcagccg acgtatacgt ccctgacgag tgggaggtgg cgcgggagaa gatcaccatg    3000
agccgcgagc ttggccaggg ctccttcggg atggtctacg aaggcgtcgc caagggcgtg    3060
gtaaaggatg agccggaaac cagggtggcc atcaagacgg tgaacgaggc cgccagcatg    3120
cgggagagga tcgagtttct caacgaggcg tctgtgatga aggagttcaa ttgtcaccac    3180
gtggtgcggt tgctgggggt ggtgtcccag ggccagccca ccctggtcat catggagctg    3240
atgacgcgag gggacctcaa gagctatctc aggtccctgc gaccggaagt ggaggctgaa    3300
ttacagagag aaagacagag acagagacag aacttcatcc gccggttcgc tcctcggatg    3360
gccgcaacag ccagggctgg gccaggccga agccaacagc caggagcttc ttctgggtct    3420
cccacgaggt gcaggggcc caaggacctg ggccatcttc cgctgccttc ccagaatcgg    3480
gccccagccc ctccgagtct gagtaagatg atccaaatgg ccggggagat tgcagatggc    3540
atggcatacc tcaacgccaa caagttcgtg cacagagacc ttgctgcccg gaactgcatg    3600
gtggccgagg atttcacagt caagatcgga gatttcggaa tgacgcggga catctacgag    3660
acggactact accggaaagg ggggaaaggc ttgctgcccg tgcgctggat gccccccgag    3720
tccctcaaag atggagtctt caccaccac tctgacgtct ggtccttcgg agtcgtcctc    3780
tgggagatcg ccacgctggc agagcagccg taccagggat tctccaacga gcaggtcctg    3840
cgcttcgtca tggagggcgg ccttctggac aagccggaca actgccccga catgctgttt    3900
gagctgatgc gcatgtgttg gcaatacaac cccaagatgc ggccttcctt cctggagatc    3960
atcggcagtg tcagagacga gatggagccc ggcttccgcg aggtctcctt ctactacagc    4020
gaggagaaca gccgcccga ggccgaggag ctcgacctgg agcccgagaa catggagagc    4080
gtgcccctgg accccctccgc gaacgccgct gccgccgtcg ccgccctgca gcccgacagg    4140
cacaaggccg agaacggccc gagtgcaggg gcgatggtcc tgcgagccag ctttgacgag    4200
aggcgaccct acgcgcacat gaatgggggc cgcacagacg agcgggccct gccgctgccg    4260
cagtcttcga cctgcgatta taaggatgac gatgacaagt ga                     4302
```

<210> SEQ ID NO 20
<211> LENGTH: 4140
<212> TYPE: DNA
<213> ORGANISM: Rattus norvegicus

```
<400> SEQUENCE: 20
atgaagtctg gctccggagg agggtccccg acctcgctgt gggggctcgt gtttctctcc      60
gccgcgctct cgctctggcc gacgagtgga gaaatttgtg ggcccggcat tgacatccgc     120
aacgactatc agcagctgaa gcgcctggaa aactgcacgg tgatcgaggg cttcctccac     180
atcctgctca tctccaaggc cgaggactac cgaagctacc gcttcccaa gctcacagtc      240 atcaccgagt acttgctgct gtttcgagtg gccggcctcg agagcctggg agacctcttc     300
ccgaacctca cagtcatccg tggctggaaa ctcttctaca attacgcact ggtcatcttc     360
gagatgacca atctcaagga tattgggctt tataatctga ggaacattac tcgggggggcc     420 atcaggattg agaaaaacgc tgacctctgt tacctctcca ccatagactg gtctctcatc     480
ttggatgcgg tgtccaataa ctacattgtg gggaacaagc ccccaaagga atgtggggac     540
ctgtgtccag ggaccttgga ggagaagccc atgtgtgaga agaccaccat caacaatgag     600
tacaactacc gctgctggac cacaaatcgc tgccagaaaa tgtgcccaag tgtgtgtggg     660
aagcgagcct gcaccgagaa caatgagtgc tgccaccccgg agtgcctagg cagctgccac     720
acaccggacg acaacacaac ctgcgtggcc tgccgacact actactacaa aggcgtgtgc     780
gtgcctgcct gcccgcctgg cacctacagg ttcgagggct ggcgctgtgt ggaccgggat     840
ttctgcgcca acatccccaa cgccgagagc agtgactcag atggcttcgt catccacgat     900
ggcgagtgca tgcaggagtg tccatcaggc ttcatccgca acagcaccca gagcatgtac     960
tgtatcccct gtgaaggccc ctgccccaag gtctgcggcg atgaagaaaa gaaaacgaaa    1020
accatcgatt ctgtgacgtc tgcccagatg ctccaagggt gcaccatttt gaagggcaat    1080
ctgcttatta acatccggcg aggcaataac attgcctcgg aattggagaa cttcatgggg    1140
ctcatcgagg tggtgactgg ctacgtgaag atccgccatt ccatgccctt ggtctccttg    1200
tccttcctga agaaccttcg tctcatctta ggagaggagc agctagaagg aaactactcc    1260
ttctatgtcc tggacaacca gaacttgcag cagctgtggg actggaacca ccggaacctg    1320
accgtcaggt cagggaaaat gtacttcgct ttcaatccca agctgtgtgt ctctgaaatt    1380
taccgaatgg aggaggtgac aggaacaaag ggacggcaga gcaaaggaga cataaacacc    1440
aggaacaacg gagagcgagc ttcctgtgaa agtgatgttc tccgtttcac ctccaccacc    1500
acctggaaga accgcatcat cataacgtgg caccggtacc ggccgccgga ctaccgggat    1560
ctcatcagtt tcacagtcta ctacaaggag gcacccttta aaaacgtcac ggaatacgac    1620
gggcaggatg cctgtggctc caacagctgg aacatggtgg acgtggacct gcctccgaac    1680
aaggaggggg agcctggcat tttgctgcat gggctgaagc cctggaccca gtatgcagtc    1740
tatgtcaagg ctgtgacccct caccatggtg gaaaacgacc acatccgtgg ggccaaaagt    1800
gaaatcttgt acattcgcac caacgcttca gttccttcca ttcctctaga tgtcctctcg    1860
gcatcaaact cctcctctca gctgatcgta agtggaacc ccccaactct gcccaatggt    1920
aacttgagtt actacattgt gaggtggcag cggcagccgc aggatggcta tctgttccgg    1980
cacaactact gctccaaaga caaaatacccc atcagaaagt acgccgatgg taccatcgat    2040
gtggaggagg tgacagaaaa tcccaagaca gaagtgtgcg tggtgataaa gggccgtgc    2100 tgtgcctgtc ctaaaaccga agctgagaag caggctgaga aggaggaggc tgagtaccgt    2160
aaagtctttg agaatttcct tcacaactcc atctttgtgc cagacctga gggaggcgg    2220 agagatgtcc tgcaggtggc taacaccacc atgtccagcc gaagcaggaa caccacggta    2280
gctgacacct acaatatcac agaccccgga gagttcgaga cagaatacccc tttctttgag    2340
```

| | |
|---|---|
| agcagagtgg ataacaagga gaggactgtc atttccaacc tccggccttt cactctgtac | 2400 |
| cgtatcgata tccacagctg caaccacgag gctgagaagc tgggctgcag cgcctccaac | 2460 |
| tttgtctttg caagaaccat gccagcagaa ggagcagatg acattcctgg cccagtgacc | 2520 |
| tgggagccaa gacctgaaaa ctccatcttt ttaaagtggc cagaacccga gaaccccaac | 2580 |
| ggattgattc taatgtatga aataaaatac ggatcgcaag tcgaggatca gcgggaatgt | 2640 |
| gtgtccagac aggagtacag gaagtatgga ggggccaaac ttaaccgtct aaacccaggg | 2700 |
| aactatacgg cccggattca ggctacctcc ctctctggga atgggtcgtg gacagatcct | 2760 |
| gtgttcttct atgtcccagc caaaacaacg tatgagaatt tcatgcatct gatcattgct | 2820 |
| ctgccggttg ccatcctgct gattgtgggg ggcctggtaa tcatgctgta tgtcttccat | 2880 |
| agaaagagga ataacagcag attgggcaac ggggtgctgt acgcctctgt gaaccccgag | 2940 |
| tatttcagcg cagctgatgt gtacgtgcct gatgaatggg aggtagctcg ggagaagatc | 3000 |
| accatgaacc gggagctcgg acaagggtcc ttcgggatgg tctatgaagg agtggccaag | 3060 |
| ggcgtggtca aggacgagcc tgaaaccaga gtggccatca gacagtgaa tgaggctgca | 3120 |
| agtatgcgtg agagaattga gtttctcaac gaggcctcag tgatgaagga gttcaactgt | 3180 |
| caccatgtgg tccggttgct gggtgtagta tcccaaggcc agcccaccct ggtcatcatg | 3240 |
| gaactaatga cacgtggcga tctcaaaagt tatctccggt ctctaaggcc agaggtggag | 3300 |
| cagaataatc tagtcctgat tcctccgagc ttaagcaaga tgatccagat ggctggagag | 3360 |
| attgcagatg gcatggccta cctcaatgcc aacaagttcg tccacagaga cctggctgct | 3420 |
| cggaactgca tggtagctga agatttcaca gtcaaaattg gagattttgg tatgacacga | 3480 |
| gacatctacg agacggacta ctaccggaaa ggcgggaagg gcttgctgcc tgtgcgctgg | 3540 |
| atgtctcccg agtccctcaa ggatggcgtc ttcaccactc attccgatgt ctggtccttt | 3600 |
| ggggtcgtcc tctgggagat cgccactctg gctgagcagc cgtaccaggg cctgtccaac | 3660 |
| gagcaagttc ttcgtttcgt catggagggc ggccttctgg acaagccgga taactgcccc | 3720 |
| gatatgctgt ttgaacttat gcgcatgtgc tggcagtaca accccaagat gcggccctcc | 3780 |
| ttcctggaga tcatcggaag catcaaggat gagatggagc ccagtttcca ggaggtctcc | 3840 |
| ttctactaca gcgaggagaa caagcctcca gagccggagg agctggagat ggagctggag | 3900 |
| ctggagcccg agaacatgga gagcgtcccg ctggacccct cggcctcctc agcctccctg | 3960 |
| cctctgcctg aaagacactc aggacacaag gctgagaacg gccctggcgt gctggttctc | 4020 |
| cgtgccagtt ttgatgagag acagccttac gctcacatga atggggacg cgccaacgag | 4080 |
| agggccttgc tctgccccca gtcctcaacc tgcgattata aggatgacga tgacaagtga | 4140 |

<210> SEQ ID NO 21
<211> LENGTH: 4146
<212> TYPE: DNA
<213> ORGANISM: Mus musculus

<400> SEQUENCE: 21

| | |
|---|---|
| atgaagtctg gctccggagg agggtccccg acctcgctgt gggggctcgt gtttctctcc | 60 |
| gccgcgctct ctctctggcc gacgagtgga gaaatctgtg gcccggcat tgacatccgc | 120 |
| aacgactatc agcagctgaa gcgcctggaa aactgcacgg tgatcgaggg cttcctccac | 180 |
| atcctgctca tctccaaggc cgaggactac cgaagctacc gcttccccaa gctcaccgtc | 240 |
| atcactgagt acttgctgct cttccgagtc gctggcctcg agagcctggg agacctcttc | 300 |

```
cccaacctca cagtcatccg tggctggaaa ctcttctaca actacgcact ggtcatcttc      360
gagatgacca atctcaagga tattgggctt tataatctga ggaacattac tcgggggggcc     420 atcaggattg agaagaacgc cgacctctgt tacctctcca ccatagactg gtctctcatc     480
ttggatgcgg tgtccaataa ctacattgtg gggaacaagc ccccgaagga atgtggggac     540
ctgtgtccag ggacattgga ggagaagccc atgtgtgaga agaccaccat caacaatgag     600
tacaactacc gctgctggac cacaaatcgc tgccagaaaa tgtgcccaag tgtgtgcggg     660
aagcgagcct gcaccgagaa caacgagtgc tgccacccgg agtgcctggg cagctgccac     720
acaccggacg acaacacaac ctgcgtggcc tgcagacact actactacaa aggcgtgtgt     780
gtgcctgcct gcccgcctgg cacctacagg ttcgagggct ggcgctgtgt ggatcgcgat     840
ttctgcgcca acatccccaa cgctgagagc agtgactcgg atggcttcgt tatccacgac     900
gatgagtgca tgcaggagtg tccctcaggc ttcatccgca acagcaccca gagcatgtac     960
tgtatcccct gcgaaggccc ctgccccaaa gtctgcggcg atgaagagaa gaaaacgaaa    1020
accatcgatt cggtgacttc tgctcaaatg ctccaaggat gcaccatcct gaagggcaat    1080
ctgcttatta acatccggag aggcaataac attgcctcgg agttggagaa cttcatgggg    1140
ctcatcgagg tggtgaccgg ctacgtgaag atccgccatt ctcatgcctt ggtctccttg    1200
tccttcctga agaaccttcg tctcatctta ggagaggagc agctggaagg gaactactcc    1260
ttctatgtcc tagacaacca gaacttgcag cagctgtggg actggaacca ccggaacctg    1320
accgtcaggt ccggaaagat gtactttgct ttcaatccca agctgtgtgt ctccgaaatt    1380
taccgcatga ggaagtgac cggaaccaag ggacgccaga gcaaagggga cataaacacc    1440
aggaacaacg gagagcgagc ttcctgtgaa agtgatgttc tccgtttcac ctccaccacg    1500
acctggaaga accgaatcat cataacgtgg caccggtacc ggccgccgga ctaccgggat    1560
ctcatcagct tcacagttta ctacaaggag gcaccattta aaaacgttac ggaatatgac    1620
gggcaggatg cctgtggctc caacagctgg aacatggtgg atgtagacct gcctccgaac    1680
aaggagggcg agcctggcat tttactgcat gggctgaagc cctggaccca gtatgctgtc    1740
tatgtcaagg ctgtgacct caccatggtg gaaaacgacc atatccgtgg ggccaaaagt    1800
gaaatcttgt acattcgcac caatgcttca gtcccttcca ttccctaga tgtcctctca    1860 gcatcaaact cttcctctca gctgattgtg aagtggaatc ctccaactct gcccaatggt    1920
aacttgagtt actacattgt gaggtggcag cggcagcccc aggatggtta cctgtaccgg    1980
cacaactact gctccaaaga caaaatacc atcagaaagt acgccgatgg taccatcgac    2040
gtggaggagg tgacggaaaa tcccaagaca gaagtgtgtg gtggtgataa agggccatgc    2100
tgcgcttgcc ctaaaactga agctgagaag caggctgaga aggaggaggc tgagtaccgt    2160
aaagtctttg agaatttcct tcacaattcc atctttgtgc ccaggcccga aggaggcgg    2220 agagacgtca tgcaagtggc caacacgacc atgtccagcc gaagcaggaa caccacggta    2280
gctgacacct acaatatcac agacccggag gagttcgaga cagagtaccc tttctttgag    2340
agcagagtgg ataacaagga gaggactgtc atctccaacc tccggccttt cactctgtac    2400
cgcatcgata tccacagctg caaccacgag gctgagaagc tgggctgcag cgcctccaac    2460
ttcgtctttg cgagaaccat gccagcagaa ggagcagatg atatccctgg tccggtgacc    2520
tgggagccaa gacccgaaaa ctccatcttt ttaaagtggc cagaacccga gaaccccaac    2580
ggattgatcc taatgtatga aattaaatac ggtcgcaag tcgaggatca gcgggaatgt    2640
gtgtccagac aggagtacag gaagtacgga ggggccaaac tcaaccgtct aaacccaggg    2700
```

```
aactatacag cccggattca ggctacctcc ctctctggga atgggtcatg gacagatcct    2760
gtgttcttct atgtccccgc caaaacgacg tatgagaact tcatgcatct gatcattgct    2820
ctgccggttg ccatcctgct gatcgttggg gggctggtta tcatgctgta tgtcttccat    2880
agaaagagaa ataacagcag gttgggcaat ggagtgctgt atgcttctgt gaaccccgag    2940
tatttcagcg cagctgatgt gtacgtgcct gatgaatggg aggtagctcg agagaagatc    3000
accatgaacc gggagctcgg acaagggtcc tttgggatgg tctatgaagg agtggccaag    3060
ggtgtggtca aggatgaacc cgaaaccaga gtggccatca agacggtaaa cgaggctgca    3120
agtatgcgtg aaagaatcga gtttctcaac gaggcctcgg tgatgaagga gttcaattgt    3180
caccatgtgg tccggttgct gggtgtggta tcccaaggcc agcccaccct ggtcatcatg    3240
gaactaatga cacgcggtga tctcaaaagt tatctccggt ctctgaggcc agaagtggag    3300
cagaataatc tagtcctcat tcctccgagc ttaagcaaga tgatccagat ggctggagag    3360
attgcagatg gcatggccta cctcaatgcc aacaagttcg tccacagaga ccttgctgct    3420
aggaactgca tggtagccga agatttcaca gtcaaaattg gagatttcgg tatgacacga    3480
gacatctacg agacggacta ctaccggaaa ggcggggaagg ggttgctgcc tgtgcgctgg    3540
atgtctcccg agtccctcaa ggatggtgtc ttcactactc attctgatgt ctggtccttc    3600
ggggtcgtcc tctgggagat cgccacgctg gctgagcagc cctaccaggg cttgtccaac    3660
gagcaagttc ttcgtttcgt catggagggt ggccttctgg acaagccgga caactgccct    3720
gatatgctgt ttgaacttat gcgcatgtgc tggcagtata ccccaagat gcggccctcc    3780 ttcctggaga tcatcggcag catcaaggat gagatggagc ccagcttcca ggaggtctcc    3840
ttctactaca gcgaggagaa caagcctccc gagccagagg agctggagat ggagctggag    3900
atggagcctg agaacatgga gagcgtccca ctggacccctt cggcctcctc agcctccctg    3960
cctctgcctg aaagacactc aggacacaag gctgagaatg gcccgggccc tggcgtgctc    4020
gttctccgcg ccagttttga tgagagacag ccttacgctc acatgaacgg gggacgcgcc    4080
aacgagaggg ccttgcctct gccccagtcc tcgacctgcg attataagga tgacgatgac    4140
aagtga                                                               4146
```

<210> SEQ ID NO 22
<211> LENGTH: 723
<212> TYPE: DNA
<213> ORGANISM: Artificial Sequence
<220> FEATURE:
<223> OTHER INFORMATION: Synthetic sequence, mock

<400> SEQUENCE: 22

```
atggtgagtg tgattaaacc agagatgaag atcaagctgt gtatgagagg cactgtaaac      60
gggcataatt tcgtgattga aggagaagga aaaggaaatc cttacgaggg aacgcagatt     120
ttagacctga acgtcactga aggcgcacct ctgcctttcg cttacgatat cttgacaaca     180
gtgttccagt acggcaacag ggcattcacc aagtacccag cagatattca ggactatttc     240
aagcagactt ttcctgaggg gtatcactgg gaaagaagca tgacttatga agaccagggc     300
atttgcaccg ccacaagcaa cataagcatg agggggcgact gttttttcta tgacattcgt     360
tttgatggca ccaactttcc tcccaatggt ccggttatgc agaagaagac tcttaaatgg     420
gagccatcca ctgagaaaat gtacgtagag gatggagtgc tgaagggtga tgttaacatg    480
cgcctgttgc ttgaaggagg tggccattat cgatgtgatt tcaaaactac ttacaaagca    540
```

```
aagaaggagg tccgtttgcc agacgcgcac aaaattgacc accgcattga gattttgaag      600
catgacaaag attacaacaa ggtcaagctc tatgagaatg ccgttgctcg ctattctatg      660
ctgccgagtc aggccaagga ttataaggat gacgatgaca agcatcacca ccatcaccac      720
tag                                                                   723

<210> SEQ ID NO 23
<211> LENGTH: 4152
<212> TYPE: DNA
<213> ORGANISM: Artificial Sequence
<220> FEATURE:
<223> OTHER INFORMATION: Synthetic sequence, chimeric receptor

<400> SEQUENCE: 23
atgaagtctg ctccggagg agggtccccg acctcgctgt gggggctcct gtttctctcc       60
gccgcgctct cgctctggcc gacgagtgga gaaatctgcg ggccaggcat cgacatccgc      120
aacgactatc agcagctgaa gcgcctggag aactgcacgg tgatcgaggg ctacctccac      180
atcctgctca tctccaaggc cgaggactac cgcagctacc gcttcccaa gctcacggtc       240 attaccgagt acttgctgct gttccgagtg gctggcctcg agagcctcgg agacctcttc      300
cccaacctca cggtcatccg cggctggaaa ctcttctaca actacgccct ggtcatcttc      360
gagatgacca atctcaagga tattgggctt acaacctga ggaacattac tcgggggcc       420 atcaggattg agaaaaatgc tgacctctgt tacctctcca ctgtggactg gtccctgatc      480
ctggatgcgg tgtccaataa ctacattgtg gggaataagc ccccaaagga atgtggggac      540
ctgtgtccag ggaccatgga ggagaagccg atgtgtgaga agaccaccat caacaatgag      600
tacaactacc gctgctggac cacaaaccgc tgccagaaaa tgtgcccaag cacgtgtggg      660
aagcgggcgt gcaccgagaa caatgagtgc tgccaccccg agtgcctggg cagctgcagc      720
gcgcctgaca cgacacggc ctgtgtagct tgccgccact actactatgc cggtgtctgt      780
gtgcctgcct gccgcgccaa cacctacagg tttgagggct ggcgctgtgt ggaccgtgac      840
ttctgcgcca acatcctcag cgccgagagc agcgactccg aggggtttgt gatccacgac      900
ggcgagtgca tgcaggagtg cccctcgggc ttcatccgca cggcagcca gagcatgtac      960 tgcatcccct tgtgaaggtcc ttgcccgaag gtctgtgagg aagaaaagaa aacaaagacc     1020
attgattctg ttacttctgc tcagatgctc aaggatgca ccatcttcaa gggcaatttg      1080
ctcattaaca tccgacgggg gaataacatt gcttcagagc tggagaactt catggggctc     1140
atcgaggtgg tgacgggcta cgtgaagatc cgccattctc atgccttggt ctccttgtcc     1200
ttcctaaaaa accttcgcct catcctagga gaggagcagc tagaagggaa ttactccttc     1260
tacgtcctcg acaaccagaa cttgcagcaa ctgtgggact gggaccaccg caacctgacc     1320
atcaaagcag ggaaaatgta ctttgctttc aatcccaaat tatgtgtttc gaaatttac     1380 cgcatggagg aagtgacggg gactaaaggg cgccaaagca aggggacat aaacaccagg     1440 aacaacgggg agagagcctc ctgtgaaagt gacttactta atttctctta cattcggaca    1500
tcttttgaca agatcttgct gagatgggag ccgtactggc cccccgactt ccgagacctc    1560
ttggggttca gctgttcta caagagcc cctatcaga atgtgacgga gttcgacggg       1620
caggatgcgt gtggttccaa cagttggacg gtggtagaca ttgacccacc cctgaggtcc    1680
aacgacccca aatcacagaa ccacccaggg tggctgatgc gggtctcaa gcctggaccc    1740 cagtatgcca tcttgtgaa gacccctggtc accttcgg atgaacgccg gacctatggg    1800
gccaagagtg acatcattta tgtccagaca gatgccacca cccctctgt gcccctggat    1860
```

```
ccaatctcag tgtctaactc atcatcccag attattctga agtggaaacc accctccgac    1920
cccaatggca acatcaccca ctacctggtt ttctgggaga ggcaggcgga agacagtgag    1980
ctgttcgagc tggattattg cctcaaaggg ctgaagctgc cctcgaggac ctggtctcca    2040
ccattcgagt ctgaagattc tcagaagcac aaccagagtg agtatgagga ttcggccggc    2100
gaatgctgct cctgtccaaa gacagactct cagatcctga aggagctgga ggagtcctcg    2160
tttaggaaga cgtttgagga ttacctgcac aacgtggttt tcgtcccag aaaaacctct     2220 tcaggcactg gtgccgagga ccctaggcca tctcggaaac gcaggtccct tggcgatgtt    2280
gggaatgtga cggtggccgt gcccacggtg gcagctttcc ccaacacttc ctcgaccagc    2340
gtgcccacga gtccggagga gcacaggcct tttgagaagg tggtgaacaa ggagtcgctg    2400
gtcatctccg gcttgcgaca cttcacgggc tatcgcatcg agctgcaggc ttgcaaccag    2460
gacacccctg aggaacggtg cagtgtggca gcctacgtca gtgcgaggac catgcctgaa    2520
gccaaggctg atgacattgt tggccctgtg acgcatgaaa tctttgagaa caacgtcgtc    2580
cacttgatgt ggcaggagcc gaaggagccc aatggtctga tcgtgctgta tgaagtgagt    2640
tatcggcgat atggtgatga ggagctgcat ctctgcgtct cccgcaagca cttcgctctg    2700
gaacggggct gcaggctgcg tgggctgtca ccggggaact acagcgtgcg aatccgggcc    2760
acctcccttg cggcaacgg ctcttggacg gaacccacct atttctacgt gacagactat     2820
ttagacgtcc cgtcaaatat tgcaaaaatt atcatcggcc ccctcatctt tgtctttctc    2880
ttcagtgttg tgattggaag tatttatcta ttcctgagaa agaggcagcc agatgggccg    2940
ctgggaccgc tttacgcttc ttcaaaccct gagtatctca gtgccagtga tgtgtttcca    3000
tgctctgtgt acgtgccgga cgagtgggag gtgtctcgag agaagatcac cctccttcga    3060
gagctggggc agggctcctt cggcatggtg tatgagggca atgccaggga catcatcaag    3120
ggtgaggcag agacccgcgt ggcggtgaag acggtcaacg agtcagccag tctccgagag    3180
cggattgagt tcctcaatga ggcctcggtc atgaagggct tcacctgcca tcacgtggtg    3240
cgcctcctgg gagtggtgtc caagggccag cccacgctgg tggtgatgga gctgatggct    3300
cacggagacc tgaagagcta cctccgttct ctgcggccag aggctgagaa taatcctggc    3360
cgccctcccc ctaccttca agagatgatt cagatggcgg cagagattgc tgacgggatg     3420
gcctacctga acgccaagaa gtttgtgcat cgggacctgg cagcgagaaa ctgcatggtc    3480
gcccatgatt ttactgtcaa aattggagac tttggaatga ccagagacat ctatgaaacg    3540
gattactacc ggaaagggg caagggtctg ctccctgtac ggtggatggc accggagtcc     3600
ctgaaggatg gggtcttcac cacttcttct gacatgtggt cctttggcgt ggtcctttgg    3660
gaaatcacca gcttggcaga acagccttac caaggcctgt ctaatgaaca ggtgttgaaa    3720
tttgtcatgg atggagggta tctggatcaa cccgacaact gtccagagag agtcactgac    3780
ctcatgcgca tgtgctggca attcaacccc aagatgaggc caaccttcct ggagattgtc    3840
aacctgctca aggacgacct gcaccccagc tttccagagg tgtcgttctt ccacagcgag    3900
gagaacaagg ctcccgagag tgaggagctg gagatggagt tgaggacat ggagaatgtg     3960 cccctggacc gttcctcgca ctgtcagagg gaggaggcgg ggggccggga tggagggtcc    4020
tcgctgggtt tcaagcggag ctacgaggaa cacatcccctt acacacacat gaacggaggc   4080
aagaaaaacg ggcggattct gaccttgcct cggtccaatc cttccgatta taaggatgac    4140
gatgacaagt ga                                                        4152
```

<210> SEQ ID NO 24
<211> LENGTH: 4149
<212> TYPE: DNA
<213> ORGANISM: Artificial Sequence
<220> FEATURE:
<223> OTHER INFORMATION: Synthetic sequence, chimeric receptor

<400> SEQUENCE: 24

| | | | | | |
|---|---|---|---|---|---|
| atggccaccg | ggggccggcg | gggggcggct | gccgcgccgc | tgctggtggc | ggtggccgcg | 60 |
| ctgctactgg | gcgccgcggg | ccacctgtac | cccggagagg | tgtgtcccgg | catggatatc | 120 |
| cggaacaacc | tcactaggtt | gcatgagctg | gagaattgct | ctgtcatcga | aggacacttg | 180 |
| cagatactct | tgatgttcaa | aacgaggccc | gaagatttcc | gagacctcag | tttccccaaa | 240 |
| ctcatcatga | tcactgatta | cttgctgctc | ttccgggtct | atgggctcga | gagcctgaag | 300 |
| gacctgttcc | caacctcac | ggtcatccgg | ggatcacgac | tgttctttaa | ctacgcgctg | 360 |
| gtcatcttcg | agatggttca | cctcaaggaa | ctcggcctct | acaacctgat | gaacatcacc | 420 |
| cggggttctg | tccgcatcga | aagaacaat | gagctctgtt | acttggccac | tatcgactgg | 480 |
| tcccgtatcc | tggattccgt | ggaggataat | tacatcgtgt | tgaacaaaga | tgacaacgag | 540 |
| gagtgtggag | acatctgtcc | gggtaccgcg | aagggcaaga | ccaactgccc | cgccaccgtc | 600 |
| atcaacggc | agtttgtcga | acgatgttgg | actcatagtc | actgccagaa | agtttgcccg | 660 |
| accatctgta | agtcacacgg | ctgcaccgcc | gaaggcctct | gttgccacag | cgagtgcctg | 720 |
| ggcaactgtt | ctcagcccga | cgaccccacc | aagtgcgtgg | cctgccgcaa | cttctacctg | 780 |
| gacggcaggt | gtgtggagac | ctgccgccc | ccgtactacc | acttccagga | ctggcgctgt | 840 |
| gtgaacttca | gcttctgcca | ggacctgcac | acaaatgca | agaactcgcg | gaggcagggc | 900 |
| tgccaccagt | acgtcattca | aacaacaag | tgcatccctg | agtgtcctc | cgggtacacg | 960 |
| atgaattcca | gcaacttgct | gtgcaccca | tgcctgggtc | cctgtcccaa | ggtgtgccac | 1020 |
| ctcctagaag | gcgagaagac | catcgactcg | gtgacgtctg | cccaggagct | ccgaggatgc | 1080 |
| accgtcatca | acgggagtct | gatcatcaac | attcgaggag | gcaacaatct | ggcagctgag | 1140 |
| ctagaagcca | acctcggcct | cattgaagaa | atttcagggt | atctaaaaat | ccgccgatcc | 1200 |
| tacgctctgg | tgtcactttc | cttcttccgg | aagttacgtc | tgattcgagg | agagaccttg | 1260 |
| gaaattggga | actactcctt | ctatgccttg | gacaaccaga | acctaaggca | gctctgggac | 1320 |
| tggagcaaac | acaacctcac | catcactcag | ggaaactct | tcttccacta | taaccccaaa | 1380 |
| ctctgcttgt | cagaaatcca | aagatgaa | gaagtttcag | gaaccaaggg | gcgccaggag | 1440 |
| agaaacgaca | ttgccctgaa | gaccaatggg | gaccaggcat | cctgtgaaaa | tgaggtcctg | 1500 |
| catttcacct | ccaccaccac | gtcgaagaat | cgcatcatca | taacctggca | ccggtaccgg | 1560 |
| cccctgact | acagggatct | catcagcttc | accgtttact | acaaggaagc | ccctttaag | 1620 |
| aatgtcacag | agtatgatgg | gcaggatgcc | tgcggctcca | cagctggaa | catggtggac | 1680 |
| gtggacctcc | cgcccaacaa | ggacgtggag | cccggcatct | tactacatgg | gctgaagccc | 1740 |
| tggactcagt | acgccgttta | cgtcaaggct | gtgacccctca | ccatggtgga | aacgaccat | 1800 |
| atccgtgggg | ccaagagtga | gatcttgtac | attcgcacca | tgcttcagt | tccttccatt | 1860 |
| cccttggacg | ttctttcagc | atcgaactcc | tcttctcagt | taatcgtgaa | gtggaaccct | 1920 |
| ccctctctgc | ccaacggcaa | cctgagttac | tacattgtgc | gctggcagcg | gcagcctcag | 1980 |
| gacggctacc | tttaccggca | caattactgc | tccaaagaca | aaatcccat | caggaagtat | 2040 |
| gccgacggca | ccatcgacat | tgaggaggtc | acagagaacc | ccaagactga | ggtgtgtggt | 2100 |

```
ggggagaaag ggccttgctg cgcctgcccc aaaactgaag ccgagaagca ggccgagaag    2160
gaggaggctg aataccgcaa agtctttgag aatttcctgc acaactccat cttcgtgccc    2220
agacctgaaa ggaagcggag agatgtcatg caagtggcca acaccaccat gtccagccga    2280
agcaggaaca ccacggccgc agacacctac aacatcaccg acccggaaga gctggagaca    2340
gagtacccct tctttgagag cagagtggat aacaaggaga gaactgtcat ttctaacctt    2400
cggcctttca cattgtaccg catcgatatc cacagctgca accacgaggc tgagaagctg    2460
ggctgcagcg cctccaactt cgtctttgca aggactatgc ccgcagaagg agcagatgac    2520
attcctgggc cagtgacctg ggagccaagg cctgaaaact ccatcttttt aaagtggccg    2580
gaacctgaga atcccaatgg attgattcta atgtatgaaa taaaatacgg atcacaagtt    2640
gaggatcagc gagaatgtgt gtccagacag gaatacagga agtatggagg ggccaagcta    2700
aaccggctaa acccggggaa ctacacagcc cggattcagg ccacatctct ctctgggaat    2760
gggtcgtgga cagatcctgt gttcttctat gtccaggcca aaacaggata tgaaaacttc    2820
atccatctga tcatcgctct gcccgtcgct gtcctgttga tcgtgggagg gttggtgatt    2880
atgctgtacg tcttccatag aaagagaaat aacagcaggc tggggaatgg agtgctgtat    2940
gcctctgtga acccggagta cttcagcgct gctgatgtgt acgttcctga tgagtgggag    3000
gtggctcggg agaagatcac catgagccgg aacttgggc aggggtcgtt tgggatggtc    3060
tatgaaggag ttgccaaggg tgtggtgaaa gatgaacctg aaaccagagt ggccattaaa    3120
acagtgaacg aggccgcaag catgcgtgaa aggattgagt ttctcaacga agcttctgtg    3180
atgaaggagt tcaattgtca ccatgtggtg cgattgctgg gtgtggtgtc ccaaggccag    3240
ccaacactgg tcatcatgga actgatgaca cggggcgatc tcaaaagtta tctccggtct    3300
ctgaggccag aaatggagaa taatccagtc ctagcacctc aagcctgag caagatgatt    3360 cagatggccg agagattgc agacggcatg gcatacctca cgccaataa gttcgtccac    3420 agagaccttg ctgcccggaa ttgcatggta gccgaagatt tcacagtcaa aatcggagat    3480
tttggtatga cgcgagatat ctatgagaca gactattacc ggaaaggagg gaaagggctg    3540
ctgcccgtgc gctggatgtc tcctgagtcc ctcaaggatg gagtcttcac cacttactcg    3600
gacgtctggt ccttcggggt cgtcctctgg gagatcgcca cactggccga gcagccctac    3660
cagggcttgt ccaacgagca agtccttcgc ttcgtcatgg agggcggcct tctgacaag    3720 ccagacaact gtcctgacat gctgtttgaa ctgatgcgca tgtgctggca gtataacccc    3780
aagatgaggc cttccttcct ggagatcatc agcagcatca agaggagat ggagcctggc    3840 ttccgggagg tctccttcta ctacagcgag gagaacaagc tgcccgagcc ggaggagctg    3900
gacctggagc cagagaacat ggagagcgtc cccctggacc cctcggcctc ctcgtcctcc    3960
ctgccactgc ccgacagaca ctcaggacac aaggccgaga acggccccgg ccctggggtg    4020
ctggtcctcc gcgccagctt cgacgagaga cagccttacg cccacatgaa cgggggccgc    4080
aagaacgagc gggccttgcc gctgccccag tcttcgacct gcgattataa ggatgatgac    4140
gataagtga                                                           4149
```

<210> SEQ ID NO 25
<211> LENGTH: 4140
<212> TYPE: DNA
<213> ORGANISM: Artificial Sequence
<220> FEATURE:
<223> OTHER INFORMATION: Synthetic sequence, chimeric receptor

<400> SEQUENCE: 25

```
atggccaccg ggggccggcg gggggcggct gccgcgccgc tgctggtggc ggtggccgcg      60
ctgctactgg gcgccgcggg ccacctgtac cccggagagg tgtgtcccgg catggatatc     120
cggaacaacc tcactaggtt gcatgagctg gagaattgct ctgtcatcga aggacacttg     180
cagatactct tgatgttcaa aacgaggccc gaagatttcc gagacctcag tttccccaaa     240
ctcatcatga tcactgatta cttgctgctc ttccgggtct atgggctcga gagcctgaag     300
gacctgttcc ccaacctcac ggtcatccgg ggatcacgac tgttctttaa ctacgcgctg     360
gtcatcttcg agatggttca cctcaaggaa ctcggcctct acaacctgat gaacatcacc     420
cggggttctg tccgcatcga gaagaacaat gagctctgtt acttggccac tatcgactgg     480
tcccgtatcc tggattccgt ggaggataat tacatcgtgt tgaacaaaga tgacaacgag     540
gagtgtgggg acctgtgtcc agggaccatg gaggagaagc cgatgtgtga aagaccacc      600
atcaacaatg agtacaacta ccgctgctgg accacaaacc gctgccagaa aatgtgccca     660
agcacgtgtg ggaagcgggc gtgcaccgag aacaatgagt gctgccaccc cgagtgcctg     720
ggcagctgca gcgcgcctga caacgacacg gcctgtgtag cttgccgcca ctactactat     780
gccggtgtct gtgtgcctgc ctgcccgccc aacacctaca ggtttgaggg ctggcgctgt     840
gtggaccgtg acttctgcgc caacatcctc agcgccgaga gcagcgactc cgaggggttt     900
gtgatccacg acggcgagtg catgcaggag tgccctcgg gcttcatccg caacggcagc     960
cagagcatgt actgcatccc ttgtgaaggt ccttgcccga aggtctgtga ggaagaaaag    1020
aaaacaaaga ccattgattc tgttacttct gctcagatgc tccaaggatg caccatcttc    1080
aagggcaatt tgctcattaa catccgacgg gggaataaca ttgcttcaga gctggagaac    1140
ttcatggggc tcatcgaggt ggtgacgggc tacgtgaaga tccgccattc tcatgccttg    1200
gtctccttgt ccttcctaaa aaaccttcgc ctcatcctag agaggagca gctagaaggg    1260
aattactcct tctacgtcct cgacaaccag aacttgcagc aactgtggga ctgggaccac    1320
cgcaacctga ccatcaaagc agggaaaatg tactttgctt tcaatcccaa attatgtgtt    1380
tccgaaattt accgcatgga ggaagtgacg gggactaaag ggcgccaaag caaaggggac    1440
ataaacacca ggaacaacgg ggagagagcc tcctgtgaaa gtgacgtcct gcatttcacc    1500
tccaccacca cgtcgaagaa tcgcatcatc ataacctggc accggtaccg gcccctgac     1560
tacagggatc tcatcagctt caccgtttac tacaaggaag cacccttaa gaatgtcaca    1620
gagtatgatg ggcaggatgc ctgcggctcc aacagctgga acatggtgga cgtggacctc    1680
ccgcccaaca aggacgtgga gcccggcatc ttactacatg ggctgaagcc ctggactcag    1740
tacgccgttt acgtcaaggc tgtgacctc accatggtgg agaacgacca tatccgtggg    1800
gccaagagtg agatcttgta cattcgcacc aatgcttcag ttccttccat tcccttggac    1860
gttctttcag catcgaactc ctcttctcag ttaatcgtga agtggaaccc tccctctctg    1920
cccaacggca acctgagtta ctacattgtg cgctggcagc ggcagcctca ggacggctac    1980
ctttaccggc acaattactg ctccaaagac aaaatcccca tcaggaagta tgccgacggc    2040
accatcgaca ttgaggaggt cacagagaac cccaagactg aggtgtgtgg tgggagaaa     2100
gggccttgct gcgcctgccc caaaactgaa gccgagaagc aggccgagaa ggaggaggct    2160
gaataccgca aagtctttga gaatttcctg cacaactcca tcttcgtgcc cagacctgaa    2220
aggaagcgga gagatgtcat gcaagtggcc aacaccacca tgtccagccg aagcaggaac    2280
accacggccg cagacaccta caacatcacc gacccggaag agctggagac agagtaccct    2340
```

```
ttctttgaga gcagagtgga taacaaggag agaactgtca tttctaacct tcggcctttc    2400
acattgtacc gcatcgatat ccacagctgc aaccacgagg ctgagaagct gggctgcagc    2460
gcctccaact tcgtctttgc aaggactatg cccgcagaag gagcagatga cattcctggg    2520
ccagtgacct gggagccaag gcctgaaaac tccatctttt taaagtggcc ggaacctgag    2580
aatcccaatg gattgattct aatgtatgaa ataaaatacg gatcacaagt tgaggatcag    2640
cgagaatgtg tgtccagaca ggaatacagg aagtatggag gggccaagct aaaccggcta    2700
aacccgggga actacacagc ccggattcag gccacatctc tctctgggaa tgggtcgtgg    2760
acagatcctg tgttcttcta tgtccaggcc aaaacaggat atgaaaactt catccatctg    2820
atcatcgctc tgcccgtcgc tgtcctgttg atcgtgggag ggttggtgat tatgctgtac    2880
gtcttccata gaaagagaaa taacagcagg ctggggaatg gagtgctgta tgcctctgtg    2940
aacccggagt acttcagcgc tgctgatgtg tacgttcctg atgagtggga ggtggctcgg    3000
gagaagatca ccatgagccg ggaacttggg caggggtcgt ttgggatggt ctatgaagga    3060
gttgccaagg gtgtggtgaa agatgaacct gaaaccagag tggccattaa acagtgaac    3120 gaggccgcaa gcatgcgtga aaggattgag tttctcaacg aagcttctgt gatgaaggag    3180
ttcaattgtc accatgtggt gcgattgctg ggtgtggtgt cccaaggcca gccaacactg    3240
gtcatcatgg aactgatgac acggggcgat ctcaaaagtt atctccggtc tctgaggcca    3300
gaaatggaga ataatccagt cctagcacct ccaagcctga gcaagatgat tcagatggcc    3360
ggagagattg cagacggcat ggcatacctc aacgccaata agttcgtcca cagagacctt    3420
gctgcccgga attgcatggt agccgaagat ttcacagtca aaatcggaga ttttggtatg    3480
acgcgagata tctatgagac agactattac cggaaaggag ggaaagggct gctgcccgtg    3540
cgctggatgt ctcctgagtc cctcaaggat ggagtcttca ccacttactc ggacgtctgg    3600
tccttcgggg tcgtcctctg ggagatcgcc acactggccg agcagcccta ccagggcttg    3660
tccaacgagc aagtccttcg cttcgtcatg gagggcggcc ttctggacaa gccagacaac    3720
tgtcctgaca tgctgtttga actgatgcgc atgtgctggc agtataaccc caagatgagg    3780
ccttccttcc tggagatcat cagcagcatc aaagaggaga tggagcctgg cttccggagg    3840
gtctccttct actacagcga ggagaacaag ctgcccgagc cggaggagct ggacctggag    3900
ccagagaaca tggagagcgt ccccctggac ccctcggcct cctcgtcctc cctgccactg    3960
cccgacagac actcaggaca caaggccgag aacggccccg gccctggggt gctggtcctc    4020
cgcgccagct tcgacgagag acagccttac gcccacatga cgggggccg caagaacgag    4080 cgggccttgc cgctgccccc agtcttcgac ctgcgattata aggatgacga tgacaagtga    4140
```

<210> SEQ ID NO 26
<211> LENGTH: 4128
<212> TYPE: DNA
<213> ORGANISM: Artificial Sequence
<220> FEATURE:
<223> OTHER INFORMATION: Synthetic sequence, chimeric receptor

<400> SEQUENCE: 26

```
atgaagtctg gctccggagg agggtccccg acctcgctgt gggggctcct gtttctctcc      60
gccgcgctct cgctctggcc gacgagtgga gaaatctgcg ggccaggcat cgacatccgc     120
aacgactatc agcagctgaa gcgcctggag aactgcacgg tgatcgaggg ctacctccac     180
atcctgctca tctccaaggc cgaggactac cgcagctacc gcttccccaa gctcacggtc     240
```

```
attaccgagt acttgctgct gttccgagtg gctggcctcg agagcctcgg agacctcttc    300
cccaacctca cggtcatccg cggctggaaa ctcttctaca actacgccct ggtcatcttc    360
gagatgacca atctcaagga tattgggctt tacaacctga ggaacattac tcgggggcc     420 atcaggattg agaaaaatgc tgacctctgt tacctctcca ctgtggactg gtccctgatc    480
ctggatgcgg tgtccaataa ctacattgtg gggaataagc ccccaaagga atgtggggac    540
ctgtgtccag ggaccatgga ggagaagccg atgtgtgaga agaccaccat caacaatgag    600
tacaactacc gctgctggac cacaaaccgc tgccagaaaa tgtgcccaag cacgtgtggg    660
aagcgggcgt gcaccgagaa caatgagtgc tgccaccccg agtgcctggg cagctgcagc    720
gcgcctgaca acgacacggc ctgtgtagct tgccgccact actactatgc cggtgtctgt    780
gtgcctgcct gcccgcccaa cacctacagg tttgagggct ggcgctgtgt ggaccgtgac    840
ttctgcgcca acatcctcag cgccgagagc agcgactccg aggggtttgt gatccacgac    900
ggcgagtgca tgcaggagtg cccctcgggc ttcatccgca acggcagcca gagcatgtac    960
tgcatcccct tgtgaaggtcc ttgccccaag gtgtgccacc tcctagaagg cgagaagacc   1020
atcgactcgg tgacgtctgc ccaggagctc cgaggatgca ccgtcatcaa cgggagtctg    1080
atcatcaaca ttcgaggagg caacaatctg gcagctgagc tagaagccaa cctcggcctc    1140
attgaagaaa tttcagggta tctaaaaatc cgccgatcct acgctctggt gtcactttcc    1200
ttcttccgga agttacgtct gattcgagga gagaccttgg aaattgggaa ctactccttc    1260
tatgccttgg acaaccagaa cctaaggcag ctctgggact ggagcaaaca caacctcacc    1320
atcactcagg ggaaactctt cttccactat aaccccaaac tctgcttgtc agaaatccac    1380
aagatggaag aagtttcagg aaccaagggg cgccaggaga gaaacgacat tgccctgaag    1440
accaatgggg accaggcatc ctgtgaaaat gaggtcctgc atttcacctc caccaccacg    1500
tcgaagaatc gcatcatcat aacctggcac cggtaccggc cccctgacta cagggatctc    1560
atcagcttca ccgtttacta caaggaagca cccttaagaa atgtcacaga gtatgatggg    1620
caggatgcct gcggctccaa cagctggaac atggtggacg tggacctccc gcccaacaag    1680
gacgtggagc ccggcatctt actacatggg ctgaagccct ggactcagta cgccgtttac    1740
gtcaaggctg tgaccctcac catggtggag aacgaccata tccgtggggc caagagtgag    1800
atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
```

-continued

| | |
|---|---:|
| tccagacagg aatacaggaa gtatggaggg gccaagctaa accggctaaa cccggggaac | 2700 |
| tacacagccc ggattcaggc cacatctctc tctgggaatg ggtcgtggac agatcctgtg | 2760 |
| ttcttctatg tccaggccaa aacaggatat gaaaacttca tccatctgat catcgctctg | 2820 |
| cccgtcgctg tcctgttgat cgtgggaggg ttggtgatta tgctgtacgt cttccataga | 2880 |
| aagagaaata acagcaggct ggggaatgga gtgctgtatg cctctgtgaa cccggagtac | 2940 |
| ttcagcgctg ctgatgtgta cgttcctgat gagtgggagg tggctcggga gaagatcacc | 3000 |
| atgagccggg aacttgggca ggggtcgttt ggatggtct atgaaggagt tgccaagggt | 3060 |
| gtggtgaaag atgaacctga aaccagagtg gccattaaaa cagtgaacga ggccgcaagc | 3120 |
| atgcgtgaaa ggattgagtt tctcaacgaa gcttctgtga tgaaggagtt caattgtcac | 3180 |
| catgtggtgc gattgctggg tgtggtgtcc caaggccagc caacactggt catcatggaa | 3240 |
| ctgatgacac ggggcgatct caaaagttat ctccggtctc tgaggccaga aatggagaat | 3300 |
| aatccagtcc tagcacctcc aagcctgagc aagatgattc agatggccgg agagattgca | 3360 |
| gacggcatgg catacctcaa cgccaataag ttcgtccaca gagaccttgc tgcccggaat | 3420 |
| tgcatggtag ccgaagattt cacagtcaaa atcggagatt ttggtatgac gcagatatc | 3480 |
| tatgagacag actattaccg gaaggagggg aaagggctgc tgcccgtgcg ctggatgtct | 3540 |
| cctgagtccc tcaaggatgg agtcttcacc acttactcgg acgtctggtc cttcggggtc | 3600 |
| gtcctctggg agatcgccac actggccgag cagccctacc agggcttgtc caacgagcaa | 3660 |
| gtccttcgct tcgtcatgga gggcggcctt ctggacaagc cagacaactg tcctgacatg | 3720 |
| ctgtttgaac tgatgcgcat gtgctggcag tataacccca agatgaggcc ttccttcctg | 3780 |
| gagatcatca gcagcatcaa agaggagatg gagcctggct ccggggaggt ctccttctac | 3840 |
| tacagcgagg agaacaagct gccccgagccg gaggagctgg acctggagcc agagaacatg | 3900 |
| gagagcgtcc ccctggaccc ctcggcctcc tcgtcctccc tgccactgcc cgacagacac | 3960 |
| tcaggacaca aggccgagaa cggccccggc cctggggtgc tggtcctccg cgccagcttc | 4020 |
| gacgagagac agcctacgc ccacatgaac gggggccgca agaacgagcg ggccttgccg | 4080 |
| ctgccccagt cttcgacctg cgattataag gatgacgatg acaagtga | 4128 |

<210> SEQ ID NO 27
<211> LENGTH: 705
<212> TYPE: DNA
<213> ORGANISM: Mus musculus

<400> SEQUENCE: 27

| | |
|---|---:|
| atgaaactcc ttgctgagct cctggggctg ctgctgttct gcttttagg tgtgagatgt | 60 |
| gacatccaga tgaaccagtc tccatccagt ctgtctgcat ccctcggaga cacaattacc | 120 |
| atcacttgcc gtgccagtca gaacattaat ttttggttaa gctggtgcca gcagaaacca | 180 |
| ggaaatattc ctaaactatt gatctataag gcttccaact tgcacacagg cgtcccatca | 240 |
| aggtttagtg gcagtggatc tggaacagat ttcacattaa ccatcagcag tctgcagcct | 300 |
| gaagacattg ccacttacta ctgtctacag ggtcaaagtt atccgtacac gttcggaggg | 360 |
| gggaccaagc tggaaataaa acgggctgat gctgcaccaa ctgtatccat cttcccacca | 420 |
| tccagtgagc agttaacatc tggaggtgcc tcagtcgtgt gcttcttgaa caacttctac | 480 |
| cccaaagaca tcaatgtcaa gtggaagatt gatggcagtg aacgacaaaa tggcgtcctg | 540 |
| aacagttgga ctgatcagga cagcaaagac agcacctaca gcatgagcag caccctcacg | 600 |

```
ttgaccaagg acgagtatga acgacataac agctatacct gtgaggccac tcacaagaca      660
tcaacttcac ccattgtcaa gagcttcaac aggaatgagt gttag                     705
```

<210> SEQ ID NO 28
<211> LENGTH: 234
<212> TYPE: PRT
<213> ORGANISM: Mus musculus

<400> SEQUENCE: 28

```
Met Lys Leu Leu Ala Glu Leu Leu Gly Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys Arg Ala Ser Gln Asn
        35                  40                  45

Ile Asn Phe Trp Leu Ser Trp Cys Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Ile Ala Thr Tyr Tyr Cys Leu Gln Gly Gln
            100                 105                 110

Ser Tyr Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 29
<211> LENGTH: 1383
<212> TYPE: DNA
<213> ORGANISM: Mus musculus

<400> SEQUENCE: 29

```
atgggatgga gctatatcat cctcttttg gtagcaacag ttacagatgt ccactcccag       60
atccaactgc agcagcctgg ggctgagctt gtgaagcctg ggcttcagt gaagttgtcc      120 tgcaaggctc ccggctacac cttcaccagc tattggatgc actgggtgaa gcagaggcct    180
ggacaaggcc ttgagtggat tggagagact aatcctagca atagtgttac taactacaat    240
gagaagttca gagcaaggc cacactgact gtagacaaat cctccagcac agcctacatg    300
caactcagca gcctgacatc tgaggactct gcggtctatt actgtacaat agggagggga    360
cggggatttg cttactgggg ccaagggact ctggtcactg tctctgcagc caaaacgaca    420
```

```
cccccatctg tctatccact ggcccctgga tctgctgccc aaactaactc catggtgacc    480
ctgggatgcc tggtcaaggg ctatttccct gagccagtga cagtgacctg gaactctgga    540
tccctgtcca gcggtgtgca caccttccca gctgtcctgc agtctgacct ctacactctg    600
agcagctcag tgactgtccc ctccagcacc tggcccagcg agaccgtcac ctgcaacgtt    660
gcccacccgg ccagcagcac caaggtggac aagaaaattg tgcccaggga ttgtggttgt    720
aagccttgca tatgtacagt cccagaagta tcatctgtct tcatcttccc cccaaagccc    780
aaggatgtgc tcaccattac tctgactcct aaggtcacgt gtgttgtggt agacatcagc    840
aaggatgatc ccgaggtcca gttcagctgg tttgtagatg atgtggaggt gcacacagct    900
cagacgcaac cccgggagga gcagttcaac agcactttcc gctcagtcag tgaacttccc    960
atcatgcacc aggactggct caatggcaag gagttcaaat gcagggtcaa cagtgcagct   1020
ttccctgccc ccatcgagaa aaccatctcc aaaaccaaag gcagaccgaa ggctccacag   1080
gtgtacacca ttccacctcc caaggagcag atggccaagg ataaagtcag tctgacctgc   1140
atgataacag acttcttccc tgaagacatt actgtggagt ggcagtggaa tgcgcagcca   1200
gcggagaact acaagaacac tcagcccatc atggacacag atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
tga                                                                 1383
```

<210> SEQ ID NO 30
<211> LENGTH: 460
<212> TYPE: PRT
<213> ORGANISM: Mus musculus

<400> SEQUENCE: 30

```
Met Gly Trp Ser Tyr Ile Ile Leu Phe Leu Val Ala Thr Val Thr Asp
1               5                   10                  15

Val His Ser Gln Ile Gln Leu Gln Gln Pro Gly Ala Glu Leu Val Lys
            20                  25                  30

Pro Gly Ala Ser Val Lys Leu Ser Cys Lys Ala Pro Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Thr Asn Pro Ser Asn Ser Val Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Ile Gly Arg Gly Arg Gly Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
```

```
                195                 200                 205
Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Ala Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 31
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: Xaa is Gly or Ser
<220> FEATURE:
<221> NAME/KEY: MISC_FEATURE
<222> LOCATION: (9)..(9)
<223> OTHER INFORMATION: Xaa is Ser or Thr

<400> SEQUENCE: 31

Pro Ser Gly Phe Ile Arg Asn Xaa Xaa Gln Ser Met
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic sequence
```

```
<400> SEQUENCE: 32

Pro Ser Gly Phe Ile Arg Asn Gly Ser Gln Ser Met
1               5                   10

<210> SEQ ID NO 33
<211> LENGTH: 25
<212> TYPE: DNA
<213> ORGANISM: Artificial Sequence
<220> FEATURE:
<223> OTHER INFORMATION: Synthetic sequence

<400> SEQUENCE: 33
ggtgaagttg atgtcttgtg agtgg                                         25

<210> SEQ ID NO 34
<211> LENGTH: 25
<212> TYPE: DNA
<213> ORGANISM: Artificial Sequence
<220> FEATURE:
<223> OTHER INFORMATION: Synthetic sequence

<400> SEQUENCE: 34
gctcttctca gtatggtggt tgtgc                                         25

<210> SEQ ID NO 35
<211> LENGTH: 8
<212> TYPE: PRT
<213> ORGANISM: Artificial Sequence
<220> FEATURE:
<223> OTHER INFORMATION: Synthetic sequence

<400> SEQUENCE: 35

Asp Tyr Lys Asp Asp Asp Asp Lys
1               5
```

ANTI-IGF-I RECEPTOR ANTIBODIES, ENCODING NUCLEIC ACID MOLECULES AND METHODS OF USING SAID ANTIBODIES

CROSS REFERENCE TO RELATED APPLICATIONS

This application is a National Stage of International Application No. PCT/JP2018/020581 filed May 29, 2018, claiming priority based on Japanese Patent Application No. 2017-106529 filed May 30, 2017.

FIELD

The present invention relates to an anti-IGF-I receptor antibody and, more specifically, to an anti-IGF-I receptor antibody which specifically binds to an IGF-I receptor of a vertebrate.

BACKGROUND

1. IGF-I

IGF-I is an insulin-like growth factor secreted mainly from the liver, and affects an IGF-I receptor to thereby express a variety of physiological functions in various organs. Because of this, IGF-I is expected to be used for the treatment of a variety of diseases. Since the amino acid sequence of IGF-I has a high similarity of about 40% to that of proinsulin, IGF-I can bind to an insulin receptor and thereby express insulin-like effects (Non-Patent Literature 1). In addition, since the amino acid sequence of the IGF-I receptor has a high similarity of about 60% to that of an insulin receptor, these receptors can form a heterodimer (Non-Patent Literature 1). Insulin can act on the insulin receptor to thereby express a strong effect of lowering the level of blood glucose, and is therefore used as a hypoglycemic drug.

2. IGF-I Receptor

An IGF-I receptor is a transmembrane protein consisting of an alpha chain and a beta chain, and has six extracellular domains (L1, CR, L2, Fn1, Fn2, and Fn3), a transmembrane domain, and an intracellular domain (Non-Patent Literature 2). The intracellular domain of the IGF-I receptor incorporates a tyrosine kinase. The extracellular domain is a CR (cysteine-rich) domain and participates in activation of the intracellular tyrosine kinase associated with conformational change of the IGF-I receptor, which occurs when IGF-I binds to the IGF-I receptor. The IGF-I receptor forms a homodimeric complex (homo form). IGF-I binding to the IGF-I receptor (homo form) triggers signaling via activation of the receptor kinase. The IGF-I receptor also forms a heterodimeric complex (hetero form) with the insulin receptor. Insulin or IGF-I binding to the IGF-I receptor (hetero form) triggers signaling via activation of the receptor kinase (Non-Patent Literatures 3 and 4).

3. Physiological Effects of IGF-I

IGF-I has been shown to exhibit growth promoting effects, such as increasing the body length and the body weight, and insulin-like metabolic effects, such as glucose metabolism acceleration and hypoglycemic effects. It has been revealed that mecasermin, a human recombinant IGF-I, improves symptoms related to insulin receptor abnormality, such as hyperglycemia, hyperinsulinemia, acanthosis *nigricans* and hirsutism. IGF-I has also been shown to improve growth disorder of dwarfism resistant to growth hormone (Non-Patent Literature 5).

As its growth promoting effects, IGF-I is known to promote the DNA synthetic capacity of human cartilage cells. It is also known that administration of IGF-I to a hypophysectomized rat increases its body weight and femur length (Non-Patent Literature 5).

4. Effect of IGF-I on Increasing Muscle Mass

Enhancement of cell proliferation activity with IGF-I requires continuous activation of the IGF-I receptor (Non-Patent Literature 6). An animal engineered to overexpress the IGF-I receptor exhibits increased muscle mass (Non-Patent Literature 7). Sustained administration of IGF-I/IGFBP3 to a patient with proximal femur fracture enhances her/his grip strength and improves her/his ability of standing from a seated position without assistance (Non-Patent Literature 8). The muscle IGF-I levels of the elderly humans and mice are known to be lower than those of the young (Non-Patent Literatures 9 and 10). Over expression of IGF-I specifically in muscle tissues of elderly mice improved their muscle masses compared to wild-type mice (Non-Patent Literature 11).

5. Precedent Products for Increasing Muscle Mass

Anamorelin, a ghrelin receptor agonist, increased lean body mass in a clinical trial for cachexia, which is a disuse muscle atrophy. However, it involves adverse effects such as inducing nausea and hyperglicemia (Non-Patent Literature 12).

Myostatin, a negative control factor of skeletal myogenesis, affects activin receptor II (ActRII) to thereby inhibit Akt/mTOR (Non-Patent Literatures 13 to 15).

LY2495655, an anti-myostatin antibody, increases the muscle masses of patients who received total hip replacement arthroplasty and those of elderly subjects (Non-Patent Literatures 16 and 17).

Bimagrumab, an anti-ActRII antibody, increases the muscle mass of neuromuscular disease patients (Non-Patent Literature 18).

However, there is no drug so far which promotes formation of skeletal muscles and can thereby be used for the treatment of a subject in need thereof.

6. Precedent Products for Promoting Growth

Human recombinant growth hormone (GH) formulation activates a GH receptor and induces IGF-I secretion, thereby exhibiting growth promoting effects. However, since the formulation requires once-daily administration via subcutaneous injection, it often causes poor drug compliance (e.g., unintentional omission of medication) and results in reduction in growth effects (Non-Patent Literature 19). There is an ongoing attempt to develop a long-acting GH formulation with improved kinetics which is to be administered once every one or two weeks.

However, there is no drug so far which exhibits growth promoting effects and can thereby be used for the treatment of a subject in need thereof with improved drug compliance. In addition, the GH formulation has been found to exhibit reduced growth effects on patients of GH receptor abnormality with reduced sensitivity to activation of the GH receptor, or patients resistant to GH treatment (Non-Patent Literature 20).

IGF-I is the only therapeutic agent which has growth promoting effect on a patient having reduced sensitivity to the GH receptor activation, since it acts on any point downstream of the GH receptor. However, the IGF-I formulation is a parenteral solution to be administered twice daily and therefore likely to cause poor drug compliance. In addition, it has been shown to cause hypoglycemia as an adverse effect (Non-Patent Literature 21). There is no drug so far which has improved drug compliance and reduced occurrence of hypoglycemia than IGF-I and can be used as an alternative therapeutic agent.

7. Hypoglycemic Effect of IGF-I

IGF-I is known to have hypoglycemic effect as an insulin-like effect. IGF-I enhances glucose uptake effect of rat muscle-derived cells (Non-Patent Literature 5). Administration of IGF-I also reduces the blood glucose level of rats (Non-Patent Literature 5).

It has been reported that the glucose lowering effect of IGF-I cause hypoglycemia as a clinical adverse effect (Non-Patent Literature 21). Likewise, administration of IGF-I to a human subject causes hypoglycemia. Therefore, at the onset of IGF-I treatment, it is necessary to keep controlling the dosage starting from a low dosage with observing various clinical findings including the blood glucose level after administration (Non-Patent Literature 5).

IGF-I expresses hypoglycemic effect via promotion of Akt phosphorylation, which is a downstream signal of the IGF-I receptor. An active variant of Akt enhances glucose uptake by 3T3-L1 cells (Non-Patent Literature 22). On the other hand, an Akt2-deficient mouse exhibited elevated blood glucose level (Non-Patent Literature 23). An Akt inhibitor inhibits insulin-induced glucose uptake by rat muscle-derived cells (Non-Patent Literature 24). IGF-I is also known to activate an insulin receptor which plays a role in hypoglycemic effect. These findings suggest that the hypoglycemic effect of IGF-I involves overactivation of Akt and activation of the insulin receptor.

8. Short Half-Life of IGF-I in Blood

IGF-I has a short half-life in blood, and therefore requires frequent administrations when used in treatment. In fact, mecasermin, a human recombinant IGF-I, has a blood half-life of about 11 hours to about 16 hours, and therefore needs to be administered once to twice daily in the treatment of dwarfism (Non-Patent Literature 5).

About 70 to 80% of IGF-I is bound to IGFBP3 in blood, while a free form of IGF-I exhibits physiological effect. Binding of IGF-I to IGFBP3 maintains its half-life in blood to a time period of from about 10 hours to about 16 hours (Non-Patent Literature 1).

IPLEX, a combination drug of IGF-I with IGFBP3, exhibited a blood half-life extended from that of IGF-I to a time period of about 21 hours to about 26 hours, and thereby allowed for reduction of administration frequency to once daily (Non-Patent Literature 23). However, IPLEX was already withdrawn from the market.

There has been also an attempt to develop a PEGylated IGF-I with improved IGF-I kinetics, but no drug has successfully been developed so far and is currently available (Patent Literature 1).

9. Therapeutic Effects Expected to be Achieved Via IGF-I's Effects

IGF-I is known to affect various organs and exerts a wide variety of physiological functions (Non-Patent Literature 21).

IGF-I has been reported to have neuroprotective effect on the central nervous system by protecting mitochondria and antioxidant effect via activation of the IGF-I receptor (Non-Patent Literatures 26 and 27). IGF-I promotes regeneration of injured neurites (Non-Patent Literature 28).

IGF-I is a main factor of growth promotion (Non-Patent Literatures 29 and 30). In fact, mecasermin, a human recombinant IGF-I, is clinically used as a drug for the treatment of dwarfism.

IGF-I is deemed to be effective in the treatment of hepatic cirrhosis, which evolves from liver damage or chronic liver disease and involves hepatic fibrosis. Administration of IGF-I improved hepatic fibrosis in a model animal of hepatic cirrhosis (Non-Patent Literature 31).

IGF-I is also known to play a role in the development and functions of kidney. IGF-I has protective effect against oxidative stress and apoptosis due to glucotoxicity in mesangial cells of kidney (Non-Patent Literature 32). IGF-I is expected as a drug for the treatment of nephropathy.

Examples of conditions expected to be improved via IGF-I administration include: dwarfism, Laron syndrome, hepatic cirrhosis, hepatic fibrosis, aging, intrauterine growth restriction (IUGR), neurological disease, cerebral stroke, spinal cord injury, cardiovascular protection, diabetes, insulin resistant, metabolic syndrome, nephropathy, osteoporosis, cystic fibrosis, wound healing, myotonic dystrophy, AIDS-associated sarcopenia, HIV-associated fat redistribution syndrome, burn, Crohn's disease, Werner's syndrome, X-linked combined immunodeficiency disease, hearing loss, anorexia nervosa, and retinopathy of prematurity (Non-Patent Literature 21).

Thus, IGF-I is expected as a drug for the treatment of a variety of diseases because of its wide spectrum of physiological effects. However, problems such as its adverse hypoglycemic effect and its short half-life requiring multiple administrations have prevented its clinical applications.

10. IGF-I Receptor Agonist Antibodies

In general, antibody formulations have long half-life, and prove effective if administered once to twice a month. Although some IGF-I receptor agonist antibodies have been reported to be effective in activating the receptor in vitro, no antibodies have been reported to exhibit agonistic activity against the IGF-I receptor in vivo (Non-Patent Literatures 33 to 37).

Specifically, antibodies 3B7 and 2D1 enhance cellular DNA synthesis in vitro (Non-Patent Literature 34).

Antibodies 11A1, 11A4, 11A11, and 24-57 enhance tyrosine phosphorylation of IGF-I receptor in vitro (Non-Patent Literature 35).

Antibodies 16-13, 17-69, 24-57, 24-60, 24-31, and 26-3 are shown to be effective in promoting cellular DNA synthesis and glucose uptake in vitro, and have the potential to exhibit hypoglycemic effect (Non-Patent Literatures 36 and 37).

However, no IGF-I receptor agonist antibody has been reported to exhibit cell proliferation effects in an in vitro experiment using primary cultured cells, inter alia, human myoblasts, let alone muscle-mass increasing effects in vivo.

11. IGF-I Receptor Antagonist Antibodies

There are attempts to use an antibody which binds to the IGF-I receptor for the treatment of malignancies, based on its antagonist effect of inhibiting binding of IGF-I to the IGF-I receptor. However, existing IGF-I receptor antagonist antibodies have various adverse effects such as hyperglycemia in monotherapy (Non-Patent Literature 38), and exhibit increased incidence of hyperglycemia when used in combination with other anticancer agents (Non-Patent Literature 39). Accordingly, their therapeutic applications are expected to be limited.

LIST OF CITATIONS

Patent Literature

[Patent Literature 1] Use of PEGylated Igf-I Variants for the Treatment of Neuromuscular Disorders, JP2011-518778A (WO2009/121759A) (2011)

Non-Patent Literature

[Non-Patent Literature 1] Ohlsson, C., et al., The role of liver-derived insulin-like growth factor-I. Endocr Rev, 2009. 30(5): p. 494-535.

[Non-Patent Literature 2] Kavran, J. M., et al., How IGF-I activates its receptor. Elife, 2014. 3.

[Non-Patent Literature 3] Bailyes, E. M., et al., Insulin receptor/IGF-I receptor hybrids are widely distributed in mammalian tissues: quantification of individual receptor species by selective immunoprecipitation and immunoblotting. Biochem J, 1997. 327 (Pt 1): p. 209-15.

[Non-Patent Literature 4] Pandini, G., et al., Insulin/insulin-like growth factor I hybrid receptors have different biological characteristics depending on the insulin receptor isoform involved. J Biol Chem, 2002. 277(42): p. 39684-95.

[Non-Patent Literature 5] OrphanPacific, IF. 2015.

[Non-Patent Literature 6] Fukushima, T., et al., Phosphatidylinositol 3-kinase (PI3K) activity bound to insulin-like growth factor-I (IGF-I) receptor, which is continuously sustained by IGF-I stimulation, is required for IGF-I-induced cell proliferation. J Biol Chem, 2012. 287(35): p. 29713-21.

[Non-Patent Literature 7] Schiaffino, S. and C. Mammucari, Regulation of skeletal muscle growth by the IGF-I-Akt/PKB pathway: insights from genetic models. Skelet Muscle, 2011. 1(1): p. 4.

[Non-Patent Literature 8] Boonen, S., et al., Musculoskeletal effects of the recombinant human IGF-I/IGF binding protein-3 complex in osteoporotic patients with proximal femoral fracture: a double-blind, placebo-controlled pilot study. J Clin Endocrinol Metab, 2002. 87(4): p. 1593-9.

[Non-Patent Literature 9] Barton-Davis, E. R., et al., Viral mediated expression of insulin-like growth factor I blocks the aging-related loss of skeletal muscle function. Proc Natl Acad Sci USA, 1998. 95(26): p. 15603-7.

[Non-Patent Literature 10] Lamberts, S. W., A. W. van den Beld, and A. J. van der Lely, The endocrinology of aging. Science, 1997. 278(5337): p. 419-24.

[Non-Patent Literature 11] Musaro, A., et al., Localized IGF-I transgene expression sustains hypertrophy and regeneration in senescent skeletal muscle. Nat Genet, 2001. 27(2): p. 195-200.

[Non-Patent Literature 12] Temel, J. S., et al., Anamorelin in patients with non-small-cell lung cancer and cachexia (ROMANA 1 and ROMANA 2): results from two randomized, double-blind, phase 3 trials. Lancet Oncol, 2016. 17(4): p. 519-31.

[Non-Patent Literature 13] Glass, D. J., Signaling pathways perturbing muscle mass. Curr Opin Clin Nutr Metab Care, 2010. 13(3): p. 225-9.

[Non-Patent Literature 14] Lee, S. J. and A. C. McPherron, Regulation of myostatin activity and muscle growth. Proc Natl Acad Sci USA, 2001. 98(16): p. 9306-11.

[Non-Patent Literature 15] Amirouche, A., et al., Down-regulation of Akt/mammalian target of rapamycin signaling pathway in response to myostatin overexpression in skeletal muscle. Endocrinology, 2009. 150(1): p. 286-94.

[Non-Patent Literature 16] Woodhouse, L., et al., A Phase 2 Randomized Study Investigating the Efficacy and Safety of Myostatin Antibody LY2495655 versus Placebo in Patients Undergoing Elective Total Hip Arthroplasty. J Frailty Aging, 2016. 5(1): p. 62-70.

[Non-Patent Literature 17] Becker, C., et al., Myostatin antibody (LY2495655) in older weak fallers: a proof-of-concept, randomized, phase 2 trial. Lancet Diabetes Endocrinol, 2015. 3(12): p. 948-57.

[Non-Patent Literature 18] Amato, A. A., et al., Treatment of sporadic inclusion body myositis with bimagrumab. Neurology, 2014. 83(24): p. 2239-46.

[Non-Patent Literature 19] Cutfield, W. S., et al., Non-compliance with growth hormone treatment in children is common and impairs linear growth. PLos One., 2011.6 (1):e16223

[Non-Patent Literature 20] Bang, P., et al., Identification and management of poor response to growth-promoting therapy in children with short stature. Clin Endocrinol (Oxf)., 2012.77(2):p. 169-181.

[Non-Patent Literature 21] Puche, J. E. and I. Castilla-Cortazar, Human conditions of insulin-like growth factor-I (IGF-I) deficiency. J Transl Med, 2012. 10: p. 224.

[Non-Patent Literature 22] Kohn, A. D., et al., Expression of a constitutively active Akt Ser/Thr kinase in 3T3-L1 adipocytes stimulates glucose uptake and glucose transporter 4 translocation. J Biol Chem, 1996. 271(49): p. 31372-8.

[Non-Patent Literature 23] Cho, H., et al., Insulin resistance and a diabetes mellitus-like syndrome in mice lacking the protein kinase Akt2 (PKB beta). Science, 2001. 292 (5522): p. 1728-31.

[Non-Patent Literature 24] Green, C. J., et al., Use of Akt inhibitor and a drug-resistant mutant validates a critical role for protein kinase B/Akt in the insulin-dependent regulation of glucose and system A amino acid uptake. J Biol Chem, 2008. 283(41): p. 27653-67.

[Non-Patent Literature 25] Submission for marketing application to FDA, APPLICATION NUMBER, 21-884

[Non-Patent Literature 26] Garcia-Fernandez, M., et al., Low doses of insulin-like growth factor I improve insulin resistance, lipid metabolism, and oxidative damage in aging rats. Endocrinology, 2008. 149(5): p. 2433-42.

[Non-Patent Literature 27] Puche, J. E., et al., Low doses of insulin-like growth factor-I induce mitochondrial protection in aging rats. Endocrinology, 2008. 149(5): p. 2620-7.

[Non-Patent Literature 28] Joseph D'Ercole, A. and P. Ye, Expanding the mind: insulin-like growth factor I and brain development. Endocrinology, 2008. 149(12): p. 5958-62.

[Non-Patent Literature 29] Abuzzahab, M. J., et al., IGF-I receptor mutations resulting in intrauterine and postnatal growth retardation. N Engl J Med, 2003. 349(23): p. 2211-22.

[Non-Patent Literature 30] Woods, K. A., et al., Intrauterine growth retardation and postnatal growth failure associated with deletion of the insulin-like growth factor I gene. N Engl J Med, 1996. 335(18): p. 1363-7.

[Non-Patent Literature 31] Perez, R., et al., Mitochondrial protection by low doses of insulin-like growth factor-I in experimental cirrhosis. World J Gastroenterol, 2008. 14(17): p. 2731-9.

[Non-Patent Literature 32] Kang, B. P., et al., IGF-I inhibits the mitochondrial apoptosis program in mesangial cells exposed to high glucose. Am J Physiol Renal Physiol, 2003. 285(5): p. F1013-24.

[Non-Patent Literature 33] Bhaskar, V., et al., A fully human, allosteric monoclonal antibody that activates the insulin receptor and improves glycemic control. Diabetes, 2012. 61(5): p. 1263-71.

[Non-Patent Literature 34] Xiong, L., et al., Growth-stimulatory monoclonal antibodies against human insulin-like growth factor I receptor. Proc Natl Acad Sci USA, 1992. 89(12): p. 5356-60.

[Non-Patent Literature 35] Runnels, H. A., et al., Human monoclonal antibodies to the insulin-like growth factor 1 receptor inhibit receptor activation and tumor growth in preclinical studies. Adv Ther, 2010. 27(7): p. 458-75.

[Non-Patent Literature 36] Soos, M. A., et al., A panel of monoclonal antibodies for the type I insulin-like growth factor receptor. Epitope mapping, effects on ligand binding, and biological activity. J Biol Chem, 1992. 267(18): p. 12955-63.

[Non-Patent Literature 37] Kato, H., et al., Role of tyrosine kinase activity in signal transduction by the insulin-like growth factor-I (IGF-I) receptor. Characterization of kinase-deficient IGF-I receptors and the action of an IGF-I-mimetic antibody (alpha IR-3). J Biol Chem, 1993. 268(4): p. 2655-61.

[Non-Patent Literature 38] Atzori, F., et al., A Phase I Pharmacokinetic and Pharmacodynamic Study of Dalotuzumab (MK-0646), an Anti-Insulin-like Growth Factor-1 Receptor Monoclonal Antibody, in Patients with Advanced Solid Tumors. Clin Cancer Res., 2011.17(19): p. 6304-12.

[Non-Patent Literature 39] de Bono J. S., et al., Phase II randomized study of figitumumab plus docetaxel and docetaxel alone with crossover for metastatic castration-resistant prostate cancer. Clin Cancer Res., 2014.20(7):p. 1925-34.

SUMMARY

Problem to be Solved by the Invention

An objective of the present invention is to provide an anti-IGF-I receptor antibody or its fragment or a derivative thereof which specifically binds to an IGF-I receptor of a vertebrate. Another objective of the present invention is to provide an antibody which increases the muscle mass or the thickness of growth plate cartilage via the IGF-I receptor while not reducing the blood glucose level.

Means to Solve the Problem

The present invention relates to the following:

Aspect [1] An anti-IGF-I receptor antibody or its fragment or a derivative thereof which specifically binds to an IGF-I receptor of a vertebrate, and exhibits an activity to induce growth of vertebrate-derived cells.

Aspect [2] The anti-IGF-I receptor antibody or its fragment or a derivative thereof according to Aspect [1], wherein the activity of the antibody, fragment, or derivative to induce growth of vertebrate-derived cells is equal to or higher than the corresponding activity of a wild-type IGF-I.

Aspect [3] The anti-IGF-I receptor antibody or its fragment or a derivative thereof according to Aspect [1] or Aspect [2], wherein the $EC_{50}$ value of the antibody, fragment, or derivative for inducing growth of vertebrate-derived cells in vitro is 1/20 or less of the corresponding value of a wild-type IGF-I.

Aspect [4] The anti-IGF-I receptor antibody or its fragment or a derivative thereof according to any one of Aspect [1] to Aspect [3], wherein when the antibody, fragment, or derivative is contacted with cultured vertebrate-derived cells, the duration of activity of the antibody, fragment, or derivative to induce growth of the cultured cells relative to the duration of contact is improved than a wild-type IGF-I.

Aspect [5] The anti-IGF-I receptor antibody or its fragment or a derivative thereof according to any one of Aspect [2] to Aspect [4], wherein the wild-type IGF-I is a human IGF-I having an amino acid sequence defined in SEQ ID NO:1.

Aspect [6] The anti-IGF-I receptor antibody or its fragment or a derivative thereof according to any one of Aspect [1] to Aspect [5], wherein the $EC_{50}$ value of the antibody, fragment, or derivative for inducing growth of vertebrate-derived cells in vitro is 0.1 nmol/L or lower.

Aspect [7] The anti-IGF-I receptor antibody or its fragment or a derivative thereof according to any one of Aspect [1] to Aspect [6], which exhibits an activity to induce an increase in the muscle mass and/or the body length of a vertebrate when parenterally administered to the vertebrate.

Aspect [8] The anti-IGF-I receptor antibody or its fragment or a derivative thereof according to any one of Aspect [1] to Aspect [7], which is administered to a vertebrate at a frequency of once a week or less.

Aspect [9] The anti-IGF-I receptor antibody or its fragment or a derivative thereof according to any one of Aspect [1] to Aspect [8], wherein the vertebrate is a human; a non-human animal including a guinea pig, a monkey, a rabbit, a cow, a pig, a horse, a sheep, a dog, or a fowl; or a non-human animal engineered to express a human IGF-I receptor.

Aspect [10] The anti-IGF-I receptor antibody or its fragment or a derivative thereof according to any one of Aspect [1] to Aspect [9], which does not induce glucose uptake by differentiated muscle cells when administered at a dosage sufficient to induce growth of vertebrate-derived cells.

Aspect [11] The anti-IGF-I receptor antibody or its fragment or a derivative thereof according to Aspect [10], which does not induce glucose uptake by differentiated muscle cells when administered at a dosage of 100 times or more of the $EC_{50}$ value for inducing growth of vertebrate-derived cells in vitro.

Aspect [12] The anti-IGF-I receptor antibody or its fragment or a derivative thereof according to Aspect [10] or Aspect [11], wherein the vertebrate-derived cells are myoblasts derived from a human or a non-human mammal.

Aspect [13] The anti-IGF-I receptor antibody or its fragment or a derivative thereof according to any one of Aspect [7] to Aspect [12], which does not lower the blood glucose level of a vertebrate when parenterally administered to the vertebrate at a dosage sufficient to induce an increase in the muscle mass and/or the body length of the vertebrate.

Aspect [14] The anti-IGF-I receptor antibody or its fragment or a derivative thereof according to Aspect [13], which does not change the blood glucose level of a vertebrate when parenterally administered to the vertebrate at a dosage of 10 times or more of an effective dosage sufficient to induce an increase in the muscle mass and/or the body length of the vertebrate.

Aspect [15] An anti-IGF-I receptor antibody or its fragment or a derivative thereof, according to any one of Aspect [1] to Aspect [14], which binds to a CR domain of an IGF-I receptor.

Aspect [16] An anti-IGF-I receptor antibody or its fragment or a derivative thereof, which binds to a CR domain of an IGF-I receptor, and inhibits binding of IGF-I or IGF-II to an IGF-I receptor.

Aspect [17] The anti-IGF-I receptor antibody or its fragment or a derivative thereof according to Aspect [16], which binds to an epitope containing ProSerGlyPheIleArgAsnX$_1$X$_2$GlnSerMet (where X$_1$ represents Gly or Ser and X$_2$ represents Ser or Thr) (SEQ ID NO: 31), or a part in the vicinity thereof, in the sequence of the CR domain of the IGF-I receptor.

Aspect [18] The anti-IGF-I receptor antibody or its fragment or a derivative thereof according to Aspect [17], which binds to an epitope containing ProSerGlyPheIleArgAsnGlySerGlnSerMet (SEQ ID NO: 32), or a part in the vicinity thereof, in the sequence of the CR domain of the IGF-I receptor.

Aspect [19] The anti-IGF-I receptor antibody or its fragment or a derivative thereof according to any one of Aspect [1] to Aspect [18], which has a cross-reactivity with an IGF-I receptor of a human or a non-human animal including a guinea pig, a monkey, a rabbit, a cow, a pig, a horse, a sheep, a dog, or a fowl.

Aspect [20] The anti-IGF-I receptor antibody or its fragment or a derivative thereof according to any one of Aspect [1] to Aspect [19], which causes an antigen-antibody reaction with an affinity intensity at a equilibrium dissociation constant (KD) of $1 \times 10^{-8}$M or less.

Aspect [21] The anti-IGF-I receptor antibody or its fragment or a derivative thereof according to any one of Aspect [16] to Aspect [20], which has at least one of the features of:
1) exhibiting an activity to induce growth of vertebrate-derived cells;
2) exhibiting an activity to induce an increase in the muscle mass and/or the body length of a vertebrate when parenterally administered to the vertebrate;
3) not inducing glucose uptake by differentiated muscle cells when administered at a dosage sufficient to induce growth of vertebrate-derived cells; and
4) not changing the blood glucose level of a vertebrate when parenterally administered to the vertebrate at a dosage sufficient to induce an increase in the muscle mass and/or the body length of the vertebrate.

Aspect [22] The anti-IGF-I receptor antibody or its fragment or a derivative thereof according to any one of Aspect [16] to Aspect [21], which has at least one of the features of:
1) inhibiting growth of vertebrate-derived cells induced by IGF-I;
2) inhibiting IGF-I-induced cell proliferation in a vertebrate suffering a cell proliferative disease when parenterally administered to the vertebrate;
3) not affecting glucose uptake by differentiated muscle cells at a dosage sufficient to inhibit growth of vertebrate-derived cells induced by IGF-I; and
4) not changing the blood glucose level of a vertebrate suffering a cell proliferative disease when parenterally administered to the vertebrate at a dosage sufficient to inhibit IGF-I-induced cell proliferation in the vertebrate.

Aspect [23] The anti-IGF-I receptor antibody or its fragment or a derivative thereof according to any one of Aspect [1] to Aspect [22], which is a Fab, scFv, diabody or bispecific antibody, or a derivative thereof.

Aspect [24] The anti-IGF-I receptor antibody or its fragment or a derivative thereof according to any one of Aspect [1] to Aspect [23], consisting of an amino acid sequence comprising:

as a heavy chain variable region CDR-1 (CDR-H1) sequence, an amino acid sequence defined in SEQ ID NO:3 or an amino acid sequence derived from SEQ ID NO:3 via substitution, deletion or insertion of any one amino acid residue;

as a heavy chain variable region CDR-2 (CDR-H2) sequence, an amino acid sequence defined in SEQ ID NO:4 or an amino acid sequence derived from SEQ ID NO:4 via substitution, deletion or insertion of any one or two amino acid residues;

as a heavy chain variable region CDR-3 (CDR-H3) sequence, an amino acid sequence defined in SEQ ID NO:5 or an amino acid sequence derived from SEQ ID NO:5 via substitution, deletion or insertion of any one or two amino acid residues;

as a light chain variable region CDR-1 (CDR-L1) sequence, an amino acid sequence defined in SEQ ID NO:6 or an amino acid sequence derived from SEQ ID NO:6 via substitution, deletion or insertion of any one or two amino acid residues;

as a light chain variable region CDR-2 (CDR-L2) sequence, an amino acid sequence defined in SEQ ID NO:7 or an amino acid sequence derived from SEQ ID NO:7 via substitution, deletion or insertion of any one amino acid residue; and as a light chain variable region CDR-3 (CDR-L3) sequence, an amino acid sequence defined in SEQ ID NO:8 or an amino acid sequence derived from SEQ ID NO:8 via substitution, deletion or insertion of any one or two amino acid residues.

Aspect [25] The anti-IGF-I receptor antibody or its fragment or a derivative thereof according to Aspect [24 further comprises a framework sequence of immunoglobulin.

Aspect [26] The anti-IGF-I receptor antibody or its fragment or a derivative thereof according to Aspect [25], wherein the framework sequence of immunoglobulin is a framework sequence of each class of immunoglobulin from a human or a non-human animal including a guinea pig, a monkey, a rabbit, a cow, a pig, a horse, a sheep, a dog, a fowl, a mouse, or a rat.

Aspect [27] The anti-IGF-I receptor antibody or its fragment or a derivative thereof according to any one of Aspect [1] to Aspect [26], which consists of an amino acid sequence comprising:

as a heavy chain variable region, an amino acid sequence defined in SEQ ID NO:9 or an amino acid sequence having a similarity of 90% or more to SEQ ID NO:9; and as a light chain variable region, an amino acid sequence defined in SEQ ID NO:10 or an amino acid sequence having a similarity of 90% or more to SEQ ID NO:10.

Aspect [28] The anti-IGF-I receptor antibody or its fragment or a derivative thereof according to any one of Aspect [1] to Aspect [27] further comprising a constant region of each class of immunoglobulin a human or a non-human animal including a guinea pig, a monkey, a rabbit, a cow, a pig, a horse, a sheep, a dog, a fowl, a mouse, or a rat.

Aspect [29] A nucleic acid molecule consisting of a polynucleotide sequence encoding an anti-IGF-I receptor antibody or its fragment or a derivative thereof according to any one of Aspect [1] to Aspect [28].

Aspect [30] A cloning vector or expression vector comprising at least one nucleic acid molecule according to Aspect [29].

Aspect [31] A recombinant cell derived from a host cell via transfection of a vector according to Aspect [30].

Aspect [32] A process of producing an anti-IGF-I receptor antibody or its fragment or a derivative thereof according to any one of Aspect [1] to Aspect [28], comprising:
culturing a recombinant cell according to Aspect [31]; and
purifying the anti-IGF-I receptor antibody, fragment, or derivative produced from the recombinant cell.

Aspect [33] A pharmaceutical composition comprising an anti-IGF-I receptor antibody or its fragment or a derivative thereof according to any one of Aspect [1] to Aspect [28], a nucleic acid molecule according to Aspect [29], a vector according to Aspect [30], or a recombinant cell according to Aspect [31].

Aspect [34] The pharmaceutical composition according to Aspect [33], further comprising an additional active ingredient other than the anti-IGF-I receptor antibody, fragment, or derivative according to any one of Aspect [1] to Aspect [28], the nucleic acid molecule according to Aspect [29], the vector according to Aspect [30], or the recombinant cell according to Aspect [31].

Aspect [35] The pharmaceutical composition according to Aspect [34], wherein the active ingredient is one or more selected from a growth hormone or an analog thereof, insulin or an analog thereof, IGF-II or an analog thereof, an anti-myostatin antibody, a myostatin antagonist, an anti-activin type IIB receptor antibody, an activin type IIB receptor antagonist, a soluble activin type IIB receptor or an analog thereof, ghrelin or an analog thereof, follistatin or an analog thereof, a beta-2 agonist, and a selective androgen receptor modulator.

Aspect [36] The pharmaceutical composition according to Aspect [34] or Aspect [35], wherein the active ingredient comprises an ingredient selected from the group consisting of: corticosteroid, antiemetic, ondansetron hydrochloride, granisetron hydrochloride, metoclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesic, ibuprofen, naproxen, choline magnesium trisalicylate, oxycodone hydrochloride, anti-angiogenic, antithrombotic, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGFantibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative, farnesyl protein transferase inhibitor, alpha v beta 3 inhibitor, alpha v beta 5 inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

Aspect [37] A medical drug for use in the treatment or prevention of a condition associated with IGF-I or IGF-II, comprising comprising an anti-IGF-I receptor antibody or its fragment or a derivative thereof according to any one of Aspect [1] to Aspect [28], a nucleic acid molecule according to Aspect [29], a vector according to Aspect [30], or a recombinant cell according to Aspect [31].

Aspect [38] The medical drug according to Aspect [37], wherein the condition associated with IGF-I is selected from: disuse muscle atrophy, dwarfism, diabetic nephropathy, chronic renal failure, Laron syndrome, hepatic cirrhosis, hepatic fibrosis, aging, intrauterine growth restriction (IUGR), neurological disease, cerebral stroke, spinal cord injury, cardiovascular protection, diabetes, insulin resistant, metabolic syndrome, osteoporosis, cystic fibrosis, wound healing, myotonic dystrophy, AIDS-associated sarcopenia, HIV-associated fat redistribution syndrome, burn, Crohn's disease, Werner's syndrome, X-linked combined immunodeficiency disease, hearing loss, anorexia nervosa and retinopathy of prematurity, Turner's syndrome, Prader-Willi syndrome, Silver-Russell syndrome, idiopathic short stature, obesity, multiple sclerosis, fibromyalgia, ulcerous colitis, low muscle mass, myocardial ischemia and decreased bone density.

Aspect [39] The medical drug according to Aspect [37] or Aspect [38], which is parenterally administered.

Aspect [40] The medical drug according to any one of Aspect [37] to Aspect [39], which is a veterinary drug to be administered to a non-human animal.

Aspect [41] The medical drug according to Aspect [40], wherein the veterinary drug is administered for the purpose of, increasing muscle mass and/or body length, promoting growth, increasing milk production, promoting reproduction, or preventing aging.

Aspect [42] The medical drug according to Aspect [40] or Aspect [41], wherein the non-human animal is a guinea pig, a monkey, a rabbit, a cow, a pig, a horse, a sheep, a dog, or a fowl.

Aspect [43] The medical drug according to any one of Aspect [37] to Aspect [42], for the treatment or prevention of a disease caused by an effect of IGF-I or IGF-II on an IGF-I receptor.

Aspect [44] The medical drug according to Aspect [43], wherein the disease caused by an effect of IGF-I or IGF-II on an IGF-I receptor is selected from the group consisting of: liver cancer, neuroblastoma, striated muscle sarcoma, bone cancer, childhood cancer, acromegalia, ovary cancer, pancreas cancer, benignant prostatic hypertrophy, breast cancer, prostate cancer, bone cancer, lung cancer, colorectal cancer, cervix cancer, synovial sarcoma, urinary bladder cancer, stomach cancer, Wilms' tumor, diarrhea associated with metastatic carcinoid and vasoactive intestinal peptide secreting tumor, vipoma, Verner-Morrison syndrome, Beckwith-Wiedemann syndrome, kidney cancer, renal cell cancer, transitional cell cancer, Ewing's sarcoma, leukemia, acute ymphoblastic leukemia, brain tumor, glioblastoma, non-glioblastomatic brain tumor, meningioma, pituitary adenoma, vestibular schwannoma, primitive neuroectodermal tumor, medulloblastoma, astrocytoma, oligodendroglioma, ependymoma, choroid plexus papilloma, gigantism, psoriasis, atherosclerosis, vascular smooth muscle restenosis, inappropriate microvascular growth, diabetic retinopathy, Graves' disease, multiple sclerosis, systemic lupus erythematosus, chronic thyroiditis, myasthenia gravis, autoimmune thyroiditis and Behcet's disease.

Aspect [45] A method of culturing vertebrate-derived cells in vitro, comprising contacting the vertebrate-derived cells with an anti-IGF-I receptor antibody or its fragment or a derivative thereof according to any one of Aspect [1] to Aspect [28], a nucleic acid molecule according to Aspect [29], a vector according to Aspect [30], and a recombinant cell according to Aspect [31] when culturing the cells.

Aspect [46] The method according to Aspect [45], wherein said contacting is carried out for the purpose of promoting growth or inducing differentiation of the vertebrate-derived cells.

Aspect [47] The method according to Aspect [45] or Aspect [46], wherein the anti-IGF-I receptor antibody, fragment, or derivative is adsorbed by, or immobilized to, a solid phase.

Aspect [48] A transgenic animal comprising an IGF-I receptor gene which has been mutated in a CR domain thereof via gene engineering such that the CR domain includes an amino acid sequence represented by ProSerGlyPheIleArgAsnGlySerGlnSerMet (SEQ ID NO: 32).

Aspect [49] A transgenic animal into which a heterologous IGF-I receptor gene has been transfected, wherein the amino acid sequence encoded by the heterologous IGF-I receptor gene differs from the amino acid sequence encoded by the animal's inherent IGF-I receptor gene in amino acid residue(s) $X_1$ and/or $X_2$ of a sequence represented by ProSerGlyPheIleArgAsn$X_1X_2$GlnSerMet (SEQ ID NO: 31) in a CR domain.

Effect of the Invention

The anti-IGF-I receptor antibody or its fragment or a derivative thereof according to the present invention has an effect of specifically binding to an IGF-I receptor of a vertebrate.

BRIEF EXPLANATION OF THE DRAWINGS

FIG. 1 illustrates aligned amino acid sequences of CR domains of the mouse (residues 121-360 of SEQ ID NO: 15), rat (residues 121-360 of SEQ ID NO: 14), human (residues 121-359 of SEQ ID NO: 2), guinea pig (residues 121-359 of SEQ ID NO: 11) and rabbit (residues 121-359 of SEQ ID NO: 13) IGF-I receptors, in which the amino acid sequences are indicated using the one letter code;

FIG. 2 is a graph indicating the results of ELISA using variants of a presumptive epitope of IGF11-16;

MODES FOR CARRYING OUT THE INVENTION

Figure 3:
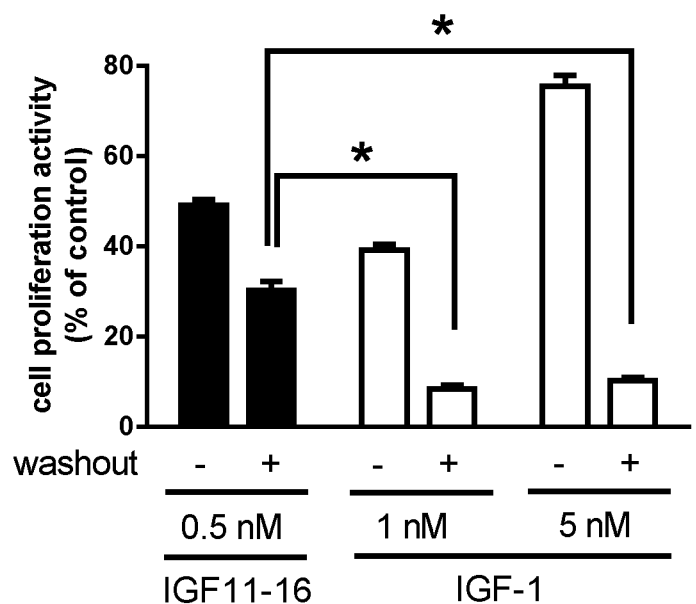
FIG. 3 is a graph indicating the growth activity of human myoblasts after removal of IGF11-16 and IGF-I.

In the following description, the present invention will be explained with reference to specific embodiments, although the present invention should not be limited to these embodiments in any way. All the documents cited in the present specification, including patent publications, unexamined application publications, and non-patent literatures, are hereby incorporated by reference in their entirety for all purposes.

[IGF]

IGF refers to an insulin-like growth factor, which may be either IGF-I or IGF-II. Both IGF-I and IGF-II are biological ligands having agonist activities which bind to an IGF-I receptor (insulin-like growth factor-I receptor) and transduce signals such as cell division and metabolism into the cell. IGF-I and IGF-II are also known to have cross-binding activity to an insulin receptor (INSR), which is structurally similar to the IGF-I receptor. The present specification will mainly discuss IGF-I, since its properties such as physiological functions are known more than those of IGF-II. However, in the context of discussion about various effects and diseases mediated via binding of a ligand to the IGF-I receptor, both IGF-I and IGF-II may collectively be mentioned.

IGF-I, also referred to as somatomedin C, is a single polypeptide hormone consisting of 70 amino acids. The sequence of human IGF-I is available, e.g., on the EMBL-EBI with UniProtKB accession number P50919. The amino acid sequence of mature IGF-I is shown in SEQ ID NO:1 of the sequence listing attached hereto. This 70 amino acid sequence is conserved in many species. In the present invention, the term "IGF-I" without any limitation means an IGF-I protein having such hormone activity, unless specified otherwise.

IGF-I is produced by a variety of cells in the living body, including liver cells, and exists in blood and other body fluids. Therefore, wild-type IGF-I can be obtained via purification from body fluid of an animal or from a primary cultured cell or a cultured cell line derived from an animal. Since a growth hormone induces IGF-I production by cells, IGF-I can also be purified from body fluid of an animal to which a growth hormone has been administered, or from a primary cultured animal cell or an animal cell line incubated in the presence of a growth hormone. As a different method, IGF-I can also be obtained from a recombinant cell prepared by transfection of an expression vector carrying a nucleic acid molecule encoding an amino acid sequence of IGF-I into a host such as a prokaryotic organism (e.g., E. coli) or a eukaryotic cell including a yeast, an insect cell, or a cultured mammal-derived cell, or from a transgenic animal or a transgenic plant into which an IGF-I gene has been transfected. Human IGF-I is also available as a research reagent (Enzo Life Sciences, catalog: ADI-908-059-0100, Abnova, catalog:P3452, etc.) or as a pharmaceutical product (SOMAZON mecasermin, INCRELEX, etc.). The in vivo and in vitro activities of IGF-I for use can be evaluated as specific activities relative to an IGF-I standard substance under NIBSC code: 91/554, whose activity corresponds to one international unit/microgram. The standard substance is available from World Health Organization's National Institute for Biological Standards and Control (NIBSC). In the context of the present invention, IGF-I is considered as having a specific activity equivalent to the IGF-I of NIBSC code: 91/554.

[IGF-I Receptor]

The term "IGF-I receptor" refers to an insulin-like growth factor-I receptor. The term "IGF-I receptor" used herein means an IGF-I receptor protein, unless specified otherwise. The IGF-I receptor is a protein formed with two subunits, each consisting of an alpha chain and a beta chain. The amino acid sequence of a human IGF-I receptor is indicated in SEQ ID NO:2, of which a subsequence consisting of the $31^{st}$ to $735^{th}$ amino acid residues represents the alpha chain, while a subsequence starting from the 740$^{th}$ amino acid residue represents the beta chain. The alpha chain of the IGF-I receptor has a portion to which IGF-I binds, while the beta chain has a transmembrane structure and exhibits a function to transmit signals into the cell. The alpha chain of the IGF-I receptor can be divided into L1, CR, L2, FnIII-1, and FnIII-2a/ID/FnIII-2b domains. According to the amino acid sequence of the human IGF-I receptor defined in SEQ ID NO:2, the 31$^{st}$ to 179$^{th}$ residues correspond to the L1 domain, the 180$^{th}$ to 328$^{th}$ residues correspond to the CR domain, the 329$^{th}$ to 491$^{st}$ residues correspond to the L2 domain, the 492$^{nd}$ to 607$^{th}$ residues correspond to the FnIII-1 domain, and the 608$^{th}$ to 735$^{th}$ residues correspond to the FnIII-2a/ID/FnIII-2b domain. Among them, the CR (cysteine-rich) domain is involved in the activation of an intracellular tyrosine kinase in the beta chain, which is associated with a conformational change of the IGF-I receptor occurring when IGF-I binds to the receptor. The amino acid sequence of human IGF-I receptor is available, e.g., on EMBL-EBI with UniProtKB-accession number P08069, and is also indicated in the sequence listing as SEQ ID NO:2.

The IGF-I receptor is known to be expressed in a wide range of tissues and cells in the living body, and receives various stimuli via IGF-I, such as induction of cell proliferation and activation of intracellular signals. In particular, effects of IGF-I on myoblasts via the IGF-I receptor can be evaluated using cell proliferation activities as indicators. For this reason, myoblasts are useful in analyzing the effects of antibodies binding to the IGF-I receptor. Cells expressing an IGF-I receptor derived from human or any other vertebrate can be prepared artificially, by transfection of an expression vector carrying a nucleic acid molecule encoding the amino acid sequence of an IGF-I receptor derived from human or any other vertebrate into a eukaryotic host cell, such as a cultured insect cell or a mammal-derived cell, to prepare a recombinant cell expressing the IGF-I receptor encoded by the transfected nucleic acid on its cell membrane. The resultant cell expressing the IGF-I receptor can be used for analysis of the binding ability and intracellular signal transmissibility of antibodies.

[Anti-IGF-I Receptor Antibody]

An antibody is a glycoprotein containing at least two heavy (H) chains and two light (L) chains coupled together via disulfide bindings. Each heavy chain has a heavy chain variable region (abbreviated as VH) and a heavy chain constant region. The heavy chain constant region contains three domains, i.e., CH1, CH2, and CH3. Each light chain contains a light chain variable region (abbreviated as VL) and a light chain constant region. A light chain constant region has one domain, i.e., CL. There are two types of light chain constant regions, i.e., λ (lambda) chain and κ (kappa) chain. Heavy chain constant regions are classified into γ (gamma) chain, μ (mu) chain, α (alpha) chain, δ (delta) chain and ε (epsilon) chain, and different types of heavy chain constant regions result in different isotypes of antibodies, i.e., IgG, IgM, IgA, IgD, and IgE, respectively. Each of the VH and VL regions is also divided into four relatively conserved regions (FR-1, FR-2, FR-3, and FR-4), collectively referred to as framework regions (FR), and three highly variable regions (CDR-1, CDR-2, and CDR-3), collectively referred to as complementarity determining regions (CDR). The VH region includes the three CDRs and the four FRs arranged in the order of FR-1, CDR-1 (CDR-H1), FR-2, CDR-2 (CDR-H2), FR-3, CDR-3 (CDR-H3), and FR-4 from the amino terminal to the carboxyl terminal. The VL includes the three CDRs and the four FRs arranged in the order of FR-1, CDR-1 (CDR-L1), FR-2, CDR-2 (CDR-L2), FR-3, CDR-3 (CDR-L3), and FR-4 from the amino terminal to the carboxyl terminal. The variable region of each of the heavy chain and the light chain includes a binding domain, which interacts with an antigen.

The antibody according to the present invention may be a fragment and/or derivative of an antibody. Examples of antibody fragments include F(ab')2, Fab, and Fv. Examples of antibody derivatives include: antibodies to which an amino acid mutation has been introduced in its constant region; antibodies in which the domain arrangement of the constant regions has been modified; antibodies having two or more Fc's per molecule; antibodies consisting only of a heavy chain or only of a light chain; antibodies with modified glycosylation; bispecific antibodies; conjugates of antibodies or antibody fragments with compounds or proteins other than antibodies; antibody enzymes; nanobodies; tandem scFv's; bispecific tandem scFv's; diabodies; and VHHs. The term "antibody" used herein encompasses such fragments and/or derivatives of antibodies, unless otherwise specified.

The term "monoclonal antibody" conventionally means antibody molecules obtained from a clone derived from a single antibody-producing cell, i.e., a single variety of antibody molecules having a combination of VH and VL with specific amino acid sequences. A monoclonal antibody can also be produced via genetic engineering procedure, by preparing a nucleic acid molecule having a gene sequence encoding the amino acid sequence of the monoclonal antibody protein. A person skilled in the art would also be familiar with techniques for modifying a monoclonal antibody using genetic information about, e.g., H chains, L chains, variable regions thereof, and CDR sequences thereof to thereby improve the binding ability and specificity of the antibody, and techniques for preparing an antibody suitable for a therapeutic agent by altering an animal antibody such as a mouse antibody into a human-type antibody. A human-type monoclonal antibody can also be prepared by sensitizing a non-human transgenic animal carrying a human antibody gene to an antigen. Another method which does not require sensitization of an animal is a technique involving: preparing a phage library expressing an antigen binding region of a human antibody or a part thereof (human antibody phage display); obtaining a phage clone expressing a peptide which specifically binds to a corresponding antigen or an antibody having a desired amino acid sequence; and producing a desired human antibody based on the information of the selected phage clone. A person skilled in the art can employ such a technique as appropriate (see, e.g., a review by Taketo Tanaka et al., Keio J. Med., Vol. 60, pp. 37-46). A person skilled in the art can also design an antibody to be administered to a non-human animal in a similar manner to a humanized antibody, by using information about amino acid sequences of CDRs and variable regions as appropriate.

The term "antigen-antibody reaction" used herein means that an antibody binds to an IGF-I receptor with an affinity represented by an equilibrium dissociation constant (KD) of $1\times10^{-8}$M or less. The antibody of the present invention should preferably bind to an IGF-I receptor with a KD of usually $1\times10^{-8}$M or less, particularly $1\times10^{-9}$M or less, more particularly $1\times10^{-10}$M or less.

The term "specificity" of an antibody used herein means that an antibody causes a strong binding based on antigen-antibody reaction to a specific antigen. In the context of the present invention, the IGF-I receptor-specific antibody means an antibody which, when used at a concentration sufficient to significantly cause antigen-antibody reaction with cells expressing an IGF-I receptor, causes antigen-antibody reaction with an INSR at a reactivity of 1.5 times or less the reactivity with a Mock cell. An INSR has a high similarity to an IGF-I receptor in primary structure (amino acid sequence) and higher-order structure.

A person skilled in the art would be able to carry out measurement of antigen-antibody reaction by selecting an appropriate binding assay in a system of a solid phase or liquid phase. Examples of such assays include, although not limited to: enzyme-linked immunosorbent assay (ELISA), enzyme immunoassay (EIA), surface plasmon resonance (SPR), fluorescence resonance energy transfer (FRET), and luminescence resonance energy transfer (LRET). Measurement of antigen-antibody binding affinity can be carried out by, e.g., labelling an antibody and/or an antigen with, e.g., an enzyme, a fluorescent material, a luminescent material, or a radioisotope, and detecting the antigen-antibody reaction using a method suitable for measuring the physical and/or chemical properties characteristic to the label used.

The anti-IGF-I receptor antibodies according to the present invention encompass both an agonist antibody and an antagonist antibody. When used singly, the IGF-I receptor agonist antibody of the present invention has an effect of enhancing the growth activity of myoblasts. When used in combination with IGF-I, the IGF-I receptor antagonist antibody of the present invention has an effect of inhibiting the IGF-I-induced growth activity of myoblasts.

The IGF-I receptor agonist antibody according to the present invention which binds strongly to a specific domain of the IGF-I receptor has an effect of enhancing the growth activity of myoblasts in vitro.

The IGF-I receptor agonist antibody of the present invention does not have an effect of enhancing glucose uptake by differentiated muscle cells in vitro at an effective concentration sufficient to enhance the growth activity of myoblasts, preferably at a concentration 10 times as high as the effective concentration, more preferably at a concentration 100 times as high as the effective concentration.

While IGF-I has remarkable hypoglycemic effect at a dosage sufficient to exhibit muscle-mass increasing effect, the IGF-I receptor agonist antibody of the present invention does not have hypoglycemic effect at an effective dosage sufficient to exhibit an effect of increasing muscle mass, preferably at a dosage 10 times as high as the effective dosage.

In addition, the IGF-I receptor agonist antibody, when administered to a guinea pig at a single dose, exhibit an in vivo activity to increase the muscle mass effect which corresponds to the activity achieved by sustained administration of IGF-I. The IGF-I receptor agonist antibody of the present invention also has a long half-life in blood, and exhibits muscle-mass increasing effect via single-dose administration to an animal.

Thus, the IGF-I receptor agonist antibody of the present invention has a potential as a therapeutic or prophylactic agent for a variety of diseases associated with the IGF-I receptor such as disuse muscle atrophy and dwarfism, for which IGF-I has also been expected to be effective. In addition, the IGF-I receptor agonist antibody of the present invention can solve the problems involved in IGF-I by, e.g., overcoming the hypoglycemic effect and extending the blood half-life.

The IGF-I receptor antagonist antibody of the present invention inhibits the binding of IGF-I to the IGF-I receptor. According to one embodiment of the IGF-I receptor antagonist antibody of the present invention, the antibody activates the IGF-I receptor while inhibiting the effects of IGF-I on the IGF-I receptor. In this embodiment, the antibody has an effect of negating an additive agonistic activity with IGF-I, e.g., an effect of negating the activity of IGF-I to induce growth of myoblasts. Another embodiment of the IGF-I receptor antagonist antibody of the present invention binds to, but does not activate, the IGF-I receptor. Examples of such antagonist antibodies which does not cause activation of the IGF-I receptor via cross-linking include, although not limited to: antibodies having monovalent antigen-binding ability, such as Fab and scFv; and antibodies having divalent binding sites, such as bispecific antibodies, in which only one of the binding sites binds to a specific domain of the IGF-I receptor, or in which the binding sites are spaced with a controlled interval using a linker. When preparing the IGF-I receptor antagonist antibody according to the present invention, it is possible to confirm whether the antibody binds to the IGF-I receptor but lacks agonistic activity by: determining whether the antibody has binding ability to the IGF-I receptor using a method of measuring antigen-antibody reactivity between the antibody and the IGF-I receptor; or determining whether the antibody lacks an activity to induce cell proliferation using a cell proliferation test with, e.g., myoblasts. On the other hand, the IGF-I receptor antagonist antibody does not affect glucose uptake by differentiated muscle cells in vitro or the blood glucose level in vivo. Therefore, the IGF-I receptor antagonist antibody of the present invention has a potential as a therapeutic or prophylactic agent without adverse effects such as hyperglycemia, and can be used for treating malignant tumors such as breast cancer, bowel cancer, sarcoma, lung cancer, prostate cancer, thyroid cancer, and myeloma.

[Binding Ability of the Anti-IGF-I Receptor Antibody]

The anti-IGF-I receptor antibody according to the present invention bins to the CR domain of the IGF-I receptor as an epitope. On the other hand, the IGF-I receptor agonist antibody does not have an ability to bind to INSR, which has a high similarity to the IGF-I receptor in primary structure (amino acid sequence) and higher-order structure.

By binding to the CR domain of the IGF-I receptor, the anti-IGF-I receptor antibody according to the present invention is deemed to activate a homo-type receptor, which is a dimer of two copies of the IGF-I receptor, or a hetero-type receptor, which is a dimer between the IGF-I receptor and INSR.

[Sequence of the Anti-IGF-I Receptor Antibody]

The sequence of the anti-IGF-I receptor antibody according to the present invention is not particularly limited, as long as it specifically binds to an IGF-I receptor of a vertebrate and has an activity to induce cell proliferation.

However, the antibody should preferably have specific amino acid sequences as CDR sequences, as will be explained in details below. In the context of the present invention, the term "identity" of amino acid sequences used herein means the ratio of identical amino acid residues between the sequences, while the term "similarity" of amino acid sequences used herein means the ratio of identical or similar amino acid residues between the sequences. The similarity and identity of amino acid sequences can be determined, e.g., using BLAST method (with default conditions of PBLAST provided by NCBI).

The term "similar amino acid residues" used herein means a group of amino acid residues having side chains with similar chemical properties (e.g., electric charge or hydrophobicity). Groups of similar amino acid residues include: 1) amino acid residues having aliphatic side chains: glycine, alanine, valine, leucine, and isoleucine residues;

2) amino acid residues having aliphatic hydroxyl side chains: serine and threonine residues;
3) amino acid residues having amide-containing side chains: asparagine and glutamine residues;
4) amino acid residues having aromatic side chains: phenylalanine, tyrosine, and tryptophan residues;
5) amino acid residues having basic side chains: lysine, arginine, and histidine residues;
6) amino acid residues having acidic side chains: aspartic acid and glutamic acid residues; and
7) amino acid residues having sulfur-containing side chains: cysteine and methionine residues.

According to the present invention, the sequence of CDR-1 of the heavy chain variable region (CDR-H1) should preferably be the amino acid sequence defined in SEQ ID NO:3 (SerTyrTrpMetHis) or an amino acid sequence derived from SEQ ID NO:3 via substitution, deletion or insertion of any one amino acid residue. The sequence of CDR-H1 should also preferably have a similarity of 80% or higher to SEQ ID NO:3. In the context of the present invention, when an amino acid residue (hereinafter "the first amino acid residue") of an amino acid sequence is substituted with another amino acid residue (hereinafter "the second amino acid residue"), the first amino acid residue before the substitution and the second amino acid residue after the substitution should more preferably be similar to each other in structure and/or characteristics.

The sequence of CDR-2 of the heavy chain variable region (CDR-H2) should preferably be the amino acid sequence defined in SEQ ID NO:4 (GluThrAsnProSerAsnSerValThrAsnTyrAsnGluLysPheLysSer) or an amino acid sequence derived from SEQ ID NO:4 via substitution, deletion or insertion of any one or two amino acid residues. The sequence of CDR-H2 should also preferably have a similarity of 82% or higher, particularly 88% or higher, more particularly 94% or higher to SEQ ID NO:4.

The sequence of CDR-3 of the heavy chain variable region (CDR-H3) should preferably be the amino acid sequence defined in SEQ ID NO:5 (GlyArgGlyArgGlyPheAlaTyr) or an amino acid sequence derived from SEQ ID NO:5 via substitution, deletion or insertion of any one or two amino acid residues. The sequence of CDR-H3 should also preferably have a similarity of 75% or higher, particularly 87% or higher to SEQ ID NO:5.

The sequence of CDR-1 of the light chain variable region (CDR-L1) should preferably be the amino acid sequence defined in SEQ ID NO:6 (ArgAlaSerGlnAsnIleAsnPheTrpLeuSer) or an amino acid sequence derived from SEQ ID NO:6 via substitution, deletion or insertion of any one or two amino acid residues. The sequence of CDR-L1 should also preferably have a similarity of 810% or higher, particularly 90% or higher to SEQ ID NO:6.

The sequence of CDR-2 of the light chain variable region (CDR-L2) should preferably be the amino acid sequence defined in SEQ ID NO:7 (LysAlaSerAsnLeuHisThr) or an amino acid sequence derived from SEQ ID NO:7 via substitution, deletion or insertion of any one amino acid residue. The sequence of CDR-L2 should also preferably have a similarity of 85% or higher to SEQ ID NO:7.

The sequence of CDR-3 of the light chain variable region (CDR-L3) should preferably be the amino acid sequence defined in SEQ ID NO:8 (LeuGlnGlyGlnSerTyrProTyrThr) or an amino acid sequence derived from SEQ ID NO:8 via substitution, deletion or insertion of any one or two amino acid residues. The sequence of CDR-L3 should also preferably have a similarity of 77% or higher, particularly 88% or higher to SEQ ID NO:8.

Still more preferably, the anti-IGF-I receptor antibody according to the present invention should have the combination of CDR sequences of:
as the CDR-H1 sequence, the amino acid sequence defined in SEQ ID NO: 3;
as the CDR-H2 sequence, the amino acid sequence defined in SEQ ID NO: 4;
as the CDR-H3 sequence, the amino acid sequence defined in SEQ ID NO: 5;
as the CDR-L1 sequence, the amino acid sequence defined in SEQ ID NO:6;
as the CDR-L2 sequence, the amino acid sequence defined in SEQ ID NO: 7; and
as the CDR-L3 sequence, the amino acid sequence defined in SEQ ID NO: 8.

Methods for identifying the sequence of each of CDR-H1, CDR-H2, CDR-H3, CDR-L1, CDR-L2, and CDR-L3 of an antibody include: Kabat method (Kabat et al., The Journal of Immunology, 1991, Vol. 147, No. 5, pp. 1709-1719) and Chothia method (Al-Lazikani et al., Journal of Molecular Biology, 1997, Vol. 273, No. 4, pp. 927-948). These methods are within the technical common knowledge to persons skilled in the art, the summaries thereof being available, e.g., on the website of Dr. Andrew C. R. Martin's Group (http://www.bioinf.org.uk/abs/).

The framework sequences of immunoglobulin for the antibody of the present invention should preferably be the framework sequences of each class of immunoglobulin of a vertebrate, more preferably the framework sequences of each class of immunoglobulin of a human or a non-human animal including guinea pig, monkey, rabbit, cow, pig, horse, sheep, dog, fowl, mouse, or rat.

The anti-IGF-I receptor antibody according to the present invention should preferably have specific amino acid sequences as the heavy chain variable region and the light chain variable region, as will be specified below.

The heavy chain variable region should preferably have the amino acid sequence defined in SEQ ID NO:9, an amino acid sequence derived from SEQ ID NO:9 via substitution, deletion or insertion of any one or two amino acid residues, or an amino acid sequence having a similarity of 90% or higher to SEQ ID NO:9. The light chain variable region should preferably have the amino acid sequence defined in SEQ ID NO:10, an amino acid sequence derived from SEQ ID NO: 10 via substitution, deletion or insertion of any one or two amino acid residues, or an amino acid sequence having a similarity of 90% or higher to SEQ ID NO:10. The anti-IGF-I receptor antibody according to the present invention should more preferably be IGF11-16, that is, should include the combination of SEQ ID NO:9 as the heavy chain variable region and SEQ ID NO:10 as the light chain variable region.

A person skilled in the art will be able to design a humanized anti-IGF-I receptor antibody according to the present invention by selecting amino acid sequences of CDRs and/or variable regions of a heavy chain and a light chain from those mentioned above and combining them with amino acid sequences of framework regions and/or constant regions of a heavy chain and a light chain of a human antibody as appropriate. Amino acid sequences of framework regions and/or constant regions of a heavy chain and a light chain of a humanized antibody can be selected from, e.g., those of human IgG, IgA, IgM, IgE, and IgD classes or variants thereof.

When the anti-IGF-I receptor antibody according to the present invention is an IGF-I receptor agonist antibody, the antibody of the present invention or its antigen binding fragment should preferably be human IgG class or a variant thereof, more preferably human IgG4 subclass, human IgG1 subclass, or a variant thereof. According to one example, a stabilized IgG4 constant region has proline at position 241 in the hinge region according to Kabat's numbering system. This position corresponds to position 228 in the hinge region according to EU numbering system (Kabat et al., Sequences of Proteins of Immunological Interest, DIANE Publishing, 1992, Edelman et al., Proc. Natl. Acad. Sci USA, 63, 78-85, 1969). The residue at this position in human IgG4 is usually serine, while substitution of serine with proline can induce stabilization of the resultant antibody. According to another example, introduction of N297A mutation into the constant region of IgG1 serves to minimize the ability to bind to the Fc receptor and/or the ability to fix a complement.

[Competitive Binding]

A humanized antibody which causes competitive binding to the IGF-I receptor with the humanized anti-IGF-I receptor antibody according to the present invention is also included in the scope of the present invention. The term "competitive binding" used herein means the phenomenon that when there are two or more monoclonal antibodies together with an antigen, the binding of one of the antibodies to the antigen is inhibited by the binding of the other antibody to the antigen. The competitive binding can usually be measured by, e.g., adding, to a constant amount (concentration) of a monoclonal antibody, another monoclonal antibody with varying the amount (concentration) thereof, and determining the amount (concentration) of the latter monoclonal antibody at which the binding amount of the former monoclonal antibody, existing in the constant amount, is decreased. The degree of inhibition thereof can be expressed in the unit of $IC_{50}$ or Ki. The monoclonal antibody which causes competitive binding with the humanized anti-IGF-I receptor antibody according to the present invention means an antibody having an $IC_{50}$ of 1000 nM or less, particularly 100 nM or less, more particularly 10 nM or less when measuring an antigen-antibody binding using the humanized anti-IGF-I receptor antibody according to the present invention, e.g., the IGF11-16 antibody, at 10 nM. Measurement of competitive binding can also be made by labelling the antibody for use with, e.g., an enzyme, a fluorescent substance, a luminescent substance, a radioactive isotope, etc., and detecting the label using a measurement method suitable for detection of the physical and/or chemical properties of the label.

[Cross-Reaction]

The anti-IGF-I receptor antibody according to the present invention should preferably cross-react with the IGF-I receptor of another vertebrate. The term "cross-reaction" means that while the antibody causes antigen-antibody reaction with the IGF-I receptor from a target animal (such as human), the antibody also has an ability to bind to an antigen derived from another animal different from the target animal. The antibody should preferably has a cross-reactivity with the IGF-I receptor of a different animal from the target animal whose IGF-I receptor is the target of the antigen-antibody reaction by the antibody, such as human or a non-human animal including guinea pig, monkey, rabbit, cow, pig, horse, sheep, dog, or fowl. Example 7 demonstrates that an anti-IGF-I receptor antibody, IGF11-16, was shown to bind to the ProSerGlyPheIleArgAsnGlySer-GlnSerMet (SEQ ID NO: 32) sequence in the CR domain of the human IGF-I receptor. Since this ProSerGlyPheIleArgAsnGlySerGlnSerMet (SEQ ID NO: 32) sequence is conserved in the homologous parts of the IGF-I receptors of monkey (cynomolgus monkey), rabbit, guinea pig, cow, sheep, horse, and dog, this antibody has cross-binding ability to the IGF-I receptors from these species. In addition, since the amino acid sequences of the homologous parts of mouse and rat are both ProSerGlyPheIleArgAsnSerThr-GlnSerMet (SEQ ID NO: 32), screening for an anti-IGF-I receptor antibody which binds to this part makes it possible to obtain an antibody which binds to the IGF-I receptors of, e.g., mouse and rat, and also has similar characteristics and functions as those of IGF11-16.

Alternatively, a cell or an animal of a species which does not cross-react with the anti-IGF-I receptor antibody according to the present invention can be altered via genetic engineering into a cell or an animal expressing an IGF-I receptor with which the anti-IGF-I receptor antibody according to the present invention cross-reacts.

[Activity to Induce Growth of Vertebrate-Derived Cells and Activity to Induce an Increase in the Muscle Mass and/or the Body Length]

An anti-IGF-I receptor antibody according to an embodiment of the present invention has an activity to induce growth of vertebrate-derived cells. Although IGF-I receptor agonist antibodies were already known, no antibody has been reported to show an activity to induce growth primary cultured cells, particularly myoblasts. Also, there has been no known antibody reported so far as having cell growth-inducing activity at a dosage lower than the $EC_{50}$ value of IGF-I in vitro. The vertebrate-derived cells in the context of the present invention should preferably be cells derived from mammals, birds, reptiles, *amphibia*, or fish, more preferably cells derived from mammals or birds, still more preferably cells derived from human, monkey, rabbit, guinea pig, cow, pig, sheep, horse or dog. Cells derived from these species which express an IGF-I receptor with which the anti-IGF-I receptor antibody according to the present invention cross-reacts can be induced to proliferate by the anti-IGF-I receptor antibody according to the present invention. The vertebrate-derived cells according to the present invention also encompass: cells and animals engineered to express an IGF-I receptor of a species with which the anti-IGF-I receptor antibody according to the present invention cross-reacts; and modified animal cells derived from such engineered cells and animals.

An antibody's activity to induce growth of vertebrate-derived cells can be analyzed in vitro using primary cultured cells, established cell lines, or transformants derived from such cells. The term "primary cultured cells" means cells which were isolated from an organ or a tissue of a living organism, and can typically be subcultured for some passages. Primary cultured cells derived from a vertebrate can be obtained from an organ or a tissue of the vertebrate via enzyme treatment, dispersion with physical means, or explant method. An organ or a tissue or a fragment thereof obtained from the vertebrate can also be used for analyzing the antibody's activity above. Preferable examples of organs and tissues from which primary cells are prepared include: endocrine tissues such as thyroid, parathyroid, and adrenal gland; immune tissues such as appendix, tonsil, lymph nodes, and spleen; respiratory organs such as trachea and lung; digestive organs such as stomach, duodenum, small intestine, and large intestine; urinary organs such as kidney and urinary bladder; male genital organs such as vas deferens, testicle, and prostate; female genital organs such as breast and fallopian tube; and muscle tissues such as heart muscle and skeletal muscles. More preferable examples include liver, kidney, or digestive organs or muscle tissues, among which muscle tissues are still more preferable. Primary cultured cells which can be used for analyzing the growth-inducing activity of an anti-IGF-I receptor antibody in the context of the present invention are cells which express an IGF-I receptor and can be induced to proliferate by IGF-I binding to the IGF-I receptor. Typical examples thereof are skeletal muscle myoblasts, which are primary cultured cells isolated from muscle tissue. Human- or animal-derived primary cultured cells available by assignment or commercially on the market can also be obtained and used. Human primary cultured cells are available from various institutions and companies, e.g., ATCC, ECACC, Lonza, GIBCO, Cell Applications, ScienCell research laboratories, and PromoCell.

The term "cell line" means a line of cultured cells which were derived from a living organism and then immortalized such that they can semipermanently proliferate with maintaining their specific properties. Cell lines are divided into non-tumor-derived cell lines and tumor-derived cell lines. Vertebrate-derived cell lines which can be used for analyzing the growth-inducing activity of the anti-IGF-I receptor antibody according to the present invention are cells which express an IGF-I receptor and can be induced to proliferate by IGF-I binding to the IGF-I receptor. Examples of cell lines which express an IGF-I receptor and can be induced to proliferate by IGF-I include, although not limited to: human neuroblastoma SH-SY5Y, human epidermal keratinocyte line HaCaT, human alveolar basal epithelial adenocarcinoma cell line A549, human colon-adenocarcinoma cell line Caco-2, human hepatocellular cancer cell line HepG2, human cervical cancer cell line Hela, human cervical cancer cell line SiHa, human breast cancer cell line MCF7, human pluripotent human embryonal carcinoma line NTERA-2, and human bone cancer cell line U-2-OS.

Other cells which can be used for analyzing the growth-inducing activity of the anti-IGF-I receptor antibody according to the present invention are transformants derived from primary cultured cells and cell lines. Examples of such transformants include: iPS cells produced from primary cultured cells; and cells and tissues differentiated from such iPS cells. Other transformants include primary cultured cells and cell lines engineered to incorporate a gene so as to transiently or permanently express the gene. Examples of genes to be introduced into and expressed by such cells include IGF-I receptor genes of human and other species.

Methods for determining the ability of the anti-IGF-I receptor antibody according to the present invention to induce vertebrate-derived cells to proliferate include: cell counting, measurement of DNA synthesis, and measurement of change in the metabolic enzyme activity. Methods for cell counting include methods using blood cell counting plates or cell counting devices such as Coulter counters. Methods for measuring DNA synthesis include methods based on uptake of [3H]-thymidine or 5-bromo-2'-deoxyulysine (BrdU). Method for measuring the change in metabolic enzyme activity include MTT method, XTT method, and WST method. A person skilled in the art could also employ other methods as appropriate. An activity to induce cell proliferation is detected if the growth of the cultured cells reacted with the anti-IGF-I receptor antibody according to the present invention is higher than the growth of the cells in the absence of the antibody. In this case, it is convenient to also measure the induction activity under the same conditions using IGF-I, which is an original legand for the IGF-I receptor, as a control.

The cultured cells to be tested are reacted with either the anti-IGF-I receptor antibody according to the present invention or IGF-I with varying its concentration, and the concentration at which 50% of the maximum growth activity is exhibited is determined as an $EC_{50}$ value. When human skeletal muscle myoblasts are used for evaluating the growth activity, the $EC_{50}$ value of the anti-IGF-I receptor antibody according to the present invention for inducing cell proliferation should preferably be comparable to that of IGF-I, more preferably 1/10 or less of that of IGF-I, still more preferably 1/20 or less, still further more preferably 1/50 or less of that of IGF-I. When human skeletal muscle myoblasts are used for evaluating the growth activity, the $EC_{50}$ value of the anti-IGF-I receptor antibody according to the present invention should preferably be 0.5 nmol/L or less, more preferably 0.3 nmol/L or less, still more preferably 0.1 nmol/L or less.

Methods for measuring the activity to induce growth of vertebrate-derived cells in vivo include: a method involving parenterally administering the anti-IGF-I receptor antibody according to the present invention to a vertebrate and measuring changes in the weight, size, cell count, etc., for the entire body of the individual which received the administration or for an organ or a tissue isolated from the individual; and a method involving using an animal with a graft of vertebrate cells and measuring changes in the weight, size, cell count, etc., of the graft including vertebrate cells. Measurements for the entire body of an individual include: measurements of the body weight, the body length, and the circumferences of four limbs; measurement of the body composition, using impedance method; and measurement of the creatinine height coefficient. Measurements for an organ, a tissue, or a graft from an individual include: in the case of a non-human animal, a method involving directly recovering the target organ, tissue or graft and measuring its weight, size, or the number of cells included therein. Non-invasive measurements for an organ, a tissue, or a graft from an individual include: image analysis using X-ray photography, CT, and MRI; and contrast methods using tracers with isotopes or fluorescent substances. If the target tissue is skeletal muscle, then a change in the muscle force can also be used as an indicator. A person skilled in the art could also employ any other methods as appropriate for analyzing the activity of the anti-IGF-I receptor antibody according to the present invention to induce growth of vertebrate-derived cells in vivo. Methods for measuring the activity of the anti-IGF-I receptor antibody according to the present invention to induce growth of vertebrate-derived cells in vivo include: carrying out measurements using, e.g., the methods mentioned above for individuals who received administration of the anti-IGF-I receptor antibody according to the present invention and individuals who received administration of a different antibody other than the anti-IGF-I receptor antibody according to the present invention or any other control substance, and comparing the resultant measurements between these individuals.

The anti-IGF-I receptor antibody according to the present invention is characterized by having a longer duration of cell-growth inducing effect relative to the time of contact with the cells compared to the duration of the wild-type IGF-I, and thereby exhibits improved sustainability. According to Example 12, which demonstrates cell proliferation induction activities in vitro, when cells were contacted with the wild-type IGF-I and then washed with culture medium without IGF-I, the cell proliferation induction activity of the wild-type IGF-I disappeared after the washing. On the other hand, when cells were contacted with IGF11-16 (anti-IGF-I receptor antibody according to the present invention) and then washed with culture medium without IGF11-16, the cell growth-inducing activity continued even after the washing. According to Example 16, which compares the kinetics of IGF-I and IGF11-16 (anti-IGF-I receptor antibody according to the present invention) in blood, about 50% or higher of the wild-type IGF-I administered to an animal disappeared from the blood within 24 hours after the administration, while 60% or higher of the IGF11-16 antibody administered to an animal remained in the blood even 48 hours after the administration. Thus, the IGF11-16 antibody was shown to remain in the blood for a long time. These results indicate that the anti-IGF-I receptor antibody according to the present invention exhibits a long-term effect of inducing cell proliferation both in vitro and in vivo.

The anti-IGF-I receptor antibody according to the present invention is also expected to exhibit an in vivo effect of increasing the muscle mass and/or the body length. Specifically, IGF-I has an effect of inducing the growth and differentiation of myoblasts in skeletal muscles as mentioned above, as well as an effect of broadening muscle fibers. It is expected that these effects collectively lead to the effect of increasing the muscle mass. Like IGF-I, when the anti-IGF-I receptor antibody according to the present invention is administered to an animal, it also exhibits an effect of increasing the muscle mass of the animal. The anti-IGF-I receptor antibody according to the present invention is the first IGF-I receptor agonist antibody which has been shown to exhibit an in vivo effect of increasing the muscle mass.

Methods for measuring the activity of the anti-IGF-I receptor antibody according to the present invention to increase the muscle mass include: for the entire body of the individual which received the administration, measurement of the body weight, the body length, and the circumferences of four limbs; measurement of the body composition, using impedance method; and measurement of the creatinine, and height coefficient. Other methods include: image analysis using X-ray photography, CT, and MRI; contrast methods using tracers with isotopes or fluorescent substances; and measurement of a change in the muscle force. In the case of a non-human animal, a method involving directly recovering the target organ, tissue or graft and measuring its weight and/or size can also be used. The effect of increasing the muscle mass can be evaluated by: comparing the muscle mass increases between an individual to which the anti-IGF-I receptor antibody according to the present invention was administered and an individual to which the antibody was not administered; or comparing the muscle masses of an individual before and after administration of the anti-IGF-I receptor antibody according to the present invention. The effect of increasing the muscle mass can be determined if there is any increase in the muscle mass of an individual before and after the administration of the anti-IGF-I receptor antibody according to the present invention. Preferably, the effect achieved by administration of the anti-IGF-I receptor antibody according to the present invention can be determined when there is a difference of preferably 103% or higher, more preferably 104% or higher of the muscle mass between an individual to which the anti-IGF-I receptor antibody according to the present invention was administered and an individual to which the antibody was not administered, or of the same individual between before and after administration of the anti-IGF-I receptor antibody according to the present invention. IGF-I also plays a role in the bone growth, and has an effect of increasing the body length (the body height in the case of the human). Therefore, the anti-IGF-I receptor antibody according to the present invention also exhibits an effect of increasing the body length when administered to an animal. The effect of the anti-IGF-I receptor antibody according to the present invention in increasing the body length of an individual can be determined by measuring the body weight, the body length, and the circumferences of four limbs of the individual.

[Effects on the Glucose Uptake by Vertebrate-Derived Cells and/or the Blood Glucose Level of an Animal]

An anti-IGF-I receptor antibody according to an embodiment of the present invention is characterized by not affecting the intracellular glucose uptake by differentiated muscle cells derived from a vertebrate and/or the blood glucose level of a vertebrate. Specifically, IGF-I is known to has an effect of increasing the intracellular glucose uptake and an effect of lowering the blood glucose level as part of its agonist effects to the IGF-I receptor. On the other hand, although the anti-IGF-I receptor antibody of the present invention functions as an agonist of an IGF-I receptor antibody, it unexpectedly does not induce the glucose uptake by differentiated muscle cells even at a dosage of 100 times or more as high as the in vitro $EC_{50}$ value for cell growth-inducing activity. More particularly, when parenterally administered to an animal at a dosage of 10 times or more as high as the effective dosage sufficient to induce a muscle mass increase, the antibody unexpectedly does not alter the blood glucose level. In addition, as properties as an IGF-I receptor antagonist antibody, its characteristics of not affecting the intracellular glucose uptake by differentiated muscle cells derived from a vertebrate and/or the blood glucose level of a vertebrate are advantageous effects which serve to avoid the problem of causing hyperglycemia, which problem was desired to be solved for the antibody to be used for human therapy, but was not solved by conventional IGF-I receptor antagonist antibodies. The vertebrate-derived cells according to the present invention should preferably be cells derived from mammals, birds, reptiles, *amphibia* or fish, more preferably cells derived from mammals or birds, still more preferably cells derived from human, monkey, rabbit, guinea pig, cow, pig, sheep, horse or dog. The vertebrate-derived cells according to the present invention also encompasses: cells and animals engineered to express an IGF-I receptor derived from a vertebrate species having a cross-reactivity with the anti-IGF-I receptor antibody according to the present invention; cells and animals engineered to express an IGF-I receptor mutated so as to has a binding ability; and cells derived from such engineered animals.

In order to analyze the effect of the anti-IGF-I receptor antibody of the present invention in not affecting the intracellular glucose uptake by vertebrate-derived cells in vitro, it is possible to use primary cultured cells, cell lines, and transformants derived from such cells. The term "primary cultured cells" means cells which were isolated from an organ or a tissue of a living organism, and can typically be subcultured for some passages. Primary cultured cells derived from a vertebrate can be obtained from an organ or a tissue of the vertebrate via enzyme treatment, dispersion with physical means, or explant method. Preferable examples of organs and tissues from which primary cells are prepared include: endocrine tissues such as thyroid, parathyroid, and adrenal gland; immune tissues such as appendix, tonsil, lymph nodes, and spleen; respiratory organs such as trachea and lung; digestive organs such as stomach, duodenum, small intestine, and large intestine; urinary organs such as kidney and urinary bladder; male genital organs such as vas deferens, testicle, and prostate; female genital organs such as breast and fallopian tube; and muscle tissues such as heart muscle and skeletal muscles. More preferable examples include liver, kidney, or digestive organs or muscle tissues, among which muscle tissues are still more preferable.

Primary cultured cells which can be used for analyzing the feature of an anti-IGF-I receptor antibody for not affecting the intracellular glucose uptake in the context of the present invention are cells which express an IGF-I receptor and can be induced to cause intracellular glucose uptake by IGF-I binding to the IGF-I receptor. Typical examples thereof are muscle cells differentiated from skeletal muscle myoblasts, which are primary cultured cells isolated from muscle tissue.

The "differentiated muscle cells" of the present invention are muscle cells which have caused differentiation, and include those which have not been completely differentiated. For the sake of convenience, the term "differentiated muscle cells" in the context of the present invention refers to cells which have experienced differentiation for at least about six days from the start of differentiation. Human- or animal-derived primary cultured cells available by assignment or commercially on the market can also be obtained and used. Human primary cultured cells are available from various institutions and companies, e.g., ATCC, ECACC, Lonza, GIBCO, Cell Applications, ScienCell research laboratories, and PromoCell.

The term "cell line" means a line of cultured cells which were derived from a living organism and then immortalized such that they can semipermanently proliferate while maintaining their specific properties. Cell lines are divided into non-tumor-derived cell lines and tumor-derived cell lines. Vertebrate-derived cell lines which can be used for analyzing the effect of the anti-IGF-I receptor antibody according to the present invention on the intracellular glucose uptake are cells which express an IGF-I receptor and can be induced to cause intracellular glucose uptake by IGF-I binding to the IGF-I receptor. Examples of cell lines which express an IGF-I receptor and can be induced to cause intracellular glucose uptake by IGF-I include, although not limited to: skeletal muscle cells, fat cells, and epidermal keratinocytes.

Other cells which can be used for analyzing the effect of the anti-IGF-I receptor antibody according to the present invention on the intracellular glucose uptake are transformants derived from primary cultured cells and cell lines. Examples of such transformants include: iPS cells produced from primary cultured cells; and cells and tissues induced to differentiate from such iPS cells. Other transformants include primary cultured cells and cell lines engineered to incorporate a gene so as to transiently or permanently express the gene. Examples of genes to be introduced into and expressed by such cells include IGF-I receptor genes of human and other species.

Methods for determining the effect of the anti-IGF-I receptor antibody according to the present invention on the glucose uptake by vertebrate-derived cells include: measurement of the intracellular glucose concentration; measurement of the intracellular uptake of a glucose analog tracer substance; and measurement of a change in the amount of a glucose transporter. Methods for measuring the glucose concentration include absorbance measurement methods such as enzyme method. Methods for measuring the intracellular uptake amount of a glucose analog tracer substance include measurement of the uptake amount of [3H]-2'-deoxyglucose. Methods for measuring a change in the amount of a glucose transporter include immunocytostaining and western blotting. A person skilled in the art could also employ other methods as appropriate. The fact that there is no effect on the intracellular glucose uptake can be confirmed if the intracellular glucose uptake of the cultured cells reacted with the anti-IGF-I receptor antibody according to the present invention is almost the same of the intracellular glucose uptake of the cultured cells in the absence of the antibody. In this case, it is convenient to also carry out the measurement under the same conditions using IGF-I, which is an original legand for the IGF-I receptor, as a control.

The cultured cells to be tested are treated with either the anti-IGF-I receptor antibody according to the present invention or IGF-I with varying its concentration, and the glucose uptake of the treatment group is indicated as a percentage when the intracellular glucose uptake of the non-treatment group is determined as 100%. When human differentiated muscle cells are used for evaluating the glucose uptake, the glucose uptake achieved by the anti-IGF-I receptor antibody according to the present invention should preferably be equal to or less than the glucose uptake achieved by IGF-I at the same concentration. More preferably, the glucose uptake achieved by the anti-IGF-I receptor antibody according to the present invention should be 110% or less, still more preferably 100%, of the glucose uptake amount of the non-treatment group. When human differentiated muscle cells are used for evaluating the glucose uptake, the glucose uptake achieved by the anti-IGF-I receptor antibody according to the present invention added at an amount of 100 nmol/L should preferably be 110% or less, more preferably 105% or less, still more preferably from 95% to 100%.

Methods for determining the glucose uptake by vertebrate-derived cells in vivo include: methods involving parenterally administering the anti-IGF-I receptor antibody according to the present invention to a vertebrate and determining a change in the glucose content of an organ or a tissue of the individual. Methods of measurement for the entire body of the individual which received the administration include: measurement of the blood glucose level; and hemoglobin A1C using glycosylated proteins as indicators. Methods of measuring the glucose uptake for an organ or a tissue of an individual include: in the case of a non-human animal, directly recovering the target organ or tissue, and calculating the concentration of glucose or a tracer. Non-invasive methods for measuring the glucose uptake individual for an organ or a tissue of an individual include: image analysis using X-ray photography, CT, and MRI; and contrast methods using tracers with isotopes or fluorescent substances. If the target tissue is a skeletal muscle, then the glucose clamp can also be used as an indicator. A person skilled in the art could also employ any other methods as appropriate for analyzing the effect of the anti-IGF-I receptor antibody according to the present invention on the glucose uptake by vertebrate-derived cells in vivo.

The anti-IGF-I receptor antibody according to the present invention is also characterized in that when parenterally administered to a vertebrate even at an effective dosage sufficient to increase the muscle mass of the vertebrate, preferably at a dosage of 10 times or more the effective dosage, it does not change the blood glucose level of the vertebrate. When evaluating the effect of the anti-IGF-I receptor antibody of the present invention in changing the blood glucose level of a vertebrate, it is preferred to use an animal belonging to mammals, birds, reptiles, *amphibia* or fish, more preferably an animal belonging to mammals or birds, still more preferably human, monkey, rabbit, guinea pig, cow, pig, sheep, horse or dog. An animal engineered to express an IGF-I receptor of a species which has cross-reactivity with the anti-IGF-I receptor antibody according to the present invention can also be used as an animal for evaluating the effect of the anti-IGF-I receptor antibody of the present invention in changing the blood glucose level. Invasive methods for measuring the blood glucose level include colorimetric method and electrode method. Examples of enzyme methods used for detection include glucose oxidase method (GOD method) and glucose dehydrogenase method (GDH method). Non-invasive methods include optical measurement methods. A person skilled in the art can also select any other method as appropriate. In the case of human, the normal range of fasting blood glucose level is from 100 mg/dL to 109 mg/dL. With regard to adverse events in the blood glucose level resulting from a drug administration (Common Terminology Criteria for Adverse Events v4.0), the blood glucose level of lower than the range of from 77 mg/dL to 55 mg/dL is defined as an indicative of low blood glucose, while a blood glucose level of higher than the range of from 109 mg/dL to 160 mg/dL is defined as an indicative of high blood glucose. A drug administration is considered as not affecting the blood glucose level when the blood glucose level after the drug administration is higher than 55 mg/dL and lower than 160 mg/dL, more preferably higher than 77 mg/dL and lower than 109 mg/dL. However, the normal value of blood glucose level and its range of fluctuation vary depending on the animal to which a drug is administered, and even a human subject may not always have a blood glucose level within a normal range at the time of the drug administration. Accordingly, in the context of the present invention, the anti-IGF-I receptor antibody according to the present invention should preferably be considered as not changing the blood glucose level of a vertebrate to which the antibody is administered when the change in the blood glucose level of the vertebrate is preferably 30% or less, more preferably 20% or less, still more preferably 10% or less.

[Process for Producing the Anti-IGF-I Receptor Antibody]

The antibody according to the present invention can be produced using various techniques well-known to a person skilled in the art. Specifically, the antibody according to the present invention may be a polyclonal antibody or a monoclonal antibody (Milstein et al., Nature (England), Oct. 6, 1983, Vol. 305, No. 5934, pp. 537-540). A polyclonal antibody according to the present invention can be obtained, for example, by sensitizing a mammal with a peptide of the IGF-I receptor defined in SEQ ID NO:2 as an antigen, and recovering the resultant antibody from, e.g., the animal's serum. When the peptide is used as an antigen, the peptide may be bound to a carrier protein such as BSA or KLH or coupled with polylysine. Specific examples of peptides which can be used as an antigen include, although not limited thereto, ProSerGlyPheIleArgAsnGlySerGlnSerMet (SEQ ID NO: 32), a partial sequence of SEQ ID NO:2. A monoclonal antibody according to the present invention can be obtained, for example, by sensitizing a mammal with such an antigen, recovering an immune cell from the mammal, and fusing the immune cell with a myeloma cell to produce a hybridoma, cloning and culturing the hybridoma, and recovering the resultant antibody from the cultured hybridoma. An example of such a method for obtaining a monoclonal antibody is described in Example 1, and examples of monoclonal antibodies obtained thereby include, although not limited thereto, a monoclonal antibody having the VH amino acid sequence defined in SEQ ID NO:9 and the VL amino acid sequence defined in SEQ ID NO:10 (IGF11-16).

Once such a monoclonal antibody is obtained, then a nucleic acid molecule having a gene sequence encoding the amino acid sequence of the antibody protein, and such a nucleic acid molecule can also be used for producing the antibody via genetic engineering technique. A person skilled in the art would appreciate various techniques for utilizing gene information about the antibody, such as information of the H chain and the L chain, the variable regions thereof, and the CDR sequences, for modifying the antibody in order to improve its binding ability or specificity, or altering an animal antibody such as a mouse antibody into a human-type antibody, to thereby prepare an antibody having a structure suitable as a therapeutic agent for human. A human-type monoclonal antibody can also be prepared by using, as an animal to be sensitized with an antigen, a non-human transgenic animal into which a human antibody gene has been introduced. Another method which does not require sensitization of an animal is a technique involving using a phage library expressing an antigen binding region of a human antibody or a part thereof (human antibody phage display) and obtaining a phage clone expressing a peptide which specifically binds to a corresponding antigen or an antibody having a desired amino acid sequence, and producing a desired human antibody based on the information of the selected phage clone. A person skilled in the art can employ such a technique as appropriate (see, e.g., a review by Taketo Tanaka et al., Keio J. Med., Vol. 60, pp. 37-46).

A method for producing a monoclonal antibody as mentioned above includes culturing a hybridoma which produces the desired antibody and purifying the resultant antibody from the culture supernatant via conventional means. Another method for producing a monoclonal antibody as mentioned above includes providing a hybridoma which produces the desired antibody or a phage clone obtained from a human antibody phage display, obtaining a gene encoding such an antibody, more specifically, a gene encoding a heavy chain and/or a light chain of immunoglobulin, preparing a vector expressing the gene, and introducing the vector into a host cell (mammal cell, insect cell, microorganism, etc.) for production of the antibody. A person skilled in the art could also modify this method by genetically engineering the gene encoding a heavy chain and/or a light chain of immunoglobulin for introducing a desired trait, and producing a humanized antibody, an antibody chimeric protein, a low-molecular antibody, or a scaffold antibody using structure information about variable regions or CDR regions of a heavy chain and/or a light chain of immunoglobulin, by using known techniques. In order to improve the performance of the antibody or avoid adverse effects, a person skilled in the art could also introduce an alteration into the structures of constant regions or sugar chains of the antibody, by using techniques well-known to a person skilled in the art.

The anti-IGF-I receptor antibody according to the present invention can be obtained using a method well-known to persons skilled in the art. Specifically, while the humanized anti-IGF-I receptor antibody according to the present invention is typically a monoclonal antibody (Milstein et al., Nature, 1983, Vol. 305, No. 5934, pp. 537-540), such a monoclonal antibody can be prepared by, e.g., the following method.

This method starts with, for example, preparation of a nucleic acid molecule encoding the amino acid sequence(s) of a heavy chain and/or a light chain constituting an immunoglobulin of the anti-IGF-I receptor antibody according to the present invention. The nucleic acid molecule may then be cloned into various vector or plasmids to produce a vector or plasmid containing the nucleic acid molecule. Next, the nucleic acid molecule, vector, or plasmid is used to transform a host cell, which may be selected from, e.g., eukaryotic cells such as mammal cells, insect cells, yeast cells, and plant cells, and bacterium cells. The transformed host cell is then cultured under appropriate conditions which can allow production of the anti-IGF-I receptor antibody according to the present invention. If necessary, the resultant anti-IGF-I receptor antibody according to the present invention may be isolated from the host cell. Various methods that can be used for this procedure are well-known to persons skilled in the art.

A method based on immunization of an animal includes preparing a non-human transgenic animal into which a human antibody gene has been introduced as the subject animal to be immunized, immunizing the animal using the IGF-I receptor and/or its partial peptide as an antigen, recovering an immune cell from the animal and fusing it with a myeloma cell to form a hybridoma, which is then cloned to produce an antibody, which is then recovered from the culture supernatant using a routine purification procedure. Example of such a method of obtaining a monoclonal antibody is described in, e.g., WO2013/180238A.

Another available method includes using a phage library expressing a variable region of a desired humanized antibody or a part thereof (human antibody phage display) to thereby obtain an antibody which specifically binds to a corresponding antigen or a phage clone having a specific amino acid sequence, whose information is then used for producing the desired humanized antibody (see, e.g., the review by Taketo Tanaka et al., The Keio Journal of Medicine, Vol. 60, pp. 37-46)

In this connection, a person skilled in the art can produce various antibodies such as antibody chimeric proteins, low molecule antibodies, and scaffold antibodies using known techniques, e.g., by making a genetic modification to a gene encoding a heavy chain and/or a light chain of an immunoglobulin for introducing a desired trait, or by using structure information of variable regions or CDR regions of a heavy chain and/or a light chain of an immunoglobulin. In addition, in order to improve the performance of the antibody or avoiding side effects, it is possible to introduce a modification into the structure of a constant region of an antibody or to introduce glycosylation sites of an antibody, using techniques well-known to persons skilled in the art as appropriate.

[Drug Containing the Anti-IGF-I Receptor Antibody]

The anti-IGF-I receptor antibody according to the present invention can be used as a therapeutic or prophylactic agent for a condition associated with IGF-I or a disease caused by any effect on an IGF-I receptor. Specifically, conditions associated with IGF-I or diseases that can be the target of therapy or prevention using the IGF-I receptor agonist antibody include: disuse muscle atrophy, dwarfism, hepatic cirrhosis, hepatic fibrosis, diabetic nephropathy, chronic renal failure, Laron syndrome, aging, intrauterine growth restriction (IUGR), cardiovascular protection, diabetes, insulin resistant, metabolic syndrome, osteoporosis, cystic fibrosis, myotonic dystrophy, AIDS-associated sarcopenia, HIV-associated fat redistribution syndrome, Crohn's disease, Werner's syndrome, X-linked combined immunodeficiency disease, hearing loss, anorexia nervosa and retinopathy of prematurity, Turner's syndrome, Prader-Willi syndrome, Silver-Russell syndrome, idiopathic short stature, obesity, multiple sclerosis, ulcerous colitis, low muscle mass, myocardial ischemia, and decreased bone density. Diseases that can be the target of therapy or prevention using the IGF-I receptor antagonist antibody include: neuroblastoma, striated muscle sarcoma, bone cancer, childhood cancer, acromegalia, ovary cancer, pancreas cancer, benignant prostatic hypertrophy, breast cancer, prostate cancer, bone cancer, lung cancer, colorectal cancer, cervix cancer, synovial sarcoma, urinary bladder cancer, stomach cancer, Wilms' tumor, diarrhea associated with metastatic carcinoid and vasoactive intestinal peptide secreting tumor, vipoma, Verner-Morrison syndrome, Beckwith-Wiedemann syndrome, kidney cancer, renal cell cancer, transitional cell cancer, Ewing's sarcoma, leukemia, acute lymphoblastic leukemia, brain tumor, glioblastoma, non-glioblastomatic brain tumor, meningioma, pituitary adenoma, vestibular schwannoma, primitive neuroectodermal tumor, medulloblastoma, astrocytoma, oligodendroglioma, ependymoma, choroid plexus papilloma, gigantism, psoriasis, atherosclerosis, vascular smooth muscle restenosis, inappropriate microvascular growth, diabetic retinopathy, Graves' disease, systemic lupus erythematosus, chronic thyroiditis, myasthenia gravis, autoimmune thyroiditis, and Behcet's disease. Particularly preferred uses of the anti-IGF-I receptor antibody according to the present invention include use as a therapeutic or prophylactic agent of disuse muscle atrophy and/or dwarfism. The anti-IGF-I receptor antibody according to the present invention is advantageous in that it does not change the blood glucose level upon administration.

A drug containing the anti-IGF-I receptor antibody according to the present invention may be formulated in the form of a pharmaceutical composition which contains, in addition to the anti-IGF-I receptor antibody according to the present invention, a pharmaceutically acceptable carrier and/or any other excipient. Drug formulation using a pharmaceutically acceptable carrier and/or any other excipient can be carried out in accordance with, e.g., a method described in the University of the Sciences in Philadelphia, "Remington: The Science and Practice of Pharmacy, 20th EDITION", Lippincott Williams & Wilkins, 2000. Such a therapeutic or prophylactic agent may be provided as a liquid formulation prepared by dissolving, suspending, or emulsifying the ingredients into sterile aqueous medium or oily medium, or as a lyophilized formulation thereof. A medium or solvent as a diluent for preparing such a formulation may be an aqueous medium, examples of which include distilled water for injection and physiological saline solution, which may optionally be used with addition of an osmoregulating agent (e.g., D-glucose, D-sorbitol, D-mannitol, and sodium chloride), and/or in combination with a suitable dissolving aid such as an alcohol (e.g., ethanol), a polyalcohol (e.g., propylene glycol or polyethylene glycol), or a nonionic surfactant (e.g., polysorbate 80 or polyoxyethylene hydrogenated castor oil 50). Such a formulation can also be prepared with an oily medium or solvent, examples of which include sesame oil and soybean oil, which can optionally be used in combination with a dissolving aid such as benzyl benzoate and benzyl alcohol. Such liquid drugs may often be prepared using appropriate additives such as buffering agents (e.g., phosphate buffering agents and acetate buffering agents), soothing agents (e.g., benzalkonium chloride and procaine hydrochloride), stabilizers (e.g., human serum albumin and polyethylene glycol), preservatives (e.g., ascorbic acid, erythorbic acid, and their salts), coloring agents (e.g., copper chlorophyll P-carotene, Red #2 and Blue #1), antiseptic agents (e.g., paraoxybenzoic acid esters, phenol, benzethonium chloride and benzalkonium chloride), thickeners (e.g., hydroxypropyl cellulose, carboxymethyl cellulose, and their salts), stabilizers (e.g., human serum albumin mannitol and sorbitol), and odor correctives (e.g., menthol and citrus aromas). Other alternative forms include therapeutic agents or prophylactic agent for application onto mucous membranes, such formulations often containing additives such as pressure-sensitive adhesives, pressure-sensitive enhancers, viscosity regulators, thickening agents and the like (e.g., mucin, agar, gelatin, pectin, carrageenan, sodium alginate, locust bean gum, xanthan gum, tragacanth gum, gum arabic, chitosan, pullulan, waxy starch, sucralfate, cellulose and its derivatives (such as hydroxypropyl methyl cellulose), polyglycerol fatty acid esters, acrylic acid-alkyl (meth)acrylate copolymers, or their salts and polyglycerol fatty acid esters), primarily for the purpose of imparting mucosal adsorption or retention properties. However, the form, solvent and additives for the therapeutic agent or prophylactic agent to be administered to the body are not limited to these, and appropriately selection may be made by a person skilled in the art.

A drug containing the anti-IGF-I receptor antibody according to the present invention may further contain, in addition to the anti-IGF-I receptor antibody according to the present invention, another known agent (active ingredient). A drug containing the anti-IGF-I receptor antibody according to the present invention may be combined with another known agent in the form of a kit. Examples of active ingredients to be combined with the IGF-I receptor agonist antibody include: growth hormone or an analog thereof, insulin or an analog thereof, IGF-II or an analog thereof, an anti-myostatin antibody, myostatin antagonist, anti-activin type IIB receptor antibody, activin type IIB receptor antagonist, soluble activin type IIB receptor or an analog thereof, ghrelin or an analog thereof, follistatin or an analog thereof, a beta-2 agonist, and a selective androgen receptor modulator. Examples of active ingredients to be combined with the IGF-I receptor antagonist antibody include: corticosteroid, antiemetic, ondansetron hydrochloride, granisetron hydrochloride, metoclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesic, ibuprofen, naproxen, choline magnesium trisalicylate, oxycodone hydrochloride, anti-angiogenic, antithrombotic, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGFantibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative, farnesyl protein transferase inhibitor, alpha v beta 3 inhibitor, alpha v beta 5 inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38. The dosage of the other agent used in combination with the anti-IGF-I receptor antibody may be within a dosage used for normal therapy, but can be increased or decreased depending on the situation.

The therapeutic or prophylactic agent according to the present invention can be parenterally administered for the purpose of improving symptoms. For parenteral administration, a transnasal agent may be prepared, and a liquid drug, suspension or solid formulation may be selected. An injection may be prepared as a different form of parenteral administration, the injection being selected as subcutaneous injection, intravenous injection, infusion, intramuscular injection, intracerebroventricular injection or intraperitoneal injection. Other formulations used for parenteral administration include suppositories, sublingual agents, percutaneous agents and transmucosal administration agents other than transnasal agents. In addition, intravascular local administration is possible by a mode of addition or coating onto a stent or intravascular obturator.

The dose for an agent for treatment or prevention according to the invention will differ depending on the patient age, gender, body weight and symptoms, the therapeutic effect, the method of administration, the treatment time, or the types of active ingredients in the medical composition, but normally it may be administered in the range of 0.1 mg to 1 g and preferably in the range of 0.5 mg to 300 mg of active compound per administration for adults, once every one to four weeks, or once every one to two months. Thus, the administration should preferably be carried out less than once weekly. However, since the administration dose and frequency will vary depending on a variety of conditions, lower administration dose and fewer administration frequency than those mentioned above may be sufficient, or administration dose and frequency exceeding these ranges may be necessary.

[Uses for Non-Human Animals]

An anti-IGF-I receptor antibody according to an embodiment of the present invention can be used for livestock or veterinary applications on non-human animals. Animals being the target of the anti-IGF-I receptor antibody according to the present invention for livestock or veterinary applications should preferably be non-human animals belonging to mammals, birds, reptiles, *amphibia* or fish, more preferably non-human animals belonging to mammals or birds, still more preferably an animal selected from monkey, rabbit, guinea pig, cow, pig, sheep, horse or dog. Although cow growth hormones and pig growth hormones are currently used for increasing milk production of cows and for promoting growth of piglets, respectively, these effects are considered to be achieved by IGF-I, whose expression is induced by a growth hormone (see H. Jiang and X. Ge, Journal of Animal Science, Vol. 92, pp 21-29, 2014). Therefore, the agonist effects of the anti-IGF-I receptor antibody according to the present invention can be utilized for the purposes of enhancing milk production of an animal and promoting growth of a fetus or a new-born baby animal. Examples of other applications for which the anti-IGF-I receptor antibody according to the present invention can be used include, although not limited to: increasing the muscle mass of an animal, increasing the weight ratio of muscles to fat of an animal, increasing the transformation efficiency of fed diet into tissues of the body, increasing the reproductive efficiency, enhancing the reproduction ability of an species for preservation thereof, and treating trauma and exhaustive symptoms involved in debilitating diseases. The antagonist effect achieved by another embodiment of the anti-IGF-I receptor antibody according to the present invention can be utilized for treating malignant tumor of an animal, controlling the reproduction frequency of an animal, controlling the growth of an individual, and other uses. A person skilled in the art could also modify the structure of the anti-IGF-I receptor antibody according to the present invention as appropriate to alter the amino acid sequences of the frameworks or constant regions of the antibody and to thereby decrease its immunogenicity, depending on the animal species to which the antibody is administered.

[Method for Culturing Cells Using the Anti-IGF-I Receptor Antibody]

IGF-I and its derivatives are widely used in cell culture techniques for maintaining, growing, and/or differentiating vertebrate-derived cells in vitro, and commercially marketed as cell culture reagents. However, since IGF-I can lose its effects during long-term culturing due to, e.g., its lack of sufficient stability, it is necessary to, e.g., keep adjusting the concentration thereof in order to carry out cell culturing stably. In addition, since IGF-I induces glucose uptake by cells, there is a possibility that the metabolism and characteristics of the cells may be changed due to an increase in the intracellular glucose concentration, and that the culture conditions may change due to a decrease in the glucose concentration of the culture medium. Compared to IGF-I, the anti-IGF-I receptor antibody according to the present invention is characterized in that it is more stable, can maintain its cell proliferation effect even after contact with cells, can exhibit an activity to induce cell proliferation even at a lower concentration, and does not induce intracellular glucose uptake. The anti-IGF-I receptor antibody according to the present invention can be used for cell culturing, by adding an appropriate amount of the antibody to culture medium or by adsorbing or immobilizing an appropriate amount of the antibody to a solid phase of a culture vessel. Thus, the anti-IGF-I receptor antibody according to the present invention makes it possible to reduce the amount to be used, and effectively induce proliferation of cells adhering to the solid phase. The vertebrate-derived cells according to the present invention should preferably be cells derived from mammals, birds, reptiles, *amphibia* or fish, more preferably cells derived from mammals or birds, still more preferably cells derived from human, monkey, rabbit, guinea pig, cow, pig, sheep, horse or dog. The cells used may be primary cultured cells, cell lines, transformants derived from such cells, or cells derived from a transgenic animal. More specifically, examples of subjects that can be cultured using the anti-IGF-I receptor antibody according to the present invention also include an organ or a tissue of a vertebrate or a transgenic animal derived from such a vertebrate. The anti-IGF-I receptor antibody according to the present invention can be used for culturing cells for the purposes of cellular production of a substance or cell therapy and regeneration medicine using such cells.

EXAMPLES

Example 1: Production of Mouse Monoclonal Antibody

A mouse monoclonal antibody can be produced by a hybridoma technique developed by Kohler, et al. (Nature 256: 495-497, 1975). An IGF-I receptor agonist antibody was produced by immunizing mice with cells expressing a human IGF-I receptor according to standard hybridoma technology. All animal experiments were conducted in accordance with the regulations of the institution. A standard method involving fusion of mouse spleen-derived cells with a mouse myeloma cell line (P3U1) was conducted. Hybridomas were selected using a medium containing hypoxanthine, aminopterin, and thymidine. The hybridoma broth was used for evaluation of the affinity by Cell ELISA using cells expressing an IGF-I receptor and evaluation of the activation of intracellular tyrosine kinase of the IGF-I receptor by PATHHUNTER to select a positive hybridoma-containing well. The hybridomas contained in this well were single-cloned by a limiting dilution technique. This single-cloned positive hybridoma was serum-free cultured, and the monoclonal antibody was purified from the broth through a protein A column (Ab-Capcher, ProteNova). An IGF-I receptor agonist antibody, named IGF11-16, was found by evaluation of human myoblast proliferation activity using the monoclonal antibody.

Example 2: Determination of Antibody Isotype

In order to determine the antibody isotype of the IGF-I receptor agonist antibody, ELISA was implemented using antibodies specific to respective antibody isotypes. An anti-mouse-IgG antibody (TAGO, 6150) diluted 2000-fold with PBS was added to a 96-well plate (Nunc, MaxiSorp) in an amount of 50 µL/well and was left to stand at 4° C. overnight. The solution in the 96-well plate was replaced with 3% BSA/PBS, and the plate was used in ELISA. The IGF-I receptor agonist antibody was added to the anti-mouse-IgG antibody-immobilized 96-well plate in an amount of 30 µL/well, followed by reaction at room temperature for 1.5 hours. Each well was washed with a washing liquid, and antibodies specifically reacting with respective isotypes of mouse IgG: anti-mouse-IgG1 antibody-ALP conjugate (SBA, 1070-04), anti-mouse-IgG2a antibody-ALP conjugate (SBA, 1080-04), anti-mouse-IgG2b antibody-ALP conjugate (SBA, 1090-04), and anti-mouse-IgG3 antibody-ALP conjugate (SBA, 1100-04), were then added in an amount of 30 µL/well, followed by reaction at room temperature for 1 hour. A substrate (PNPP) was added in an amount of 100 µL/well, followed by reaction at room temperature for 45 minutes. The difference between absorbance values at 405 and 550 nm was calculated and was evaluated as avidity.

Since IGF11-16 showed reactivity with the anti-mouse-IgG1 antibody, the isotype of the antibody was IgG1.

Example 3: Determination of Sequence of Antibody

In order to determine the gene sequences of the light chain and heavy chain of the IGF-I receptor agonist antibody, a SMARTER RACE method was implemented. Gene fragments encoding the heavy chain and the light chain of the antibody and containing initiation and termination codons were produced from RNA derived from the hybridoma producing the antibody by the SMARTER RACE method, and the nucleotide sequences thereof were determined. A first strand cDNA was synthesized using the total RNA derived from the hybridoma as a template with SMARTER RACE 5'/3' Kit (634859, Clontech) and was then amplified by PCR reaction. Using the cDNA as a template, PCR reaction was performed with the primer to universal sequence primers attached to the kit and specific to the heavy chain and the light chain of the antibody, respectively. The primers for the light chain (kappa) of the mouse antibody and the IgG1 of the mouse antibody were designed with reference to Accession Nos. BC080787 and LT160966, respectively. The designed nucleotide sequence of the primer for the light chain of the mouse antibody was ggtgaagttgatgtcttgtgagtgg (SEQ ID NO: 33), and the designed nucleotide sequence of the primer for the heavy chain of the mouse antibody was gctcttctcagtatggtggttgtgc (SEQ ID NO: 34). These primers were used in experiments. The resulting PCR products were used as 5' RACE PCR products in TA cloning.

In the TA cloning, the 5' RACE PCR products were subjected to electrophoresis, and cDNA having the target sequence was purified with QIAEX II Gel Extraction Kit (20021, Qiagen). The purified cDNA was subjected to reaction using TaKaRa-Taq (R001A, Takara) at 72° C. for 5 minutes to attach adenine to the 5' and 3' ends. The cDNA was cloned into Topoisomerase I-activated PCR II-TOPO vector (hereinafter, referred to as TOPO vector) using TOPO TA CLONING Kit (450641, Thermofisher) according to the protocol attached to the kit. The TOPO vector cloned with the target cDNA was transformed into E. coli TOP10, followed by culturing in an agar medium containing 50 μg/mL of kanamycin. The insertion of the target cDNA into the TOPO vector was verified by colony PCR. The nucleotide sequence of the cloned cDNA was identified. Similarly, the nucleotide sequence of the 3' RACE PCR product was identified to determine the full-length sequence of the antibody gene. The full-length nucleotide and amino acid sequences of the light chain of IGF11-16 are shown in SEQ ID NO:27 and SEQ ID NO:28, respectively, and the full-length nucleotide and amino acid sequences of the heavy chain of IGF11-16 are shown in SEQ ID NO:29 and SEQ ID NO:30, respectively. The amino acid sequences of CDR-H1, CDR-H2, CDR-H3, CDR-L1, CDR-L2, CDR-L3, the heavy chain variable region, and the light chain variable region of IGF11-16 are shown in SEQ ID NO:3, SEQ ID NO:4, SEQ ID NO:5, SEQ ID NO:6, SEQ ID NO:7, SEQ ID NO:8, SEQ ID NO:9, and SEQ ID NO:10, respectively.

Example 4: Avidity to IGF-I Receptor (ELISA)

In order to investigate the avidity of the IGF-I receptor agonist antibody to the IGF-I receptor of human (SEQ ID NO: 2, NP_000866), guinea pig (SEQ ID NO: 11, XP_003475316), cynomolgus monkey (SEQ ID NO: 12, NP_001248281), rabbit (SEQ ID NO: 13, XP_017193273), rat (SEQ ID NO: 14, NP_494694), and mouse (SEQ ID NO: 15, NP_034643), Cell ELISA was implemented using cells expressing the respective IGF-I receptors.

The pEF1 expression vector (Thermofisher) containing the IGF-I receptor gene of human (SEQ ID NO: 16), guinea pig (SEQ ID NO: 17), cynomolgus monkey (SEQ ID NO: 18), rabbit (SEQ ID NO: 19), rat (SEQ ID NO: 20), or mouse (SEQ ID NO: 21) was transfected into P3U1 cells by lipofection. After the lipofection, the P3U1 cells were cultured at least overnight and were added to a 96-well plate (coated with poly-D-lysine) at a concentration of $0.8 \times 10^5$ cells/well and immobilized with 10% buffered formalin (MILDFORM 10NM, Wako), followed by blocking with phosphate buffer containing 3% BSA. The resulting plate was used for ELISA.

In ELISA, 30 μL of an IGF11-16 antibody solution adjusted to 10 nM with 0.1% skimmed milk/3% BSA/PBS was added to each well and was subjected to reaction at room temperature for about 1.5 hours. After washing with a washing liquid twice, anti-mouse-IgG antibody-HRP conjugate solutions (30 μL) adjusted to predetermined concentrations with 0.1% skimmed milk/3% BSA/PBS were added to respective wells and were subjected to reaction at room temperature for about 1 hour. After washing with a washing liquid twice, 50 μL of a substrate (TMB) was added to each well to start the reaction. After about 20 minutes, 50 μL of 0.5 M sulfuric acid was added to each well. The absorbances at 450 nm and 550 nm were measured, and the difference between absorbance values at 450 nm and 550 nm was calculated. The avidity was calculated based on the difference between the absorbance values at 450 nm and 550 nm for cells (Mock cells, SEQ ID NO: 22) transfected with a vector not containing the IGF-I receptor gene as a standard value 1 (Table 1).

TABLE 1

| Type | Mouse | Rat | Guinea pig | Rabbit | Cynomolgus monkey | Human |
|---|---|---|---|---|---|---|
| Avidity | 0.9 | 1.0 | 5.3 | 5.4 | 5.4 | 5.4 |

IGF11-16 increased the avidity to the cells expressing the IGF-I receptors of human, guinea pig, cynomolgus monkey, and rabbit by more than 5-fold compared with Mock cells. In contrast, the avidity of IGF11-16 to the cells expressing the IGF-I receptors of rat and mouse was almost equivalent to that of Mock cells and was not increased. These results demonstrated that IGF11-16 binds to the human, guinea pig, cynomolgus monkey, and rabbit IGF-I receptors but does not bind to the rat and mouse IGF-I receptors.

Example 5: Avidity to Insulin Receptor (ELISA)

In order to investigate the avidity of the IGF-I receptor agonist antibody to an insulin receptor, Cell ELISA was implemented using cells expressing human insulin receptor.

The pEF1 expression vector (Thermofisher) containing the human insulin receptor gene was transfected into HEK 293T cells by lipofection. The HEK 293T cells after the lipofection were added to a 96-well plate (coated with poly-D-lysine) at a concentration of $0.8 \times 10^5$ cells/well (about 180 μL/well) and were immobilized with 10% buffered formalin (MILDFORM 10NM, Wako), followed by blocking with phosphate buffer containing 3% BSA. The plate was used in ELISA.

In ELISA, antibody solutions (30 μL) adjusted to predetermined concentrations with 0.1% skimmed milk/3% BSA/PBS were added to respective wells and were subjected to reaction at room temperature for about 1 hour. After washing with a washing liquid (tris buffer containing Tween) twice, anti-mouse-IgG antibody-ALP conjugate solutions (30 μL) adjusted to predetermined concentrations with 0.1% skimmed milk/3% BSA/PBS were added to respective wells and were subjected to reaction at room temperature for about 1 hour. After washing with a washing liquid twice, 100 μL of a substrate (PNPP) was added to each well to start the reaction. After about 30 minutes, the absorbances at 405 nm and 550 nm were measured, and the difference between absorbance values at 405 and 550 nm was calculated. The avidity was calculated based on the value of the difference between absorbance values at 405 and 550 nm for cells (Mock cells, SEQ ID NO: 22) transfected with a vector not containing the IGF-I receptor gene and the insulin receptor gene as a standard value 1 (Table 2).

TABLE 2

| IGF11-16 | human IGF-I receptor | human insulin receptor |
|---|---|---|
| 0.5 nM | 2.9 | 1.1 |
| 5 nM | 3.7 | 1.4 |

In ELISA using immobilized cells expressing the human IGF-I receptor, the difference between absorbance values at 405 and 550 nm in 0.5 nM and 5 nM of IGF11-16 was increased to about 3-fold or more compared with Mock cells. In contrast, in ELISA using immobilized cells expressing human insulin receptor, the difference between absorbance values at 405 and 550 nm in 0.5 nM and 5 nM of IGF11-16 was not increased to 1.5-fold or more. These results demonstrated that IGF11-16 more strongly binds to the IGF-I receptor compared with the insulin receptor.

Example 6: Analysis of Binding Site of IGF-I Receptor (ELISA)

In order to identify the epitope of the IGF-I receptor agonist antibody against the IGF-I receptor, the avidity of the IGF-I receptor agonist antibody to variants prepared by replacing each domain of the IGF-I receptor with a domain of the insulin receptor having a structure similar to that of the IGF-I receptor was measured.

An extracellular domain of the human IGF-I receptor (NP_000866) was replaced with an extracellular domain of insulin receptor, or an extracellular domain of human insulin receptor (NP_000199) was replaced with an extracellular domain of the IGF-I receptor. The following four substitutions were thereby produced.

Substitution 1: hIGFIR[L1-L2]/hINSR, a substitution in which L1 domain to L2 domain of human insulin receptor were replaced with L1 domain to L2 domain of the human IGF-I receptor;

Substitution 2: hINSR[L1-L2]/hIGFIR, a substitution in which L1 domain to L2 domain of the human IGF-I receptor were replaced with L1 domain to L2 domain of the human insulin receptor;

Substitution 3: hINSR[L1]/hIGFIR, a substitution in which L1 domain of the IGF-I receptor was replaced with L1 domain of the human insulin receptor; and Substitution 4: hINSR[L2]/hIGFIR, a substitution in which L2 domain of the human IGF-I receptor was replaced with L2 domain of the human insulin receptor.

The pEF1 expression vectors (Thermofisher) containing the respective genes of the above-mentioned four substitutions of the human IGF-I receptor were transfected into P3U1 cells by lipofection. The gene of hIGFIR[L1-L2]/hINSR as Substitution 1 is shown in SEQ ID NO: 23; the gene of hINSR[L1-L2]/hIGFIR as Substitution 2 is shown in SEQ ID NO: 24; the gene of hINSR[L1]/hIGFIR as Substitution 3 is shown in SEQ ID NO: 25; and the gene of hINSR[L2]/hIGFIR as Substitution 4 is shown in SEQ ID NO: 26. After the lipofection, the P3U1 cells were cultured at least overnight and were added to a 96-well plate (coated with poly-D-lysine) at a concentration of $0.8 \times 10^5$ cells/well and immobilized with 10% buffered formalin (MILDFORM 10NM, Wako), followed by blocking with phosphate buffer containing 3% BSA. The plate was used in ELISA.

In ELISA, 30 µL of an antibody solution adjusted to 10 nM with 0.1% skimmed milk/3% BSA/PBS was added to each well and was subjected to reaction at room temperature for about 1.5 hours. After washing with a washing liquid twice, 30 µL of an anti-mouse-IgG antibody-HRP conjugate solution adjusted to 5 nM with 0.1% skimmed milk/3% BSA/PBS was added to each well and was subjected to reaction at room temperature for about 1 hour. After washing with a washing liquid twice, 50 µL of a substrate (TMB) was added to each well to start the reaction. After about 20 minutes, 50 µL of 0.5 M sulfuric acid was added to each well to stop the reaction. The absorbances at 450 nm and 550 nm were measured, and the difference between absorbance values at 450 nm and 550 nm was calculated. The avidity was calculated based on the difference between absorbance values at 450 nm and 550 nm for cells (Mock cells, SEQ ID NO: 22) transfected with a vector not containing the gene of each substitution as a standard value 1 (Table 3).

TABLE 3

| Substitution | IGF11-16 |
| --- | --- |
| hIGFIR[L1-L2]/hINSR | 5.5 |
| hINSR[L1-L2]/hIGFIR | 1.5 |
| hINSR[L1]/hIGFIR | 5.7 |
| hINSR[L2]/hIGFIR | 5.6 |

In ELISA using immobilized cells expressing hIGFIR [L1-L2]/hINSR, hINSR[L1]/hIGFIR, or hINSR[L2]/hIGFIR, the absorbance at 450 to 550 nm in IGF11-16 was increased to 5-fold or more compared with Mock cells. In contrast, the avidity of IGF11-16 to the cells expressing hINSR[L1-L2]/hIGFIR was weak. These results demonstrated that IGF11-16 binds to a CR domain of the IGF-I receptor.

Example 7: Determination of Epitope of IGF11-16

In order to identify in more detail the epitope from the CR domain as an epitope of IGF11-16, the binding sequence was estimated from the species difference in avidity to the IGF-I receptor of IGF11-16. FIG. 1 shows the amino acid sequences of the CR domain of the IGF-I receptor of the respective species.

IGF11-16 binds to the human, guinea pig, and rabbit IGF-I receptors, but does not bind to the mouse and rat IGF-I receptors. Based on the results, an amino acid sequence common to human, guinea pig, and rabbit but not common to mouse and rat was estimated as the epitope of IGF11-16 from the amino acid sequences of the CR domain of the IGF-I receptor.

In order to determine the amino acid site of the CR domain of the IGF-I receptor to which IGF11-16 binds, the avidity of the CR domain to each amino acid substitution was measured by ELISA.

Cell ELISA was implemented using cells expressing an IGF-I receptor in which the amino acid sequence presumed to bind to IGF11-16 was modified in the CR domain.

As the amino acid substitutions of CR domain, the three substitutions shown below were used. In addition, a wild-type human IGF-I receptor and a wild-type rat IGF-I receptor each incorporated into a pEF1 expression vector (Thermofisher) were used as a positive control and a negative control, respectively. The expression level of each IGF-I receptor was determined using the reactivity of an FLAG M2 antibody to the FLAG tag (AspTyrLysAspAspAspAspLys; (SEQ ID NO: 35) attached to the intracellular domain of the IGF-I receptor as an index.

Substitution 1 of the CR domain: in the amino acid sequence of the human IGF-I receptor (NP_000866, SEQ ID NO: 2), aspartic acid at position 245 and alanine at position 247 were replaced with asparagine and threonine, respectively.

Substitution 2 of the CR domain: in the amino acid sequence of the human IGF-I receptor (NP_000866, SEQ ID NO: 2), glutamic acid at position 294 was replaced with aspartic acid.

Substitution 3 of the CR domain: in the amino acid sequence of the human IGF-I receptor (NP_000866, SEQ ID NO: 2), glycine at position 315 and serine at position 316 were replaced with serine and threonine, respectively.

HEK 293T cells were seeded in a 10-cm dish coated with poly-D-lysine at $9 \times 10^6$ cells/well. On the next day, each plasmid DNA was transfected into the cells by lipofection. On the following day, the HEK 293T cells were detached with 0.25% trypsin/EDTA and were suspended in a broth. The HEK 293T cells were added to a 96-well plate (coated with poly-D-lysine) at a concentration of 0.8×10⁵ cells/well and were incubated at 37° C. under conditions of 5% CO₂ overnight. The medium was removed from the 96-well plate, and the cells were immobilized with a 10% buffered formalin (MILDFORM 10NM, Wako). The 10% buffered formalin was replaced with a blocking buffer (3% BSA/PBS/sodium azide), and the plate was used in ELISA.

In ELISA, 50 μL of a solution of the IGF11-16 antibody or the FLAG M2 antibody adjusted to 1 nM with 0.1% skimmed milk/3% BSA/PBS was added to each well and was subjected to reaction at room temperature for about 1 hour. After washing with a washing liquid twice, anti-mouse-IgG antibody-HRP conjugate solutions (50 μL) adjusted to predetermined concentrations with 0.1% skimmed milk/3% BSA/PBS were added to respective wells and were subjected to reaction at room temperature for about 1 hour. After washing with a washing liquid twice, 100 μL of a substrate (TMB) was added to each well to start the reaction. After about 30 minutes, 100 μL of 0.5 M sulfuric acid was added to each well to stop the reaction, and the absorbances at 450 nm was measured. The value of the absorbance at 450 nm was evaluated as the avidity.

The results are shown FIG. 2. It was confirmed that the reactivities of the FLAG M2 antibody with the cells expressing the respective substitutions of the CR domain are substantially equivalent to one another and that the expression levels of the individual substitutions of the CR domain are substantially the same. IGF11-16 increased the value of absorbance at 450 nm to 2 or more in the wild-type human IGF-I receptor in which no modification was introduced into the CR domain and showed enhancement in the avidity. IGF11-16 increased the value of absorbance at 450 nm to 2 or more in Substitutions 1 and 2 of the CR domain and showed enhancement in the avidity. In contrast, the value of absorbance at 450 nm of Substitution 3 of the CR domain was about 1 and was the same level as the absorbance of the rat IGF-I receptor as a negative control, and no avidity was recognized. These results demonstrated that the amino acids at positions 315 and 316 of the IGF-I receptor are important for the avidity of IGF11-16 to the CR domain of the IGF-I receptor.

The results suggest that the binding site of IGF11-16 to the human IGF-I receptor is near glycine (Gly) at position 315 and serine (Ser) at position 316. In general, the recognition sequence of an antibody is composed of eight amino acid residues (average of six to ten residues) and IGF11-16 has cross-reactivity showing no avidity to the rat IGF-I receptor and showing avidity to the rabbit and human IGF-I receptors; hence, the sequence of the binding site of IGF11-16 to the human IGF-I receptor was estimated to be ProSerGlyPheIleArgAsnGly*Ser*GlnSerMet (SEQ ID NO: 32) (Gly*Ser* indicates the amino acid sequence at positions 315 and 316).

Example 8: Avidity to IGF-I Receptor Determined by Surface Plasmon Resonance The avidity (binding rate and dissociation rate) of an agent to an IGF-I receptor was measured by surface plasmon resonance (SPR).

An anti-His monoclonal antibody was immobilized to a sensor chip CM3 (GE) with an Amine Coupling Kit (BR-1000-50, GE) and a His Capture Kit (28-9950-56, GE). The immobilization conditions were NHS/EDC: 7 minutes, 50 μg/mL anti-His monoclonal antibody: 3 minutes, ethanolamine: 7 minutes, and target: ≥3000 RU. As analytes, the agent was used at predetermined concentrations. As a ligand, a recombinant human IGF-I receptor His tag (305-GR-050, R&D SYSTEMS, hereinafter, referred to as IGF-IR-His) was used. As a negative control, Purified Mouse IgG2a, K, Isotype Ctrl, Clone: MG2a-53 (401502, BioLegend, hereinafter, referred to as ctrl IgG2a) was used.

The sensor chip CM3 immobilized with the anti-His monoclonal antibody was set to Biacore T200, the reaction temperature was set to 36° C., and a running buffer (HBS-EP+, BR-1006-69, GE) was fed at a flow rate 30 μL/min. The amount of the binding ligand was set to about 100 RU, and IGF-IR-His (0.5 to 2×10⁻⁸ mol/L) was added to the sensor chip to be captured by the anti-His monoclonal antibody. Ctrl IgG2a (10 nmol/L) was allowed to react for 1 minute, and HBS-EP+ was fed at a flow rate of 30 μL/min for at least 10 minutes. The analyte and HBS-EP+ were added to flow cells (1 and 2) and flow cells (3 and 4), respectively.

The reaction conditions were set to a binding time of 600 seconds and a dissociation time of 600 seconds. After completion of the reaction, washing was performed with regeneration buffer 1 (0.2% SDS), regeneration buffer 2 (100 mmol/L Tris-HCl (pH 8.5), 1 mol/L NaCl, 15 mmol/L MgCl₂), and regeneration buffer 3 (10 mmol/L glycine-HCl (pH 1.5)) for 1 minute each at a flow rate of 30 μL/min. The dissociation rate constant (ka, 1/Ms), binding rate constant (kd, 1/s), and dissociation constant (KD, M) were calculated by analysis with a model of 1:1 binding using Biacore T200 Evaluation software (ver 2.0). The results are shown in Table 4.

TABLE 4

| Ligand | Analyte | ka (1/Ms) | kd (1/s) | KD (M) |
| --- | --- | --- | --- | --- |
| IGF-I receptor | IGF-I | 5.099 × 10⁶ | 0.009083 | 1.781 × 10⁻⁹ |
| IGF-I receptor | IGF11-16 | 1.051 × 10⁶ | <1 × 10⁻⁵* | <1 × 10⁻¹¹ |

*a value lower than the lower limit of the measurement of apparatus.

The ka value of IGF11-16 against the human IGF-I receptor was about one-fifth of that of IGF-I, indicating a low binding rate. In contrast, the kd value of IGF11-16 against the human IGF-I receptor was lower than the lower limit of the measurement of the apparatus and was lower than 1/1000 of that of IGF-I, indicating a significantly low dissociation rate and bare dissociation of IGF11-16 bound to the IGF-I receptor. The KD value of IGF11-16 against the human IGF-I receptor was lower than 1/50 of that of IGF-I, indicating a high binding strength. It is demonstrated that the avidity of IGF11-16 to an IGF-I receptor is high compared with that of IGF-I.

Example 9: Activation Effect on IGF-I Receptor or Insulin Receptor Determined by PATHHUNTER In order to detect the activation effect of an IGF-I receptor agonist antibody on the IGF-I receptor, the activation of a downstream signal of the IGF-I receptor was measured with PATHHUNTER IGF1R Functional Assay (DiscoverX).

A cell line was used in which an adapter protein SHC1-Enzyme Acceptor (EA) fusion protein including an IGF-I receptor and an SH2 domain binding to an intracellular tyrosine kinase of the IGF-I receptor was forcibly expressed intracellularly. In order to detect the activation effect of the IGF-I receptor agonist antibody on an insulin receptor, the activation of a downstream signal of the insulin receptor was measured with PATHHUNTER INSR Functional Assay (DiscoverX). Another cell line was used in which an adapter protein PLCG1-EA fusion protein including an insulin receptor and an SH2 domain that binds to an intracellular tyrosine kinase of the insulin receptor was forcibly expressed intracellularly. In each cell line, a ligand binds to the IGF-I receptor or the insulin receptor, which causes dimerization of the receptor; phosphorylation of the receptor to recruit the adapter protein having the SH2 domain; formation of a receptor signal transduction complex; acceleration of the binding between the spatially adjacent tyrosine kinase and EA; and reconstitution of the activated P-galactosidase. The effect of an agent on a receptor tyrosine kinase can be identified by measuring the level of the chemiluminescent signal of a substrate hydrolyzed by the reconstituted P-galactosidase activity.

Cells expressing the IGF-I receptor or the insulin receptor were seeded in a 96-well plate (Black/clear or White/clear) coated with poly-D-lysine or collagen-I at 90 µL/well ($2\times10^4$ cells/well or $5\times10^3$ cells/well) and were incubated at 37° C. under conditions of 5% $CO_2$. On the next day, agents in predetermined concentrations were added to the plate at 10 µL/well, followed by incubation at 37° C. under conditions of 5% $CO_2$. On the following day, 30 µL of the culture supernatant was added to 15 µL of a substrate solution, followed by reaction for 60 minutes, and the luminescent signal was measured with a luminometer (Tristar, Berthold Japan K.K.). The activation of the IGF-I receptor was calculated with the activity of a group in which only a solvent was defined as 100%. The results are shown in Table 5.

TABLE 5

| Agent | Concentration (nM) | | |
|---|---|---|---|
| | 0.5 | 5 | 50 |
| Control antibody (FLAG M2) | 105 | 109 | 109 |
| Insulin | 184 | 1244 | 4619 |
| IGF-I | 208 | 3537 | 5248 |
| IGF11-16 | 234 | 2900 | 2786 |

The activation of the insulin receptor was calculated with the activity of a group in which only a solvent was defined as 100%. The results are shown in Table 6.

TABLE 6

| Agent | Concentration (nM) | | |
|---|---|---|---|
| | 0.5 | 5 | 50 |
| Control antibody (FLAG M2) | 105 | 104 | 111 |
| Insulin | 1432 | 1655 | 1405 |
| IGF-I | 126 | 158 | 240 |
| IGF11-16 | 95 | 96 | 93 |

The activation of the IGF-I receptor by an agent was measured using a cell line expressing the IGF-I receptor. In the cell line expressing the IGF-I receptor, IGF-I and IGF11-16 showed the activation effect on the IGF-I receptor compared with a control.

The activation of the insulin receptor by an agent was measured using a cell line expressing the insulin receptor. In the cell line expressing the insulin receptor, the activation effect on the insulin receptor by insulin was observed. IGF-I concentration-dependently activated the insulin receptor, and a significant activation effect was observed at 50 nM. In contrast, IGF11-16 did not activate the insulin receptor.

It is known that IGF-I shows reactivity with an insulin receptor. It is also known that the activation of an insulin receptor causes a hypoglycemic effect. It was demonstrated that IGF11-16 specifically acts on the IGF-I receptor and does not have the hypoglycemic effect via the insulin receptor.

Example 10: Cell Proliferation Activity on Human Myoblast

In order to investigate the proliferation activity of the IGF-I receptor agonist antibody on human myoblasts, an agent was added to human myoblasts, and the amount of ATP in the cells after 4 days was measured.

Normal human skeletal muscle myoblasts (HSMM, Lonza) were seeded in a 96-well plate (coated with collagen type I) at 0.1 mL/well ($2\times10^3$ cells/well) using an SkBM-2 (Lonza, CC-3246) medium containing 1% BSA and were incubated at 37° C. under conditions of 5% $CO_2$. On the next day of the cell seeding, each agent was added to the plate at 25 µL/well and was incubated at 37° C. under conditions of 5% $CO_2$ for 4 days. The amount of intracellular ATP was measured as an index of cell proliferation with CELLTITER-GLOLuminescent Cell Viability Assay (Promega). The supernatant was removed from the 96-well plate subjected to the incubation for 4 days so that the broth in each well was 50 µL, and the plate was then left to stand at room temperature for at least 30 minutes. CELLTITER-GLO reagent was added to the plate at 50 µL/well, followed by reaction for at least 10 minutes. The luminescent signal was then measured with a luminometer (Tristar, Berthold Japan K.K.). The activity was calculated with the activity of a group containing only a solvent defined as 100%. The results are shown in Table 7.

TABLE 7

| Agent | Concentration (nM) | Experiment 1 Cell proliferation inducing activity (%) | Experiment 2 Cell proliferation inducing activity (%) |
|---|---|---|---|
| Control antibody (FLAG M2 Ab) | 0.005 | 99 | — |
| IGF-I | 0.005 | 102 | 103 |
| IGF11-16 | 0.005 | 141 | 130 |
| 16-13 | 0.005 | — | 102 |
| 26-3 | 0.005 | — | 108 |
| Solvent control 1* (containing $NaN_3$) | — | — | 104 |
| Control antibody (FLAG M2 Ab) | 0.5 | 98 | — |
| IGF-I | 0.5 | 133 | 137 |
| IGF11-16 | 0.5 | 146 | 143 |
| 16-13 | 0.5 | — | 109 |
| 26-3 | 0.5 | — | 119 |
| Solvent control 2* (containing $NaN_3$) | — | — | 112 |

*Solvent controls 1 and 2 contain sodium azide in an amount of 0.005 nM and 0.5 nM, respectively, which are the same amounts as those in antibodies 16-13 and 26-3.

IGF-I and IGF11-16 enhanced the cell proliferation activity, compared with the control antibody (FLAG M2, Sigma-Aldrich).

The proliferation activity of human myoblasts was concentration-dependently enhanced in 0.00005, 0.0005, 0.005, 0.05, 0.5, 5, 50, and 500 nM IGF11-16. The $EC_{50}$ values of the myoblast proliferative activity of IGF11-16 and IGF-I were 0.004 nM and 0.61 nM, respectively. The results indicate that the activity of IGF11-16 was above 100 times that of IGF-I.

The antibodies 16-13 and 26-3 described in Non-Patent Literature 35 did not show noticeable cell proliferation activity compared with the solvent control (containing sodium azide), and the activity was weak compared with that of IGF11-16.

Example 11: Cell Proliferation Activity in Guinea Pig Myoblast

Guinea pig myoblasts (Cell Applications) were seeded in a 96-well plate (coated with collagen type I) at 0.1 mL/well ($4\times10^3$ cells/well) using an SkBM-2 (Lonza, CC-3246) medium containing 1% BSA and were incubated at 37° C. under conditions of 5% $CO_2$. On the next day of the cell seeding, each agent was added to the plate at 25 µL/well and was incubated at 37° C. under conditions of 5% $CO_2$ for 4 days. The amount of intracellular ATP was measured as an index of cell proliferation by CELLTITER-GLO Luminescent Cell Viability Assay (Promega). The supernatant was removed from the 96-well plate subjected to the incubation for 4 days so that the broth in each well was 50 µL, and the plate was then left to stand at room temperature for at least 30 minutes. CELLTITER-GLO reagent was added to the plate at 50 µL/well, followed by reaction for at least 10 minutes. The luminescent signal was then measured with a luminometer (Tristar, Berthold Japan K.K.).

The proliferation activity of guinea pig myoblasts was concentration-dependently enhanced in 0.00005, 0.0005, 0.005, 0.05, 0.5, 5, 50, and 500 nM IGF11-16. The $EC_{50}$ values of the myoblast proliferative activity of IGF11-16 and IGF-I were 0.004 nM and 0.76 nM, respectively. The results indicate that the activity of IGF11-16 was above 100 times that of IGF-I.

Example 12: In Vitro Comparison with Persistence of Effect of IGF-I

In order to compare the persistence of the effects of IGF11-16 and IGF-I, the medium was replaced after 18 hours from the addition of IGF11-16 or IGF-I, and the proliferation activity of human myoblasts was measured under the conditions that IGF11-16 and IGF-I were removed.

Normal human skeletal muscle myoblasts (Human Skeletal Muscle Myoblast Cells, HSMM, Lonza) were seeded in a 96-well plate (coated with collagen type I) at 0.1 mL/well ($2\times10^3$ cells/well) using an SkBM-2 (Lonza, CC-3246) medium containing 1% BSA and were incubated at 37° C. under conditions of 5% $CO_2$. On the next day of the cell seeding, IGF11-16 or IGF-I was added to the plate at 25 µL/well. After 18 hours from the addition, the medium was replaced with a medium not containing IGF11-16 or IGF-I or a medium containing them, followed by incubation at 37° C. under conditions of 5% $CO_2$ for 4 days. The amount of intracellular ATP was measured as an index of cell proliferation by CELLTITER-GLO Luminescent Cell Viability Assay (Promega). The supernatant was removed from the 96-well plate subjected to the incubation for 4 days so that the broth in each well was 50 µL, and the plate was then left to stand at room temperature for at least 30 minutes. CELLTITER-GLO reagent was added to the plate at 50 µL/well, followed by reaction for at least 10 minutes. The luminescent signal was then measured with a luminometer (Tristar, Berthold Japan K.K.). The proportion (control group: 0%) relative to a control group containing only a solvent was calculated as the cell proliferation activity. The results are shown in FIG. 3.

The cell proliferation activity increased to 39% and 75%, respectively, in the groups in which 1 nM and 5 nM IGF-I were respectively added for 4 days. The cell proliferation activity increased to 8% and 10%, respectively, in the groups in which 1 nM and 5 nM IGF-I were respectively added for 18 hours and were then washed out, and the activity was lower than ⅕ of those of the groups in which IGF-I was added for 4 days, indicating a noticeable reduction in the effect.

In the group in which 0.5 nM IGF11-16 was added for 4 days, the cell proliferation activity increased to 49%. The cell proliferation activity of the group in which 0.5 nM IGF11-16 was added for 18 hours and was then washed out increased to 30%, which corresponded to 60% or more of the activity of the group in which IGF11-16 was added for 4 days.

The cell proliferation activities of the group treated with 0.5 nM IGF11-16 in which washing out was performed after addition of an agent were compared with the cell proliferation activities of the groups treated with 1 nM and 5 nM IGF-I. The activity of IGF11-16 was high in statistical significance. These results demonstrated that IGF11-16 maintains the proliferation activity of human myoblasts even after washing out of the agent and has a strong effect compared with IGF-I. IGF11-16 maintained the cell proliferation activity even after washing out. The results indicate that unlike the effect of IGF-I, IGF11-16 strongly binds to the IGF-I receptor and has a persistent activation effect on the IGF-I receptor.

Example 13: Glucose Uptake in Human Differentiated Muscle Cell

In order to investigate the effect of IGF11-16 on the glucose uptake, the uptake amount of radiolabeled $^3$H-2-deoxy glucose was measured using human differentiated muscle cells and was compared with the effect of IGF-I.

Normal human skeletal muscle myoblasts (Human Skeletal Muscle Myoblast Cells, HSMM, Lonza) were seeded in a 24-well plate (Costar, 3526) at 0.5 mL/well ($2\times10^4$ cells/well) and were incubated at 37° C. under conditions of 5% $CO_2$. The medium (an SkBM-2 (Lonza, CC-3246) supplemented with FBS (Lonza, CC-4423W), L-Glutamine (Lonza, CC-4422W), Dexamethasone (Lonza, CC-4421W), rhEGF (Lonza, CC-4420W), and GA-1000 (Lonza, CC-4419W)) was replaced with fresh one until the cells were confluent. The medium was replaced with 0.5 mL/well of a medium for differentiation (DMEM/F12 (1:1) (Gibco, 11320) containing 2% horse serum (Sigma, H1270), 50 U/mL penicillin, 50 µg/mL streptomycin (Gibco, 15070-063)), and the confluent HSMM cells were incubated at 37° C. under conditions of 5% $CO_2$ to start differentiation into muscle cells. The cells after about 6 days from the start of differentiation were used as human differentiated muscle cells in a glucose uptake experiment.

Figure 4:
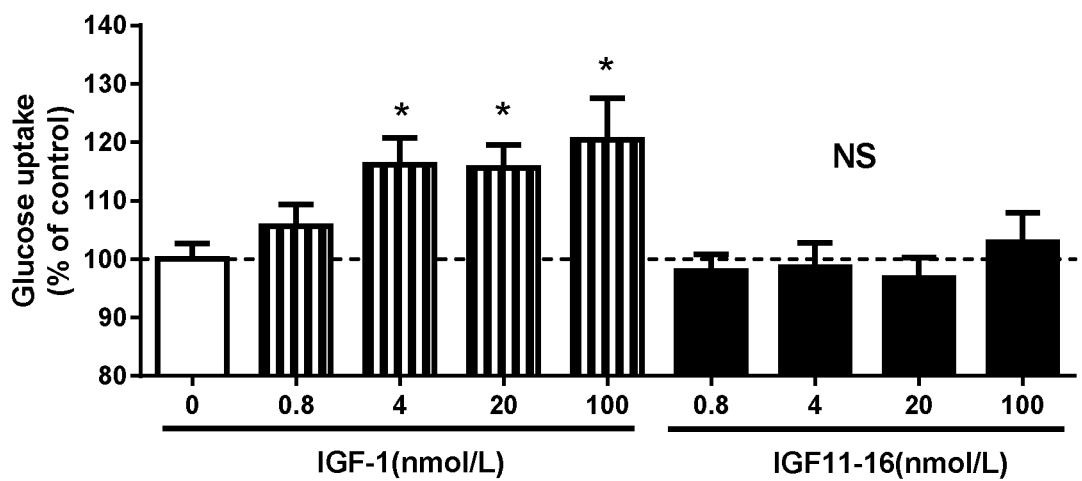
FIG. 4 is a graph indicating the glucose uptake effect by human differentiated muscle cells after addition of IGF-I and IGF11-16.

The medium was replaced with 0.5 mL/well of a starvation medium (1 g/L glucose-containing DMEM (Gibco, 11885) supplemented with 0.1% BSA Fatty Acid free (Seikagaku Corporation, 82-002-5), 50 U/mL penicillin, and 50 µg/mL streptomycin (Gibco, 15070-063)), and the human differentiated muscle cells were incubated at 37° C. under conditions of 5% $CO_2$ overnight. On the next day, the medium was replaced with 0.5 mL/well of a medium for starvation, and the cells were incubated at 37° C. under conditions of 5% $CO_2$ for 2 hours. The wells were washed with 1 mL/well of PBS, and 0.5 mL/well of a treatment medium containing the respective agents was added to the wells, followed by incubation at 37° C. under conditions of 5% $CO_2$ for 2 hours. The treatment medium was prepared to give final concentrations of 0.1 mmol/L glucose, 0.1% BSA, 3H-2-deoxy glucose (1 Ci/mL), and each concentration of a human recombinant IGF-I or IGF-I receptor agonist antibody using a glucose uptake buffer (containing 20 mmol/L HEPES (DOJINDO, 342-01375), 150 mmol/L NaCl (SIGMA, S5150), 5 mmol/L KCl (Wako, 163-03545), 5 mmol/L $MgSO_4$ (Wako, 131-00405), 1.2 mmol/L $KH_2PO_4$ (Wako, 169-04245), 25 mmol/L $CaCl_2$) (Fluka, 21114), and 2 mmol/L pyruvate (Wako, 190-14881) dissolved in water for injection and having a pH 7.4 adjusted with NaOH). The wells were washed by adding 1 mL/well of cooled PBS three time to stop the glucose uptake. The cells were lysed by adding 0.25 mL/well of 1 N NaOH. The whole amount of the cell lysate was added to a vial containing 3 mL of liquid scintillator ULTIMA GOLD (PerkinElmer Japan) and was stirred. The radioactivity (DPM) of $^3H$ was measured for 3 minutes with a liquid scintillation counter. The glucose uptake ratio of a treated group was calculated with the averaged glucose uptake amount (DPM) of an untreated group (control group) defined as 100%. The results are shown in FIG. 4.

In 0.8, 4, 20, and 100 nM IGF-I, the glucose uptake was concentration-dependently and significantly enhanced. In contrast, IGF11-16 did not show significant effect until 100 nM. These results suggest that the glucose uptake effect of IGF11-16 in human differentiated muscle cells is extremely weak.

Example 14: In Vivo Efficacy (Effect of Increasing Muscle Mass in Guinea Pig)

In order verify the in vivo efficacy of the IGF-I receptor agonist antibody, IGF11-16 was administered to guinea pigs in a single administration, and the muscle mass after 2 weeks was measured for comparison with the effect when IGF-I was continuously administered. The effect of increasing muscle mass is defined as an effect of increasing the weight of muscle of a guinea pig by 5% or more compared with that of the control group.

Figure 5:
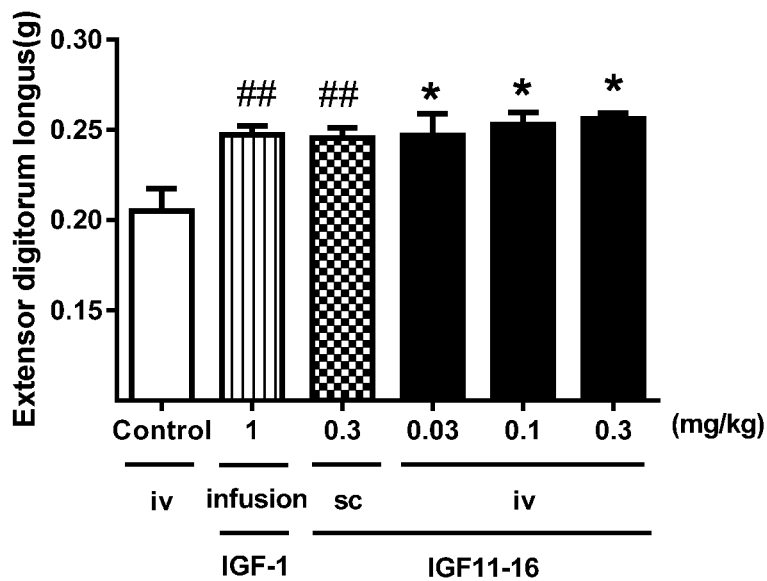
FIG. 5 is a graph indicating the weights of extensor digitorum longus muscles of guinea pigs which received sustained administration of IGF-I using an osmotic pump for two weeks or single-dose subcutaneous or intravenous administration of IGF11-16 two weeks ago.

IGF11-16 (0.03, 0.1, or 0.3 mg/kg) was subcutaneously or intravenously administered to normal guinea pigs in a single administration. Human recombinant IGF-I (Mecasermin) as a positive control was subcutaneously embedded with an osmotic pump (Alzet) and was continuously administered at 1 mg/kg/day. After two weeks from the administration of the agent, the guinea pigs were euthanized by exsanguination under anesthesia, and the weight of the extensor digitorum longus muscle was measured. The results are shown in FIG. 5.

In the group (iv) of intravenous administration of IGF11-16 in an amount of 0.03, 0.1, or 0.3 mg/kg, the muscle mass was dose-dependently and significantly increased, compared with the control group treated with only a solvent. Even in the group (sc) of subcutaneous administration of IGF11-16 at 0.3 mg/kg, the muscle mass was significantly increased compared with the control group.

The increased amounts of the muscle in the groups of administration of 0.03 to 0.3 mg/kg of IGF11-16 in a single administration were equivalent to that in the group (infusion) of continuous administration of 1 mg/kg/day of human recombinant IGF-I. The results indicate that IGF11-16 shows efficacy even in in vivo by intravenous or subcutaneous administration in a single administration.

It was demonstrated that IGF11-16 shows efficacy equivalent to that by continuous administration of IGF-I in a single administration. In clinical use, IGF-I (Mecasermin) is administered once or twice a day. In contrast, IGF11-16 administered one every other week shows in vivo effectiveness equivalent to that in continuous administration of IGF-I, indicating that IGF11-16 has excellent persistence compared with IGF-I.

Example 15: In Vivo Hypoglycemic Effect (Hypoglycemic Effect in Guinea Pig)

In order to verify whether the IGF-I receptor agonist antibody has in vivo hypoglycemic effect or not, IGF11-16 was administered to guinea pigs in a single administration, and the blood glucose levels were measured over time and compared with the hypoglycemic effect of IGF-I in a single administration. The hypoglycemic effect is defined as an effect of lowering the blood glucose level to 50 mg/dL or less or causing hypoglycemia.

Figure 6:
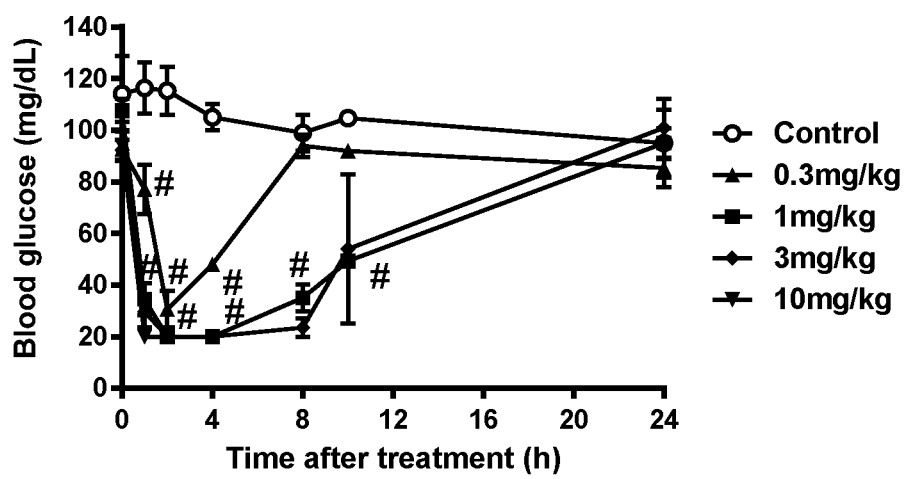
FIG. 6 is a graph indicating the time course of the blood glucose level of guinea pigs under fasting conditions after single-dose subcutaneous administration of IGF-I.

IGF-I was subcutaneously administered to guinea pigs a single time, and the hypoglycemic effect was investigated. The guinea pigs were fasted for 12 hours, and human recombinant IGF-I (Mecasermin) was subcutaneously administered to the guinea pigs at 0.3, 1, 3, and 10 mg/kg a single time. The guinea pigs were fasted for 24 hours after the administration. Blood was collected from the awake guinea pigs at before the administration (0 hour) and at 1, 2, 4, 8, 10, and 24 hours after the administration and was subjected to measurement of the blood glucose level with a Glutest Sensor (Sanwa Kagaku Kenkyusyo). The results are shown in FIG. 6.

IGF-I showed a significant glucose lowering effect at 0.3 mg/kg or more. Hypoglycemia was observed at 1 mg/kg or more. Death was caused at 3 mg/kg or more.

Figure 7:
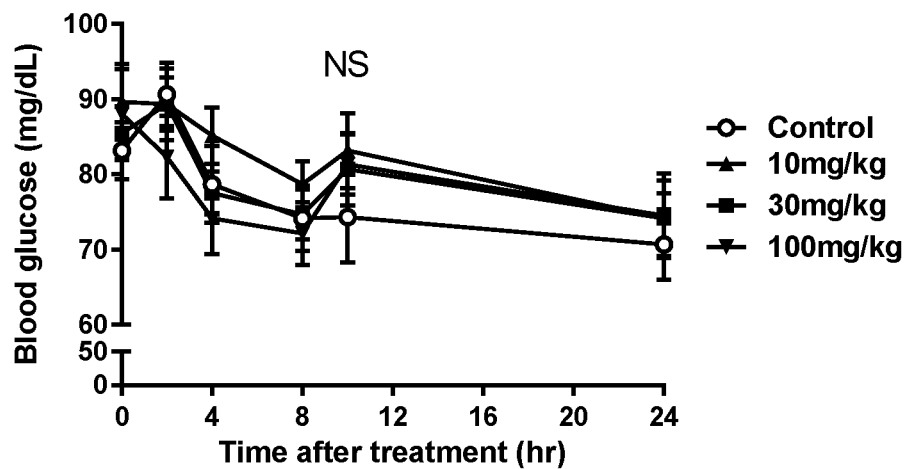
FIG. 7 is a graph indicating the time course of the blood glucose level of guinea pigs under fasting conditions after single-dose subcutaneous administration of IGF11-16.

IGF11-16 was subcutaneously administered to guinea pigs a single time, and the hypoglycemic effect was investigated. The guinea pigs were fasted for 12 hours, and IGF11-16 was subcutaneously administered to the guinea pigs at 10, 30, and 100 mg/kg a single time. The guinea pigs were fasted for 24 hours after the administration. Blood was collected from the awake guinea pigs at before the administration (0 hour) and at 2, 4, 8, 10, and 24 hours after the administration and was subjected to measurement of the blood glucose level with a Glutest Sensor (Sanwa Kagaku Kenkyusyo). The results are shown in FIG. 7.

IGF11-16 did not show any significant difference in the blood glucose level, even in the group of 100 mg/kg administration, compared with a control group in which only the solvent was administered. The results indicate that subcutaneous administration of IGF11-16 does not have a hypoglycemic effect and does not affect the blood glucose level.

Figure 8:
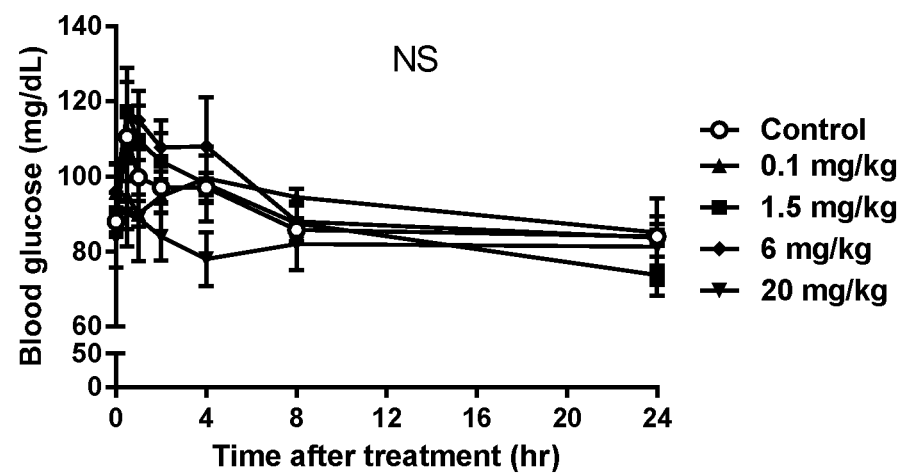
FIG. 8 is a graph indicating the time course of the blood glucose level of guinea pigs under fasting conditions after single-dose intravenous administration of IGF11-16.

IGF11-16 was intravenously administered to guinea pigs a single time, and the hypoglycemic effect was investigated. The guinea pigs were fasted for 12 hours, and IGF11-16 was intravenously administered to the guinea pigs at 0.1, 1.5, 6, and 20 mg/kg. The guinea pigs were fasted for 24 hours after the administration. Blood was collected from the awake guinea pigs at before the administration (0 hour) and at 0.5, 1, 2, 4, 8, and 24 hours after the administration and was subjected to measurement of the blood glucose level with a Glutest Sensor (Sanwa Kagaku Kenkyusyo). The results are shown in FIG. 8.

IGF11-16 did not show any significant difference in the blood glucose level, even in the group of 20 mg/kg administration, compared with a control group in which only the solvent was administered. The results indicate that intravenous administration of IGF11-16 also does not have a hypoglycemic effect and does not affect the blood glucose level.

IGF11-16 does not have a noticeable hypoglycemic effect in both subcutaneous and intravenous administrations, unlike IGF-I, and does not affect the blood glucose level, indicating that IGF11-16 has a possibility as an agent that overcomes a side effect of IGF-I, hypoglycemia.

Example 16: In Vivo Efficacy (Growth Promoting Effect in Guinea Pig)

Figure 9:
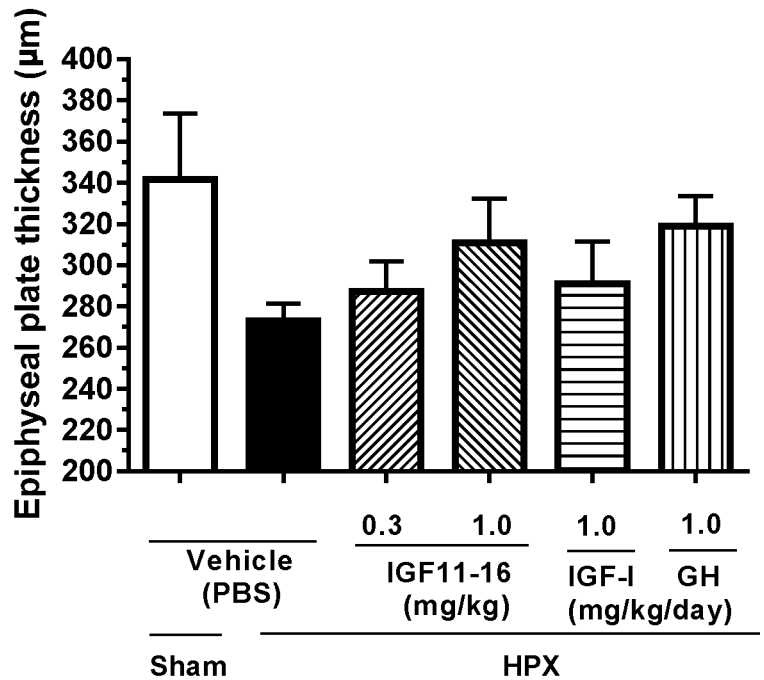
FIG. 9 is a graph indicating the effects of IGF11-16 in increasing the thickness of growth plate cartilage of hypophysectomized guinea pigs (HPX)
Figure 10:
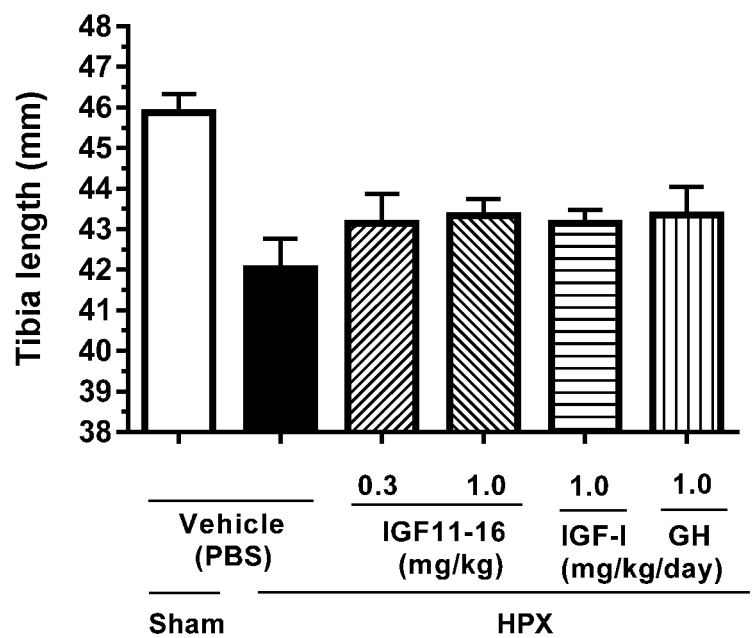
FIG. 10 is a graph indicating the effects of IGF11-16 in increasing the length of tibia in hypophysectomized guinea pigs (HPX)

In order to verify the in vivo efficacy of the IGF-I receptor agonist antibody on bone, the effect was compared with IGF-I continuously administered and growth hormone (GH) repeatedly administered once a day. IGF11-16 was administered to guinea pigs with removed pituitary gland a single time. After two weeks, the length of the tibia and the thickness of the growth plate cartilage were measured as indices of the growth promoting effect. IGF11-16 (0.3 mg/kg and 1 mg/kg) was subcutaneously administered to the guinea pigs with removed pituitary gland a single time. As a control, human recombinant IGF-I (Mecasermin) was subcutaneously embedded with an osmotic pump (Alzet) and was continuously administered at 1 mg/kg/day. Another control, human recombinant GH (GENOTROPIN), was subcutaneously administered at a dose of 1 mg/kg repeatedly once a day. After two weeks from the agent administration, the guinea pigs were euthanized by exsanguination under anesthesia, and the thickness of the growth plate cartilage of the tibia proximal and the length of the tibia were measured. The results are shown in FIGS. 9 and 10.

In the group (IGF11-16) in which IGF11-16 was subcutaneously administered at 0.3 mg/kg and 1 mg/kg, the thickness of the growth plate cartilage and the length of the tibia were dose-dependently and significantly extended to show a growth promoting effect, compared with those in a control group (vehicle) in which the guinea pigs with removed pituitary gland were treated with only the solvent.

The growth promoting effect of the group of a single administration of IGF11-16 at 0.3 mg/kg was equivalent to that of the group (IGF-I) of continuous administration of human recombinant IGF-I at 1 mg/kg/day. The growth promoting effect of the group of single administration of IGF11-16 at 1 mg/kg was equivalent to that of the group (GH) of repeated administration of human recombinant GH at 1 mg/kg/day. The results indicate that a single administration of IGF11-16 shows efficacy equivalent to that of a continuous administration of IGF-I and that of repeated administration of GH once a day. In clinical use, human recombinant IGF-I (Mecasermin) and human recombinant GH (GENOTROPIN) are administered by subcutaneous injection once or twice a day and six or seven times a week, respectively. In contrast, IGF11-16 administered once every other week shows in vivo effectiveness equivalent to that in continuous administration of IGF-I and that in repeated administration of GH once a day, indicating that IGF11-16 has excellent persistence compared with IGF-I and GH.

Example 17: Kinetics of IGF-I and IGF11-16 in Blood

Kinetics of IGF-I in Blood

Figure 11:
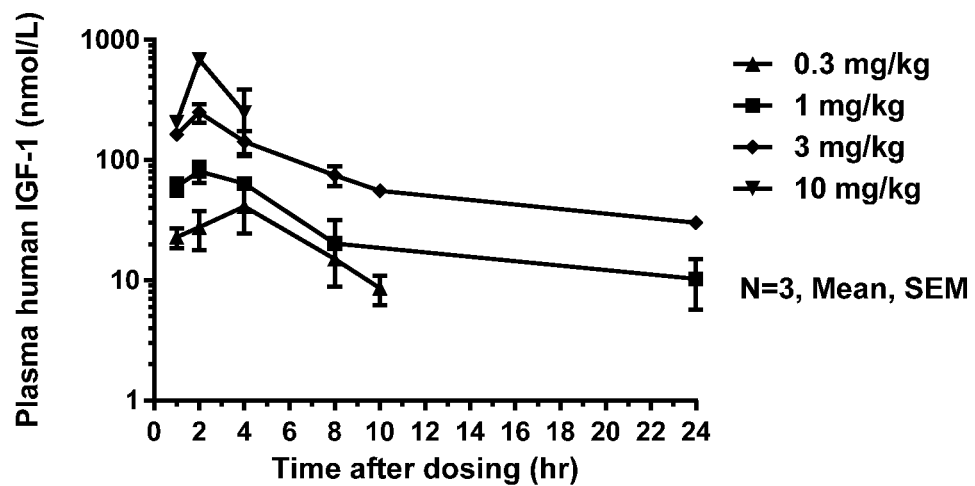
FIG. 11 is a graph indicating the blood kinetics of IGF-I in guinea pigs under fasting conditions after single-dose subcutaneous administration.

Guinea pigs were fasted for 12 hours, and human recombinant IGF-I was subcutaneously administered to the guinea pigs at 0.3, 1, 3, and 10 mg/kg. The guinea pigs were fasted for 24 hours after the administration. Blood was collected from the awake guinea pigs at before the administration (0 hour) and at 1, 2, 4, 8, 10, and 24 hours after the administration. The human IGF-I concentration in plasma was measured by ELISA (DG100, R&D). The results are shown in FIG. 11.

The plasma IGF-I concentration increased administration-dose dependently and, after 24 hours from the administration, decreased to about 50% of the maximum plasma IGF-I concentration. In the group of 0.3 mg/kg administration, the IGF-I concentration at 24 hours after the administration was lower than the lower limit of the measurement. In the group of 10 mg/kg administration, the guinea pigs died due to hypoglycemia after 4 hours from the administration, and the plasma could not be collected.

Kinetics of IGF11-16 in Blood

Figure 12:
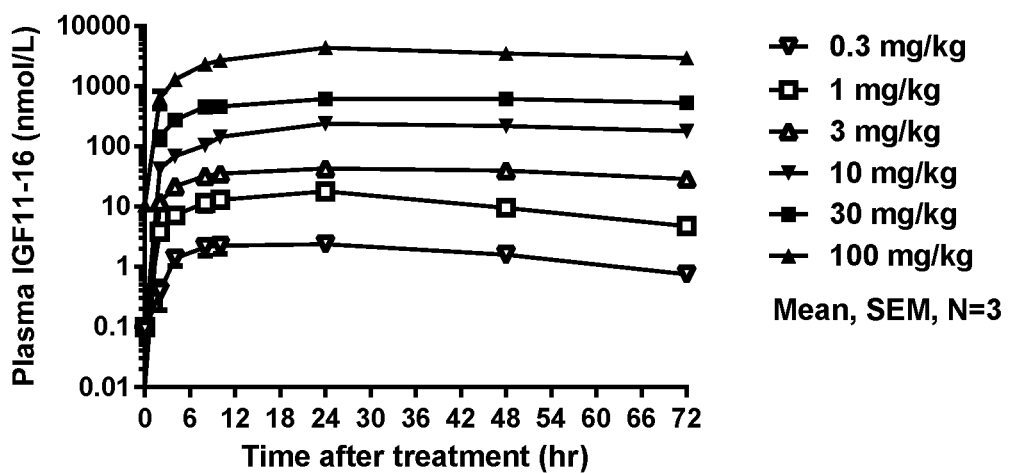
FIG. 12 is a graph indicating the blood kinetics of IGF11-16 in guinea pigs under fasting conditions after single-dose subcutaneous administration.

Guinea pigs were fasted for 12 hours, and the IGF-I receptor agonist antibody was subcutaneously administered to the guinea pigs at 0.3, 1, 3, 10, 30, and 100 mg/kg. The guinea pigs were fasted for 24 hours after the administration and were then refed. Blood was collected from the awake guinea pigs at before the administration (0 hour) and at 2, 4, 8, 10, 24, 48, and 72 hours after the administration. The IGF11-16 concentration in plasma was measured by ELISA. The results are shown in FIG. 12.

The plasma IGF11-16 concentration increased administration-dose dependently, and the plasma IGF11-16 concentration after 48 hours from the administration was retained to be at about 50% or more of that at 24 hours after the administration, indicating that the kinetics of IGF11-16 in blood is excellent in the persistence compared with that of IGF-I.

INDUSTRIAL APPLICABILITY

The present invention can provide an antibody which specifically binds to an IGF-I receptor of a vertebrate, and thereby increase the muscle mass or the thickness of growth plate cartilage via the IGF-I receptor, but does not reduce the blood glucose level. Therefore, the present invention can be used for the treatment, prevention, or diagnosis of diseases associated with an anti-IGF-I receptor antibody.

The invention claimed is:

1. An anti-IGF-I (Insulin-like Growth Factor I) receptor antibody or antigen-binding fragment thereof that exhibits an activity to induce growth of vertebrate-derived cells,
   wherein said antibody or antigen-binding fragment thereof comprises a heavy chain variable region comprising three complementarity-determining regions (CDRs H1-H3), and further comprises a light chain variable region comprising three complementarity-determining regions (CDRs L1-L3),
   wherein the CDR-H1 comprises the amino acid sequence of SEQ ID NO: 3, or comprises the amino acid sequence of SEQ ID NO: 3 in which one amino acid is substituted, deleted, or inserted;
   wherein the CDR-H2 comprises the amino acid sequence of SEQ ID NO: 4, or comprises the amino acid sequence of SEQ ID NO: 4 in which up to two amino acids are substituted, deleted, or inserted;
   wherein the CDR-H3 comprises the amino acid sequence of SEQ ID NO: 5, or comprises the amino acid sequence of SEQ ID NO: 5 in which up to two amino acids are substituted, deleted, or inserted;
   wherein the CDR-L1 comprises the amino acid sequence of SEQ ID NO: 6, or comprises the amino acid sequence of SEQ ID NO: 6 in which up to two amino acids are substituted, deleted, or inserted;
   wherein the CDR-L2 comprises the amino acid sequence of SEQ ID NO: 7, or comprises the amino acid sequence of SEQ ID NO: 7 in which one amino acid is substituted, deleted, or inserted;
   wherein the CDR-L3 comprises the amino acid sequence of SEQ ID NO: 8, or comprises the amino acid sequence of SEQ ID NO: 8 in which up to two amino acids are substituted, deleted, or inserted.

2. The anti-IGF-I receptor antibody or antigen-binding fragment thereof according to claim 1, wherein the activity of said antibody or antigen-binding fragment thereof to induce growth of vertebrate-derived cells is equal to or higher than the corresponding activity of a wild-type IGF-I.

3. The anti-IGF-I receptor antibody or antigen-binding fragment thereof according to claim 1, wherein when said antibody or antigen-binding fragment thereof is contacted with cultured vertebrate-derived cells, the duration of activity of said antibody or antigen-binding fragment thereof to induce growth of the cultured cells relative to the duration of contact is improved as compared to a wild-type IGF-I.

4. The anti-IGF-I receptor antibody or antigen-binding fragment thereof according to claim 1, wherein said antibody or antigen-binding fragment thereof binds to wild-type IGF-I receptor comprising the amino acid sequence of SEQ ID NO: 2.

5. The anti-IGF-I receptor antibody or antigen-binding fragment thereof according to claim 1, which exhibits an activity to induce an increase in the muscle mass and/or the body length of a vertebrate when parenterally administered to the vertebrate.

6. The anti-IGF-I receptor antibody or antigen-binding fragment thereof according to claim 1, which is administered to a vertebrate at a frequency of once a week or less.

7. The anti-IGF-I receptor antibody or antigen-binding fragment thereof according to claim 1, wherein the vertebrate is a human; a guinea pig, a mouse, a rat, a monkey, a rabbit, a cow, a pig, a horse, a sheep, a dog, or a chicken; or a non-human vertebrate engineered to express a human IGF-I receptor.

8. The anti-IGF-I receptor antibody or antigen-binding fragment thereof according to claim 1, which does not induce glucose uptake by differentiated muscle cells when administered at a dosage sufficient to induce growth of vertebrate-derived cells.

9. The anti-IGF-I receptor antibody or antigen-binding fragment thereof according to claim 8, which does not induce glucose uptake by differentiated muscle cells when administered at a dosage of 100 times or more of the $EC_{50}$ value for inducing growth of vertebrate-derived cells in vitro.

10. The anti-IGF-I receptor antibody or antigen-binding fragment thereof according to claim 1, wherein the vertebrate-derived cells are myoblasts derived from a human or a non-human mammal.

11. The anti-IGF-I receptor antibody or antigen-binding fragment thereof according to claim 5, which does not lower the blood glucose level of a vertebrate when parenterally administered to the vertebrate at a dosage sufficient to induce an increase in the muscle mass and/or the body length of the vertebrate.

12. The anti-IGF-I receptor antibody or antigen-binding fragment thereof according to claim which does not change the blood glucose level of a vertebrate when parenterally administered to the vertebrate at a dosage of 10 times or more of an effective dosage sufficient to induce an increase in the muscle mass and/or the body length of the vertebrate.

13. The anti-IGF-I receptor antibody or antigen-binding fragment thereof according to claim 1, which binds to a CR domain of an IGF-I receptor.

14. The anti-IGF-I receptor antibody or antigen-binding fragment thereof according to claim 13, which binds to an epitope containing ProSerGlyPheIleArgAsnX$_1$X$_2$GlnSerMet (SEQ ID NO: 31) (where X$_1$ represents Gly or Ser and X$_2$ represents Ser or Thr), or a part in the vicinity thereof, in the sequence of the CR domain of the IGF-I receptor.

15. The anti-IGF-I receptor antibody or antigen-binding fragment thereof according to claim 14, which binds to an epitope containing ProSerGlyPheIleArgAsnGlySerGlnSerMet (SEQ ID NO: 32), or a part in the vicinity thereof, in the sequence of the CR domain of the IGF-I receptor.

16. The anti-IGF-I receptor antibody or antigen-binding fragment thereof according to claim 1, which has a cross-reactivity with an IGF-I receptor of a human or a non-human vertebrate selected from the group consisting of a guinea pig, a mouse, a rat, a monkey, a rabbit, a cow, a pig, a horse, a sheep, a dog, and a chicken.

17. The anti-IGF-I receptor antibody or antigen-binding fragment thereof according to claim 14, which has at least one of the features of:
  1) exhibiting an activity to induce an increase in the muscle mass and/or the body length of a vertebrate when parenterally administered to the vertebrate;
  2) not inducing glucose uptake by differentiated muscle cells when administered at a dosage sufficient to induce growth of vertebrate-derived cells; and
  3) not changing the blood glucose level of a vertebrate when parenterally administered to the vertebrate at a dosage sufficient to induce an increase in the muscle mass and/or the body length of the vertebrate.

18. The anti-IGF-I receptor antibody or antigen-binding fragment thereof according to claim 1, which has at least one of the features of:
  1) inhibiting growth of vertebrate-derived cells induced by IGF-I;
  2) inhibiting IGF-I-induced cell proliferation in a vertebrate suffering a cell proliferative disease when parenterally administered to the vertebrate;
  3) not affecting glucose uptake by differentiated muscle cells at a dosage sufficient to inhibit growth of vertebrate-derived cells induced by IGF-I; and
  4) not changing the blood glucose level of a vertebrate suffering a cell proliferative disease when parenterally administered to the vertebrate at a dosage sufficient to inhibit IGF-I-induced cell proliferation in the vertebrate.

19. The anti-IGF-I receptor antibody or antigen-binding fragment thereof according to claim 1, which is an immunoglobulin, Fab, scFv, diabody or bispecific antibody, or a derivative thereof.

20. The anti-IGF-I receptor antibody or antigen-binding fragment thereof according to claim 1, wherein said antibody or antigen-binding fragment thereof comprises a light chain variable region comprising, as complementarity-determining regions (CDRs) 1-3, the amino acid sequences of SEQ ID NOs: 6 to 8 respectively, and
  wherein said antibody or antigen-binding fragment thereof further comprises a heavy chain variable region comprising, as CDRs 1-3, the amino acid sequences of SEQ ID NOs: 3 to 5 respectively.

21. The anti-IGF-I receptor antibody or antigen-binding fragment thereof according to claim 20, wherein said antibody or antigen-binding fragment thereof further comprises a framework sequence of immunoglobulin.

22. The anti-IGF-I receptor antibody or antigen-binding fragment thereof according to claim 21, wherein the immunoglobulin framework sequence is from a vertebrate selected from the group consisting of a human, a guinea pig, a monkey, a rabbit, a cow, a pig, a horse, a sheep, a dog, a chicken, a mouse, and a rat.

23. The anti-IGF-I receptor antibody or antigen-binding fragment thereof according to claim 1, wherein said antibody or antigen-binding fragment thereof further comprises an antibody constant region from a vertebrate selected from the group consisting of a human, a guinea pig, a monkey, a rabbit, a cow, a pig, a horse, a sheep, a dog, a chicken, a mouse, and a rat.

24. A nucleic acid molecule comprising one or both of (1) and (2):
  (1) a polynucleotide sequence encoding the heavy chain variable region of the anti-IGF-I receptor antibody or antigen-binding fragment thereof according to claim 1; and
  (2) a polynucleotide sequence encoding the light chain variable region of the anti-IGF-I receptor antibody or antigen-binding fragment thereof according to claim 1.

25. A cloning vector or expression vector comprising at least one nucleic acid molecule according to claim 24.

26. A recombinant cell comprising the vector according to claim 25.

27. A process of producing an anti-IGF-I receptor antibody or antigen-binding fragment thereof, comprising:
  culturing the recombinant cell according to claim 26; and
  purifying the anti-IGF-I receptor antibody or antigen-binding fragment thereof produced from the recombinant cell.

28. A method of culturing vertebrate-derived cells in vitro, comprising contacting vertebrate-derived cells with the anti-IGF-I receptor antibody or antigen-binding fragment thereof according to claim 1.

29. The method according to claim 28, wherein said contacting results in promoting growth or inducing differentiation of the vertebrate-derived cells.

30. The method according to claim 28, wherein the anti-IGF-I receptor antibody or antigen-binding fragment thereof is adsorbed by, or immobilized to, a solid phase.

31. A pharmaceutical composition comprising the anti-IGF-I receptor antibody or antigen-binding fragment thereof according to claim 1.

32. The pharmaceutical composition according to claim 31, further comprising an additional active ingredient.

33. The pharmaceutical composition according to claim 32, wherein said additional active ingredient is one or more selected from the group consisting of a growth hormone or an analog thereof, insulin or an analog thereof, IGF-II or an analog thereof, an anti-myostatin antibody, a myostatin antagonist, an anti-activin type IIB receptor antibody, an activin type IIB receptor antagonist, a soluble activin type IIB receptor or an analog thereof, ghrelin or an analog thereof, follistatin or an analog thereof, a beta-2 agonist, and a selective androgen receptor modulator.

34. The pharmaceutical composition according to claim 32, wherein said additional active ingredient is one or more selected from the group consisting of: corticosteroid, antiemetic, ondansetron hydrochloride, granisetron hydrochloride, metoclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesic, ibuprofen, naproxen, choline magnesium trisalicylate, oxycodone hydrochloride, anti-angiogenic, antithrombotic, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative, farnesyl protein transferase inhibitor, alpha v beta 3 inhibitor, alpha v beta 5 inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

35. A method for treating a condition associated with IGF-I, comprising administering, to a human subject in need thereof, the anti-IGF-I receptor antibody or antigen-binding fragment thereof according to claim 1,
wherein said condition is selected from the group consisting of: disuse muscle atrophy, dwarfism, diabetic nephropathy, chronic renal failure, Laron syndrome, hepatic cirrhosis, hepatic fibrosis, aging, intrauterine growth restriction (IUGR), neurological disease, cerebral stroke, spinal cord injury, cardiovascular protection, diabetes, insulin resistance, metabolic syndrome, osteoporosis, cystic fibrosis, wound healing, myotonic dystrophy, AIDS-associated sarcopenia, HIV-associated fat redistribution syndrome, burn, Crohn's disease, Werner's syndrome, X-linked combined immunodeficiency disease, hearing loss, anorexia nervosa and retinopathy of prematurity, Turner's syndrome, Prader-Willi syndrome, Silver-Russell syndrome, idiopathic short stature, obesity, multiple sclerosis, fibromyalgia, ulcerous colitis, low muscle mass, myocardial ischemia and decreased bone density.

36. The method according to claim 35, wherein the anti-IGF-I receptor antibody or antigen-binding fragment thereof is parenterally administered to said human subject.

37. The method according to claim 35, wherein the administration of the anti-IGF-I receptor antibody or antigen-binding fragment thereof to said human subject produces at least one effect selected from the group consisting of an increase in muscle mass, an increase in body length, promotion of growth, an increase in milk production, promotion of reproduction, or prevention of aging.

38. A method for treating a disease caused by an effect of IGF-I or IGF-II on an IGF-I receptor, comprising administering, to a human subject in need thereof, the anti-IGF-I receptor antibody or antigen-binding fragment thereof according to claim 1,
wherein said disease is selected from the group consisting of: liver cancer, neuroblastoma, striated muscle sarcoma, bone cancer, childhood cancer, acromegalia, ovary cancer, pancreas cancer, benignant prostatic hypertrophy, breast cancer, prostate cancer, bone cancer, lung cancer, colorectal cancer, cervix cancer, synovial sarcoma, urinary bladder cancer, stomach cancer, Wilms' tumor, diarrhea associated with metastatic carcinoid and vasoactive intestinal peptide secreting tumor, vipoma, Verner-Morrison syndrome, Beckwith-Wiedemann syndrome, kidney cancer, renal cell cancer, transitional cell cancer, Ewing's sarcoma, leukemia, acute lymphoblastic leukemia, brain tumor, glioblastoma, non-glioblastomatic brain tumor, meningioma, pituitary adenoma, vestibular schwannoma, primitive neuroectodermal tumor, medulloblastoma, astrocytoma, oligodendroglioma, ependymoma, choroid plexus papilloma, gigantism, psoriasis, atherosclerosis, vascular smooth muscle restenosis, inappropriate microvascular growth, diabetic retinopathy, Graves' disease, multiple sclerosis, systemic lupus erythematosus, chronic thyroiditis, myasthenia gravis, autoimmune thyroiditis and Behcet's disease.

39. A method for increasing myoblast proliferation in a human subject, comprising administering, to a human subject in need thereof, the anti-IGF-I receptor antibody or antigen-binding fragment thereof according to claim 1.

40. A method for enhancing glucose uptake in a human subject, comprising administering, to a human subject in need thereof, the anti-IGF-I receptor antibody or antigen-binding fragment thereof according to claim 1.

41. A method for increasing muscle mass in a human subject, comprising administering, to a human subject in need thereof, the anti-IGF-I receptor antibody or antigen-binding fragment thereof according to claim 1.

42. A method for increasing tibia length in a human subject, comprising administering, to a human subject in need thereof, the anti-IGF-I receptor antibody or antigen-binding fragment thereof according to claim 1.

43. A method for inducing hypoglycemia in a human subject, comprising administering, to a human subject in need thereof, the anti-IGF-I receptor antibody or antigen-binding fragment thereof according to claim 1.

44. An anti-IGF-I receptor antibody or antigen-binding fragment thereof that exhibits an activity to induce growth of vertebrate-derived cells, wherein said antibody or antigen-binding fragment thereof comprises a heavy chain variable region comprising an amino acid sequence at least 90% identical to the entirety of the amino acid sequence of SEQ ID NO: 9; and wherein said antibody or antigen-binding fragment thereof further comprises a light chain variable region comprising an amino acid sequence at least 90% identical to the entirety of the amino acid sequence of SEQ ID NO: 10.

* * * * *